(12) United States Patent
Krishnan et al.

(10) Patent No.: US 11,898,195 B2
(45) Date of Patent: Feb. 13, 2024

(54) METHODS AND COMPOSITIONS FOR DETERMINING PH

(71) Applicants: The University of Chicago, Chicago, IL (US); National Centre for Biological Sciences, Bangalore (IN)

(72) Inventors: Yamuna Krishnan, Chicago, IL (US); Saheli Halder, Chicago, IL (US)

(73) Assignees: The University of Chicago, Chicago, IL (US); The National Centre for Biological Sciences, Bangalore (IN)

( * ) Notice: Subject to any disclaimer, the term of this patent is extended or adjusted under 35 U.S.C. 154(b) by 89 days.

(21) Appl. No.: 17/466,474

(22) Filed: Sep. 3, 2021

(65) Prior Publication Data
US 2021/0403987 A1    Dec. 30, 2021

Related U.S. Application Data

(62) Division of application No. 15/575,014, filed as application No. PCT/US2016/033050 on May 18, 2016, now Pat. No. 11,136,618.

(60) Provisional application No. 62/163,718, filed on May 19, 2015.

(51) Int. Cl.
| | |
|---|---|
| *C12N 15/11* | (2006.01) |
| *C12Q 1/6825* | (2018.01) |
| *C12Q 1/6816* | (2018.01) |
| *C12Q 1/6876* | (2018.01) |
| *C12Q 1/6809* | (2018.01) |
| *C12N 15/113* | (2010.01) |
| *G01N 33/84* | (2006.01) |
| *C12Q 1/00* | (2006.01) |
| *C12Q 1/02* | (2006.01) |

(52) U.S. Cl.
CPC .......... *C12Q 1/6809* (2013.01); *C12N 15/111* (2013.01); *C12N 15/113* (2013.01); *C12Q 1/005* (2013.01); *C12Q 1/025* (2013.01); *C12Q 1/6816* (2013.01); *C12Q 1/6825* (2013.01); *C12Q 1/6876* (2013.01); *G01N 33/84* (2013.01); *C12N 2310/14* (2013.01); *C12N 2310/3517* (2013.01)

(58) Field of Classification Search
CPC .... C12Q 1/6809; C12Q 1/025; C12Q 1/6876; C12N 15/11; C12N 15/113; G01N 33/84
See application file for complete search history.

(56) References Cited

U.S. PATENT DOCUMENTS

| | | | |
|---|---|---|---|
| 8,153,437 B2 | 4/2012 | Krishnan et al. | |
| 8,216,850 B2 | 7/2012 | Krishnan et al. | |
| 9,250,252 B2 | 2/2016 | Krishnan et al. | |
| 9,404,123 B2 | 8/2016 | Krishnan et al. | |
| 9,772,336 B2 | 9/2017 | Krishnan et al. | |
| 10,175,232 B2 | 1/2019 | Krishnan et al. | |
| 10,443,089 B2 | 10/2019 | Krishnan et al. | |
| 2009/0081679 A1 | 3/2009 | Keefe et al. | |
| 2010/0304370 A1 | 12/2010 | Krishnan et al. | |
| 2011/0033706 A1 | 2/2011 | Krishnan | |
| 2011/0223676 A1 | 9/2011 | Krishnan et al. | |
| 2012/0082975 A1 | 4/2012 | Krishnan et al. | |
| 2012/0258452 A1 | 10/2012 | Krishnan et al. | |
| 2014/0056818 A1 | 2/2014 | Krishnan et al. | |
| 2014/0335568 A1 | 11/2014 | Krishnan et al. | |
| 2016/0002713 A1 | 1/2016 | Krishnan et al. | |
| 2016/0069912 A1 | 3/2016 | Krishnan et al. | |
| 2016/0370355 A1 | 12/2016 | Krishnan et al. | |
| 2017/0101669 A1 | 4/2017 | Krishnan et al. | |
| 2018/0245137 A1 | 8/2018 | Krishnan et al. | |

FOREIGN PATENT DOCUMENTS

| | | |
|---|---|---|
| CN | 101346474 B | 6/2013 |
| EP | 3298151 B1 | 3/2021 |
| IN | 846/CHE/20143 | 2/2013 |

(Continued)

OTHER PUBLICATIONS

Halder, Saheli, "I-Switch, i-Motif Based DNA pH Sensor: Design, Delivery and pH Mapping in Endocytic Pathway", National Centre for Biological Sciences, Tata Institute of Fundamental Research, Bangalore—560065, India, Jun. 2015, pp. 1-132.
Ausubel, et al., "Current Protocols in Molecular Biology", John Wiley & Sons, New York, 1997 (Dec. 4, 2003 edition), pp. 1-25.
Brooks, T.A., et al., "Making Sense of G-quadruplex and i-Motif Functions in Oncogene Promoters", FEBS Journal, Sep. 2010, vol. 277(17), pp. 3459-3469, doi:10.1111/j.1742-4658.2010.07759.x.
Bucek, P., et al., "Spectrometric Study of the Folding Process of i-Motif-Forming DNA Sequences Upstream of the c-kit Transcription Initiation Site", Analytica Chimica Acta, 2010, vol. 683, pp. 69-77, doi:10.1016/j.aca.2010.10.008.

(Continued)

*Primary Examiner* — Sarae L Bausch
(74) *Attorney, Agent, or Firm* — McDonnell Boehnen Hulbert & Berghoff LLP

(57) ABSTRACT

Described herein are nucleic acid molecules and complexes useful as i-switch pH reporters that have increased sensitivities as a pH reporter and have alternate pH reporting capacity ranges. Aspects of the disclosure relate to a method for determining pH comprising providing a nucleic acid complex comprising: a first single-stranded nucleic acid molecule comprising the sequence $C_nXC_nYC_nZC_n$ (SEQ ID NO. 6) wherein C is cytosine; X, Y and Z are each one or more of adenine, thymine, guanine, or combinations thereof; and n is greater than or equal to 2; and wherein at least 2 cytosine residues of the first single-stranded nucleic acid molecule are modified; and a second single-stranded nucleic acid molecule that is partially or fully complementary to the first single-stranded molecule, wherein a first label is conjugated to the first single-stranded nucleic acid molecule or the second single-stranded nucleic acid molecule; and wherein the first label is capable of producing a signal, wherein the intensity of the signal varies as a function of the conformation of the nucleic acid complex; and measuring the intensity of the signal and determining the pH from the measured signal.

3 Claims, 8 Drawing Sheets

Specification includes a Sequence Listing.

(56) References Cited

FOREIGN PATENT DOCUMENTS

| IN | 1471/CHE/2011 | 6/2013 |
|---|---|---|
| IN | 3252/CHE/2011 | 6/2013 |
| WO | 2013/054286 A1 | 4/2013 |
| WO | 2014/132191 A2 | 9/2014 |
| WO | 2014132191 A2 | 9/2014 |
| WO | 2015/159122 A1 | 10/2015 |
| WO | 2018/191561 A1 | 10/2018 |

OTHER PUBLICATIONS

Chen, Y., et al., "A DNA Nanomachine Based on a Duplex-Triplex Transition", Angew. Chem. Int. Ed., 2004, vol. 43, pp. 5335-5338, doi:10.1002/anie.200460789.
Choi, J., et al., "pH-Induced Intramolecular Folding Dynamics of i-Motif DNA", J. Amer. Chem. Soc., 2011, vol. 133, pp. 16146-16153, doi:10.1021/ja2061984.
Dailey, M.M., et al., "Resolution and Characterization of the Structural Polymorphism of a Single Quadruplex-Forming Sequence", Nucleic Acids Research, 2010, vol. 38(14), pp. 4877-4888, doi:10.1093/nar/gkq166.
Datta, B., et al., "Quadruplex Formation by a Guanine-Rich PNA Oligomer", J. Am. Chem. Soc., 2005, vol. 127, pp. 4199-4207.
Edwards, E.L., et al., "A-T and C-C+ Base Pairs Can Form Simultaneously in a Novel Multistranded DNA Complex", Biochemistry, 1990, vol. 29, pp. 828-836.
Fisher, L.D., et al., Biostatistics: A Methodology for the Health Sciences (Wiley-Interscience, NY), 1993. (2nd Edition, 2014—Abstract only).
Gehring, K., et al., "A Tetrameric DNA Structure with Protonated Cytosine-Cytosine Base Pairs", Nature, 1993, vol. 363, pp. 561-565.
Idili, A., et al., "Programmable pH-Triggered DNA Nanoswitches", J. Am. Chem. Soc., 2014, vol. 136, pp. 5836-5839, doi:10.1021/ja500619w.
Jin, R., et al., "Tetraplex Formation of a Guanine-Containing Nonameric DNA Fragment", Science, Oct. 26, 1990, vol. 250(4980), pp. 543-546.
Kanehara, H., et al., "Spectroscopic Evidence for the Formation of Four-Stranded Solution Structure of Oligodeoxycytidine Phosphorothioate", Biochemistry, 1997, vol. 36(7), pp. 1790-1797.
Kaushik, M. et al., "Calorimetric Unfolding of the Bimolecular and i-Motif Complexes of the Human Telomere Complementary Strand, d(C3TA2)4", Biophysical Chemistry, 2007, vol. 126, pp. 154-164, doi:10.1016/j.ppc.2006.05.031.
Krishnan, Y, et al., "Designer Nucleic Acids to Probe and Program the Cell", Trends in Cell Biol., Dec. 2012, vol. 22(12), pp. 624-633, doi:10.1016/j.tcb.2012.10.001.
Krishnan, Y., et al., "Nucleic Acid Based Molecular Devices", Angew. Chem. Int. Ed., 2011, vol. 50, pp. 3124-3156.
Kulikowski, T., et al., "Methylation and Tautomerism of 1-Substituted 5-Fluorocytosines", Acta Biochem. Polonica, 1979, vol. 26(1/2), pp. 145-160.
Kumar, N., et al., "Tunable c-MYC LNA i-motif", Chem. Commun., 2009, pp. 1532-1534.
Leroy, J.L., et al., "Intramolecular Folding of a Fragment of the Cytosine-Rich Strand of Telomeric DNA into an i-Motif", Nucleic Acids Res., 1994, vol. 22(9), pp. 1600-1606.
Levitt, et al., "Fluorescence Lifetime and Polarization-Resolved Imaging in Cell Biology", Current Opinion in Biotechnology, Feb. 2009, vol. 20(1), pp. 28-36, doi:10.1016/j.copbio.2009.01.004, Epub Mar. 4, 2009. (Abstract only).
Lieblein, A.L., et al., "Optimizing the Kinetics and Thermodynamics of DNA i-Motif Folding", Chembiochem., 2013, vol. 14, pp. 1226-1230, doi:10.1002/cbic.201300284.
Liu, D., et al., "A Proton-Fuelled DNA Nanomachine", Angew. Chem. Int. Ed., 2003, vol. 42, pp. 5734-5736.
Liu, D., et al., "A Reversible pH-Driven DNA Nanoswitch Array", J. Am. Chem. Soc., 2006, vol. 128, pp. 2067-2071.
Liu, Z., et al., "Reporting Transient Molecular Events by DNA Strand Displacement", Chem. Commun., 2014, vol. 50, pp. 8239-8241, doi:10.1039/c4cc03291h.
Makhija, E., et al., "Probing Chromatin Structure and Dynamics Using Fluorescence Anisotropy Imaging", CRC Handbook, Imaging Biological Mechanics, 2014. (Abstract not available).
Malliavin, T.E., et al., "Stability of the I-motif Structure is Related to the Interactions between Phosphodiester Backbones", Biophysical Journal, Jun. 2003, vol. 84, pp. 3838-3847.
Meng, H., et al., "Photoelectric Conversion Switch Based on Quantum Dots with i-Motif DNA Scaffolds", Chem. Commun., 2009, pp. 2293-2295, doi:10.1039/b903325d.
Mergny, J.L., et al., "Intramolecular Folding of Pyrimidine Oligodeoxynucleotides into an i-DNA Motif", J. Am. Chem. Soc., 1995, vol. 117(35), pp. 8887-8898.
Modi, S., et al., "Two DNA Nanomachines Map pH Changes Along Intersecting Endocytic Pathways Inside the Same Cell", Nat. Nanotechol., 2013, vol. 8, pp. 459-467, doi:10.1038/nnano.2013.92.
Modi, S., et al., "A DNA Nanomachine that Maps Spatial and Temporal pH Changes Inside Living Cells", Nat. Nanotechol., 2009, vol. 4, pp. 325-330, doi:10.1038/nnano.2009.83.
Modi, S., et al., "Recombinant Antibody Mediated Delivery of Organelle-Specific DNA pH Sensors Along Endocytic Pathways", Nanoscale, 2014, vol. 6, pp. 1144-1152, doi:10.1039/c3nr03769j.
Moody, E.M., et al., "Folding of a Stable DNA Motif Involves a Highly Cooperative Network of Interactions", J. Am. Chem. Soc., 2003, vol. 125, pp. 16285-16293.
Nesterova, I.V., et al., "Rational Design of Highly Responsive pH Sensors Based on DNA i-Motif", J. Am. Chem. Soc., 2014, vol. 136, pp. 8843-8846, doi:10.1021/ja501859w.
Pasternak, A., et al., "Modulation of i-Motif Thermodynamic Stability by the Introduction of UNA (Unlocked Nucleic Acid) Monomers", Bioorg. Med. Chem. Lett., 2011, vol. 21, pp. 752-755, doi:10.1016/j.bmcl.2010.11.106.
Pasternak, A., et al., "Unlocked Nucleic Acid—An RNA Modification with Broad Potential", Org. Biomol. Chem., 2011, vol. 9, pp. 3591-3597, doi:10.1039/c0ob01085e.
Perlikova, P., et al., "Unlocked Nucleic Acids with a Pyrene-Modified Uracil: Synthesis, Hybridization Studies, Fluorescent Properties and i-Motif Stability", Chembiochem., 2014, vol. 15, pp. 146-156, doi:10.1002/cbic.201300567.
Phan, A.T., et al., "Human Telomeric DNA: G-quadruplex, i-Motif and Watson-Crick Double Helix", Nucleic Acids Research, 2002, vol. 30(21), pp. 4618-4625.
Sambrook, et al., Molecular Cloning: A Laboratory Manual, Cold Spring Harbor Laboratory, New York, 2001. (Abstract only).
Scaria, P.V., et al., "Quadruplex Structure of d(G3T4G3) Stabilized by K+ or Na+ is an Asymmetric Hairpin Dimer", Proc. Natl. Acad. Sci., USA, 1992, vol. 89, pp. 10336-10340.
Sharma, N.K., et al., "PNA C-C+ i-Motif: Superior Stability of PNA TC8 Tetraplexes Compared to DNA TC8 Tetraplexes at Low pH", Chem. Commun., 2005, pp. 4330-4332, doi:10.1039/b506870c.
Simonsson, T, et al., "A Nuclease Hypersensitive Element in the Human c-myc Promoter Adopts Several Distinct i-Tetraplex Structures", Biochem. and Biophys. Res. Commun., 2000, vol. 278(1), pp. 158-166, doi:10.1006/bbrc.2000.3783.
Surana, S., et al., "An Autonomous DNA Nanomachine Maps Spatiotemporal pH Changes in a Multicellular Living Organism", Nature Communications, 2011, vol. 2, pp. 1-7, doi:10.1038/ncomms1340.
Zhou, J., et al., "Formation of i-Motif Structure at Neutral and Slightly Alkaline pH", Mol. BioSyst., 2010, vol. 6, pp. 580-586, doi:10.1039/b919600e.
Amit, I., et al., "Voices of Biotech", 25th anniversary issue, Nature Biotechnology, Mar. 2016, vol. 34(3), pp. 270-275.
Banerjee, A., et al., "A Novel Type of Quantum Dot-Transferrin Conjugate using DNA Hybridization Mimics Intracellular Recycling of Endogenous Transferrin", Nanoscale, 2017, vol. 9(40), pp. 15453-15460.
Banerjee, A., et al., "Fast, Efficient and Stable Conjugation of Multiple DNA Strands on Colloidal Quantum Dots", Bioconjugate Chem., May 20, 2015, vol. 26(8), pp. 1582-1589.

(56) References Cited

OTHER PUBLICATIONS

Banerjee, A., et al., "Controlled Release of Encapsulated Cargo from a DNA Icosahedron using a Chemical Trigger", Angew. Chem. Int. Ed., May 28, 2013, vol. 52(27), pp. 6854-6857.

Bhatia, D., et al., "A Method to Encapsulate Molecular Cargo within DNA Icosahedra", Methods Mol. Biol., 2013, vol. 991, Chapter 8, pp. 65-80.

Bhatia, D., et al., "Gene Delivery: Designer DNA Give RNAi More Spine", Nature Nanotechnology, Jun. 3, 2012, vol. 7(6), pp. 344-346.

Bhatia, D., et al., "Synthetic, Biofunctional Nucleic Acid Based Molecular Devices", Curr. Opin. Biotechnol., Jun. 11, 2011, vol. 22(4), pp. 475-484.

Bhattacharya, S., et al., "2-Halooxyethylene Ethers of Cholesterol as Novel Single Component, Room Temperature Cholesteric LC Materials", Mol. Cryst. Liq. Cryst., 2002, vol. 381, pp. 33-41.

Bhattacharya, S., et al., "Vesicle Formation from Oligo(Oxyethylene)-Bearing Cholesteryl Amphiphiles: Site-Selective Effects of Oxyethylene Units on the Membrane Order and Thickness", Langmuir, Mar. 9, 2001, vol. 17, pp. 2067-2075.

Bhattacharya, S., et al., "First Report of Phase Selective Gelation of Oil from Oil/Water Mixtures. Possible Implications Toward Containing Oil Spills", Chem. Commun., Jan. 8, 2001, pp. 185-186.

Chakraborty, S., et al., "The Predictive Power of Synthetic Nucleic Acid Technologies in RNA Biology", Accounts of Chemical Research, Apr. 8, 2014, vol. 47(6), pp. 1710-1719.

Chakraborty, S., et al., "Kinetic Hybrid I-Motifs: Intercepting DNA with RNA to Form a DNA(2)-RNA(2) Hybrid I-Motif", Biochimie, Mar. 2, 2008, vol. 90(7), pp. 1088-1095.

Chakraborty, S., et al., "The RNA2-PNA2 Hybrid I-Motif—A Novel RNA-Based Building Block", Chem. Commun., Oct. 17, 2007, Issue 1, pp. 70-72.

Devany, J., et al., "Sub-Cellular Nanorheology Reveals Lysosomal Viscosity as a Reporter of Lysosomal Storage Diseases", Nano Letters, Jan. 9, 2018, vol. 18, pp. 1351-1359.

Ganesh, K.N., et al., "Nucleic Acids—Chemistry and Applications", J. Org. Chem., Dec. 20, 2013, vol. 78(24), pp. 12283-12287.

Ghodke, H.B., et al., "The I-Tetraplex Building Block: Rational Design and Controlled Fabrication of Robust 1D DNA Scaffolds via Non-Watson Crick Self Assembly", Angew. Chem. Int. Ed., Mar. 2, 2007, vol. 46, pp. 2646-2649.

Ghosh, A., et al., "At a Long Awaited Turning Point", Nature Nanotechnology, Jul. 2014, vol. 9(7), pp. 491-494.

Krishnan-Ghosh, Y., et al., "Advantage of the Ether Linkage between the Positive Charge and the Cholesteryl Skeleton in Cholesterol-Based Amphiphiles as Vectors for Gene Delivery", Bioconjugate Chem., Mar.-Apr. 2002, vol. 13(2), pp. 378-384.

Horsey, I., et al., "Enhanced Cooperative Binding of Oligonucleotides to Form DNA Duplexes Mediated by Metal Ion Chelation", Chem. Commun., Aug. 5, 2002, vol. 17, pp. 1950-1951.

Jani, M.S., et al., "A DNA-Based Fluorescent Probe Maps NOS3 Activity with Sub-Cellular Spatial Resolution", Nature Chem. Biol., 2020, https://doi.org/10.1038/s41589-020-0491-3, pp. 1-13.

Jani, M.S., et al., "Precision Immunomodulation with Synthetic Nucleic Acid Technologies", Nature Reviews Materials, Jun. 2019, vol. 4, pp. 451-458.

Joshi, H., et al., "Probing the Structure and in Silico Stability of Cargo Loaded DNA Icosahedron using MD Simulations", Nanoscale, 2017, vol. 9(13), pp. 4467-4477.

Krishnan, Y., et al., "Introduction: Nucleic Acid Nanotechnology", Chem. Rev., May 22, 2019, vol. 119(10), pp. 6271-6272.

Krishnan, Y., "Nano on Reflection", 10th anniversary issue, Nature Nanotechnology, Oct. 11, 2016, vol. 11, pp. 831-832.

Krishnan, Y., "Crack the Cliques, Enable Visionaries", Nature, May 14, 2015, vol. 521(7551), p. 152.

Krishnan-Ghosh, Y., et al., "PNA Forms an I-Motif", Chem. Commun., Sep. 23, 2005, vol. 42, pp. 5278-5280.

Krishnan-Ghosh, Y., et al., "Dynamic Covalent Chemistry on Self-Templating PNA Oligomers: Formation of a Bimolecular PNA Quadruplex", Chem. Commun., May 11, 2005, vol. 24, pp. 3068-3070.

Krishnan-Ghosh, Y., et al., "A PNA4 Quadruplex", J. Am. Chem. Soc., Apr. 23, 2004, vol. 126(19), pp. 5944-5945.

Krishnan-Ghosh, Y., et al., "Formation of an Interlocked Quadruplex Dimer by d(GGGT)", J. Am. Chem. Soc., 2004, vol. 126(35), pp. 11009-11016.

Krishnan-Ghosh, Y., et al., "Thermal Lipid Order-Disorder Transitions in Mixtures of Cationic Cholesteryl Lipid Analogues and Dipalmitoyl Phosphatidylcholine Membranes", J. Phys. Chem. B, Oct. 3, 2001, vol. 105(42), pp. 10257-10265.

Krishnan-Ghosh, Y., et al., "Structure of Cholest-5-en-3 beta-oxy-5-bromopentane by Single-Crystal X-ray Diffraction at 130 K", J. Mol. Structure, 2001, vol. 560(1-3), pp. 345-355.

Lannes, L., et al., "Tuning the pH-Response of I-Motif DNA Oligonucleotides", ChemBioChem, Jun. 30, 2015, vol. 16(11), pp. 1647-1656.

Modi, S., et al., "A Method to Map Spatiotemporal pH Changes Inside Living Cells using a pH Triggered DNA Nanoswitch", Methods Mol. Biol., 2011, vol. 749, Chapter 5, pp. 61-77.

Modi, S., et al., "Structural DNA Nanotechnology: From Bases to Bricks, from Structure to Function", J. Phys. Chem. Lett., Jun. 14, 2010, vol. 1(13), pp. 1994-2005.

Modi, S., et al., "A DNA Nanomachine that Maps Spatial and Temporal pH Changes in Living Cells", Nature Nanotechnology, Apr. 6, 2009, vol. 4(5), pp. 325-330.

Pal, A., et al., "Molecular Mechanism of Physical Gelation of Hydrocardons by Fatty Acid Amides of Natural Amino Acids", Tetrahedron, May 22, 2007, vol. 63(31), pp. 7334-7348.

Patel, A., et al., "ATP is a Biological Hydrotrope", Science, May 19, 2017, vol. 356(6339), pp. 753-756.

Pitchiaya, S., et al., "First Blueprint, Now Bricks: DNA as Construction Material on the Nanoscale", Chem. Soc. Rev., Sep. 12, 2006, vol. 35(11), pp. 1111-1121.

Prakash, V., et al., "Quantitative Maps of Endosomal DNA Processing by Single Molecule Counting", Angew. Chem. Int. Ed., 2019, vol. 58(10), pp. 3073-3076.

Saha, S., et al., "Tunable, Colorimetric DNA Based pH Sensors Mediated by A-Motif Formation", Chem. Commun., 2012, vol. 48(19), pp. 2513-2515.

Saha, S., et al., "pH Toggled DNA Architectures: Reversible Assembly of 3WJs into Extended 1D Architectures through A-Motif Formation", Small, May 19, 2010, vol. 6(12), pp. 1288-1292.

Saminathan, A., et al., "Chemically Resolving Lysosome Populations in Live Cells," Trends in Biochem. Sci., Apr. 2020, vol. 45(4), pp. 365-366.

Sayresmith, N., et al., "Photostable Voltage Sensitive Dyes Based on Simple, Solvatofluorochromic, Asymmetric Thiazolothiazoles", J. Am. Chem. Soc., Nov. 27, 2019, vol. 141(47), pp. 18780-18790.

Sharma, S., et al., "A DNA Aptamer for Cyclic Adenosine Monophosphate that Shows Adaptive Recognition", ChemBioChem, Jan. 15, 2020, vol. 21(1-2), pp. 157-162.

Sharma, S., et al., "A Fluorescent Nucleic Acid Nanodevice Quantitatively Images Elevated Cyclic AMP in Membrane-Bound Compartments", Small, Jul. 14, 2014, vol. 10(21), pp. 4276-4280.

Surana, S., et al., "A Method to Map Spatiotemporal pH Changes in a Multicellular Living Organism using a DNA Nanosensor", Methods Mol. Biol., 2013, vol. 991, Chapter 2, pp. 9-23.

Veetil, A., et al., "Cell-Targetable DNA Nanocapsules for Spatiotemporal Release of Caged Bioactive Small Molecules", Nature Nanotechnology, Dec. 2017, vol. 12(12), pp. 1183-1189.

Wills, A.J., et al., "Synthesis of a Polymer-Supported Oxazolidine Aldehyde for Asymmetric Chemistry", J. Org. Chem., Aug. 15, 2002, vol. 67(19), pp. 6646-6652.

Zajac, M., et al., "What Biologists Want from their Chloride Reporters: A Conversation between Chemists and Biologists", J. Cell Sci., Jan. 23, 2020, vol. 133(2), pp. 1-13.

Nicolau, Claude, et al., "Liposomes as Carriers for In Vivo Gene Transfer and Expression", Methods in Enzymology, Gene, 1987, vol. 149, pp. 157-176.

(56) References Cited

OTHER PUBLICATIONS

Wong, Tai-Kin, et al., "Appearance of β-lactamase Activity in Animal Cells Upon Liposome-Mediated Gene Transfer", Gene, 1980, vol. 10, pp. 87-94.
Cruz, D., et al., "DNA-Based Sensor Against Nitrite Oxide Radical: Evaluation of Total Antioxidant Capacity in Beverages", Journal of Electroanalytical Chemistry, Dec. 30, 2015, vol. 763, pp. 110-115.
Eroglu, E., et al., "Development of Novel FP-Based Probes for Live-Cell Imaging of Nitric Oxide Dynamics", Nature Communications, Feb. 4, 2016, vol. 7(1), pp. 1-11.
Thekkan, S., et al., "A DNA-Based Fluorescent Reporter Maps HOC1 Production in the Maturing Phagosome", Nature Chemical Biology, Dec. 10, 2018, vol. 15(12), pp. 1165-1172.
Veetil, A., et al., "DNA-Based Fluorescent Probes of NOS2 Activity in Live Brains", Proceedings of the National Academy of Sciences, Jun. 30, 2020, vol. 117(26), pp. 14694-14702.
Brenner, S., "The Genetics of Caenorhabditis Elegans", Genetics, May 1974, vol. 77, pp. 71-94.
Chakraborty, et al., "Nucleic Acid-Based Nanodevices in Biological Imaging," Annu. Rev. Biochem., Jun. 2, 2016, vol. 85, pp. 349-373.
Collot, M., et al., "CaRuby-Nano: A Novel High Affinity Calcium Probe for Dual Color Imaging", eLife, 2015, vol. 4, e05808, pp. 1-18.
Grynkiewicz, et al., "A New Generation of Ca2+ Indicators with Greatly Improved Fluorescence Properties", J. Biol. Chem., 1985, vol. 260(6), pp. 3440-3450.
Kamath, R.S. and Ahringer, J., "Genome-Wide RNAi Screening in Caenorhabditis elegans", Methods, Aug. 2003, vol. 30(4), pp. 313-321.
Shen, W-C., et al., "Disulfide Spacer Between Methotrexate and Poly(D-lysine)", The Journal of Biological Chemistry, 1985, vol. 260(20), pp. 10905-10908.
Yang, J., et al., "Evaluation of Disulfide Reduction During Receptor-Mediated Endocytosis by Using FRET Imaging", PNAS, Sep. 12, 2006, vol. 103(37), pp. 13872-13877.
Altschul, S.F., et al., "Basic Local Alignment Search Tool", J. Mol. Biol., 1990, vol. 215, pp. 403-410.
Anfinsen, C.B., "Principles that Govern the Folding of Protein Chains", Science, Jul. 20, 1973, vol. 181(4096), pp. 223-230.
Appelqvist, H., et al., "The Lysosome: From Waste Bag to Potential Therapeutic Target", J. Mol. Cell. Biol., 2013, vol. 5, pp. 214-226.
Berg, T.O., et, al., "Use of Glycyl-L-phenylalanine 2-naphthylamide, a Lysosome-Disrupting Cathepsin C Substrate, to Distinguish Between Lysosomes and Prelysosomal Endocytic Vacuoles", Biochem. J., 1994, vol. 300(Pt.1), pp. 229-236.
Bhatia, D., et al., "Icosahedral DNA Nanocapsules by Modular Assembly", Angew. Chem. Int. Ed. Engl. 2009, vol. 48, pp. 4134-4137.
Bhatia, D., et al., "A Synthetic Icosahedral DNA-Based Host-Cargo Complex for Functional In Vivo Imaging", Nat. Commun., 2011, vol. 2(339), pp. 1-8.
Bhatia, D., et al., "Quantum Dot-Loaded Monofunctionalized DNA Icosahedra for Single-Particle Tracking of Endocytic Pathways", Nat. Nanotechnol., 2016, vol. 11(12), pp. 1112-1119.
Bhuniya, S., et al., "An Activatable Theranostic for Targeted Cancer Therapy and Imaging", Angew. Chem. Int. Ed. Engl., 2014, vol. 53, pp. 4469-4474.
Blum, G., et, al., "Noninvasive Optical Imaging of Cysteine Protease Activity Using Fluorescently Quenched Activity-Based Probes", Nat. Chem. Biol., Oct. 2007, vol. 3(10), pp. 668-677.
Burgdorf, S., et al., "Spatial and Mechanistic Separation of Cross-Presentation and Endogenous Antigen Presentation". Nat. Immunol., May 2008, vol. 9(5), pp. 558-566.
Burgoyne, J.R., et al., "Cysteine Redox Sensor in PKGIa Enables Oxidant-Induced Activation", Science, Sep. 7, 2007, vol. 317(5843), pp. 1393-1397.
Chakraborty, K., et al., "High Lumenal Chloride in the Lysosome is Critical for Lysosome Function", elife, 2017, vol. 6, e28862, pp. 1-21.

Chan, P., et al., "Autopalmitoylation of TEAD Proteins Regulates Transcriptional Output of the Hippo Pathway", Nat. Chem. Biol., Apr. 2016, vol. 12(4), pp. 282-289.
Collins, D.S., et al., "Reduction of Disulfide Bonds Within Lysosomes is a Key Step in Antigen Processing", J. Immunol., 1991, vol. 147, pp. 4054-4059.
Crivat, G., et al., "Imaging Proteins Inside Cells with Fluorescent Tags", Trends Biotechnol., Jan. 2012, vol. 30 (1), pp. 8-16.
Dihazi, H., et al., "Secretion of ERP57 is Important for Extracellular Matrix Accumulation and Progression of Renal Fibrosis, and is an Early Sign of Disease Onset", J. Cell Sci., 2018, vol. 126(16), pp. 3649-3663.
Dubikovskaya, E.A., et al., "Overcoming Multidrug Resistance of Small-Molecule Therapeutics through Conjugation with Releasable Octaarginine Transporters", Proc. Natl. Acad. Sci., Aug. 26, 2008, vol. 105(34), pp. 12128-12133.
Eschenlauer, S.C.P., et al., "The Caenorhabditis elegans ERp60 Homolog Protein Disulfide Isomerase-3 has Disulfide Isomerase and Transglutaminase-like Cross-Linking Activity and is Involved in the Maintenance of Body Morphology", J. Biol. Chem., 2003, vol. 278(6), pp. 4227-4237.
Famulok, M., et al., "Functional Aptamers and Aptazymes in Biotechnology, Diagnostics, and Therapy", Chem Rev., 2007, vol. 107(9), pp. 3715-3743.
Feener, E., et al., "Cleavage of Disulfide Bonds in Endocytosed Macromolecules", J. Biol.Chem., 1990, vol. 265(31), pp. 18780-18785.
Forman-Kay, J.D., et al., "Relationship Between Electrostatics and Redox Function in Human Thioredoxin: Characterization of pH Titration Shifts Using Two-Dimensional Homo- and Heteronuclear NMR", Biochemistry, 1992, vol. 31(13), pp. 3442-3452.
Gething, M.J., et al., "Protein Folding in the Cell", Nature, Jan. 2, 1992, vol. 355, pp. 33-45.
Guermonprez, P., et al., "ER-Phagosome Fusion Defines an MHC Class I Cross-Presentation Compartment in Dendritic Cells", Nature, Sep. 25, 2003, vol. 425, pp. 397-402.
Hawkins, H.C., et al., "Comparison of the Activities of Protein Disulphide-Isomerase and Thioredoxin in Catalysing Disulphide Isomerization in a Protein Substrate", Biochem. J., 1991, vol. 275(Pt. 2), pp. 349-353.
Hogg, P.J., "Disulfide Bonds as Switches for Protein Function", Trends Biochem. Sci., Apr. 2003, vol. 28(4), pp. 210-214.
Jansens, A., et al., "Coordinated Nonvectorial Folding in a Newly Synthesized Multidomain Protein", Science, Dec. 20, 2002, vol. 298, pp. 2401-2403.
Karala, A.-R., et al., "Modulation of an Active-Site Cysteine pKa Allows PDI to Act as a Catalyst of both Disulfide Bond Formation and Isomerization", J. Mol. Biol., 2010, vol. 396, pp. 883-892.
Kathayat, R.S., et al., "A Fluorescent Probe for Cysteine Depalmitoylation Reveals Dynamic APT Signaling", Nat. Chem. Biol., Feb. 2017, vol. 13(2), pp. 150-152.
Lasecka, L., et al., "The Nairovirus Nairobi Sheep Disease Virus/ Ganjam Virus Induces the Translocation of Protein Disulphide Isomerase-Like Oxidoreductases from the Endoplasmic Reticulum to the Cell Surface and the Extracellular Space", PLoS ONE, Apr. 2014, vol. 9(4), e94656, pp. 1-15.
Lee, H., et al., "Molecularly Self-Assembled Nucleic Acid Nanoparticles for Targeted In Vivo siRNA Delivery", Nat. Nanotechnol., 2012, vol. 7(6), pp. 389-393.
Lee, M.H., et al., "Hepatocyte-Targeting Single Galactose-Appended Naphthalimide: A Tool for Intracellular Thiol Imaging in Vivo", J. Am. Chem. Soc., 2012, vol. 134, pp. 1316-1322.
Li, J., et al., "Substrate Optimization for Monitoring Cathepsin C Activity in Live Cells", Bioorg. Med. Chem., 2009, vol. 17, pp. 1064-1070.
Linder, M.E., et al., "Palmitoylation: Policing Protein Stability and Traffic", Nat. Rev. Mol. Cell. Biol., Jan. 2007, vol. 8(1), pp. 74-84.
Liu, C., et al., "Eradication of Large Colon Tumor Xenografts by Targeted Delivery of Maytansinoids", Proc. Natl. Acad. Sci., USA, Aug. 1996, vol. 93, pp. 8618-8623.
Liu, J., et al., "Functional Nucleic Acid Sensors", Chem. Rev., 2009, vol. 109, pp. 1948-1998.

(56) References Cited

OTHER PUBLICATIONS

Lloyd, J.B., "Disulphide Reduction in Lysosomes. The Role of Cysteine", Biochem. J., 1986, vol. 237, pp. 271-272.
Los, G.V., et al., "HaloTag: A Novel Protein Labeling Technology for Cell Imaging and Protein Analysis", ACS Chem. Biol., 2008, vol. 3(6), pp. 373-382.
Maiti, S., et al., "Gemcitabine-Coumarin-Biotin Conjugates: A Target Specific Theranostic Anticancer Prodrug", J. Am. Chem. Soc., 2013, vol. 135, pp. 4567-4572.
Mills, J.E., et al., "A Novel Disulfide Bond in the SH2 Domain of the C-Terminal Src Kinase Controls Catalytic Activity", J. Mol. Biol., Feb. 2, 2007, vol. 365(5), pp. 1460-1468.
Mok, H., et al., "Multimeric Small Interfering Ribonucleic Acid for Highly Efficient Sequence-Specific Gene Silencing", Nat. Mater., Jan. 24, 2010, vol. 9, pp. 272-278.
Molla, M.R., et al., "Exploring Versatile Sulfhydryl Chemistry in the Chain End of a Synthetic Polylactide", Macromolecules, Oct. 2012, vol. 45, pp. 8561-8570.
Mugherli, L., et al., "Fluorogenic Ester Substrates to Assess Proteolytic Activity", Bioorg. Med. Chem. Lett., 2006, vol. 16, pp. 4488-4491.
Nicolau, C., et al., "Liposome-Mediated Dna Transfer in Eukaryotic Cells. Dependence of the Transfer Efficiency Upon the Type of Liposomes Used and the Host Cell Cycle Stage", Biochem. Biophys. Acta, 1982, vol. 721, Pp. 185-190.
Halder, Saheli, et al., "Design of Ultrasensitive DNA-Based Fluorescent pH Sensitive Nanodevices", Nanoscale, May 20, 2015, vol. 7(22), pP. 10008-10012, doi:10.1039/C5NR01158B.
Halder, Saheli, et al., "Design of Ultrasensitive DNA-Based Fluorescent pH Sensitive Nanodevices", Electronic Supplementary Information (ESI) available: Materials and Methods, ESI Fig. 1-6, May 11, 2015, pp. 1-5, doi:10.1039/C5NR01158B.
Holzhuter, Katharina, "Spectroscopic Study of Natural and Unnatural Derivatives of the pH-Responsive Cytosine-Rich Human Telomeric DNA for Nanodevice Insight", Bachelor Thesis—Submitted to Department 14 (Chemistry, Biochemistry, Pharmacy) of the Johann-Wolfgang-von-Goethe University, Jun. 1, 2013, pp. 1-88.
Modi, Souvik, et al., "Two DNA Nanomachines Map pH Changes Along Intersecting Endocytic Pathways Inside the Same Cell", Nature Nanotechnology, May 26, 2013, vol. 8(6), pp. 459-467, doi:10.1038/nnano.2013.92.
Supplementary European Search Report, from The Hague, for European Application No. EP16797204, dated Nov. 9, 2018, pp. 1-10.
Sonoawane, "Chloride Concentration in Endosomes Measured Using a Ratioable Fluorescent Cl-Indicator", J.Biol. Chem., 2002, vol. 277(7), pp. 5506-5513.
Chakraborty, S., et al., "A Structural Map of OncomiR-1 at Single-Nucleotide Resolution", Nucleic Acids Res., published online Jul. 17, 2017, vol. 45(16), pp. 9694-9705.
Chakraborty, S., et al., "Pri-miR-17-92a Transcript Folds into a Tertiary Structure and Autoregulates its Processing", RNA, May 2012, vol. 18(5), pp. 1014-1028.
Chakraborty, S., et al., "The Poly dA Helix: A New Structural Motif for High-Performance DNA-Based Molecular Switches", Nucleic Acids Res., published online Mar. 11, 2009, vol. 37(9), pp. 2810-2817.
Dan, K., et al., "DNA Nanodevices Map Enzymatic Activity in Organelles", Nature Nanotechnology, Mar. 14, 2019, vol. 14(3), pp. 252-259.
Gavory, G, et al., "Structural Analysis of the Catalytic Core of Human Telomerase RNA by FRET and Molecular Modeling", Biochemistry, Nov. 7, 2006, vol. 45(44), pp. 13304-13311.
Ghosh, Y.K., et al., "Nature of Linkage between the Cationic Headgroup and Cholesteryl Skeleton Controls Gene Transfection Efficiency", FEBS Lett., May 19, 2000, vol. 473(3), pp. 341-344.
Bhattacharya, S., et al., "Membrane Formation from Oxyethylene Bearing Cationic Cholesterol Derivatives", Ind. J. Chem. B, Oct. 2001, vol. 40B, pp. 891-894.
Krishnan-Ghosh, Y., et al., "Dynamic Covalent Chemistry on Self-Templating Peptides: Formation of a Disulfide-Linked Beta-Hairpin Mimic", Angew. Chem. Int. Ed., May 16, 2003, vol. 42(19), pp. 2171-2173.
Leung, K.H., et al., "Dynamic RNA Nanotechnology Enters the CRISPR Toolbox", ACS Cent. Sci., Jun. 18, 2019, vol. 5(7), pp. 1111-1113.
Leung, K.H., et al., "A DNA Nanomachine Chemically Resolves Lysosomes in Live Cells", Nature Nanotechnology, Feb. 1, 2019, vol. 14(2), pp. 176-183.
Modi, S., et al., "The PNA-DNA Hybrid I-Motif: Implications for Sugar-Sugar Contacts in I-Motif Tetramerization", Nucleic Acids Res., published online Aug. 26, 2006, vol. 34(16), pp. 4354-4363.
Narayanaswamy, N. et al., "A pH-Correctable, DNA-Based Fluorescent Reporter for Organellar Calcium", Nature Methods, Jan. 2019, vol. 16(1), pp. 95-102.
Paul, A., et al., "Combining G-Quadruplex Targeting Motifs on a Single PNA Scaffold: A Hybrid (3+1) PNA-DNA Bimolecular Quadruplex", Chem. Eur. J., 2008, vol. 14(28), pp. 8682-8689.
Prakash, V., et al., "Rational Design of a Quantitative, pH-Insensitive, Nucleic Acid Based Fluorescent Chloride Reporter", Chemical Science, published online Dec. 1, 2015, vol. 7(3), pp. 1946-1953.
Salgado, E., et al., "Visualization of Ca2+ Loss from Rotavirus During Cell Entry", J. Virol., published online Sep. 26, 2018, vol. 92(24), e01327-18, pp. 1-19.
Surana, S., et al., "Designing DNA Nanodevices for Compatibility with the Immune System of Higher Organisms", Nature Nanotechnology, Sep. 2015, vol. 10(9), pp. 741-747.
Surana, S., et al., "A Method to Study In Vivo Stability of DNA Nanostructures", Methods, Nov. 2013, vol. 64(1), pp. 94-100.
Thekkan, S., et al., "A DNA-Based Fluorescent Reporter Maps HOCl Production in the Maturing Phagosome", Nature Chem. Biol., Dec. 2019, vol. 15(12), pp. 1165-1172.
Veetil, A., et al., "Chemical Control Over Membrane-Initiated Steroid Signaling with a DNA Nanocapsule", Proc. Natl. Acad. Sci. U.S.A., Sep. 18, 2018, vol. 115(38), pp. 9432-9437.

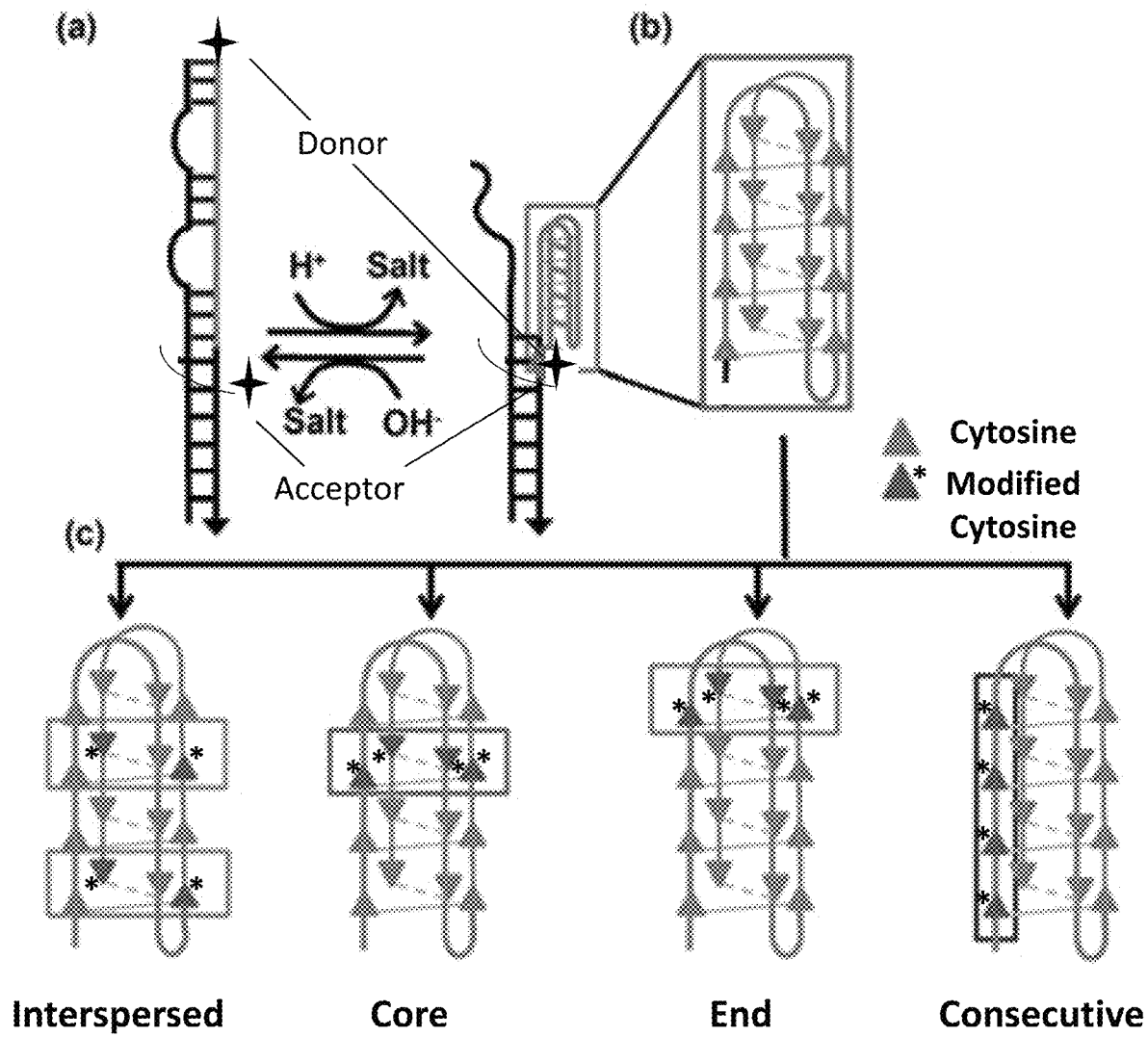
FIG. 1A-C

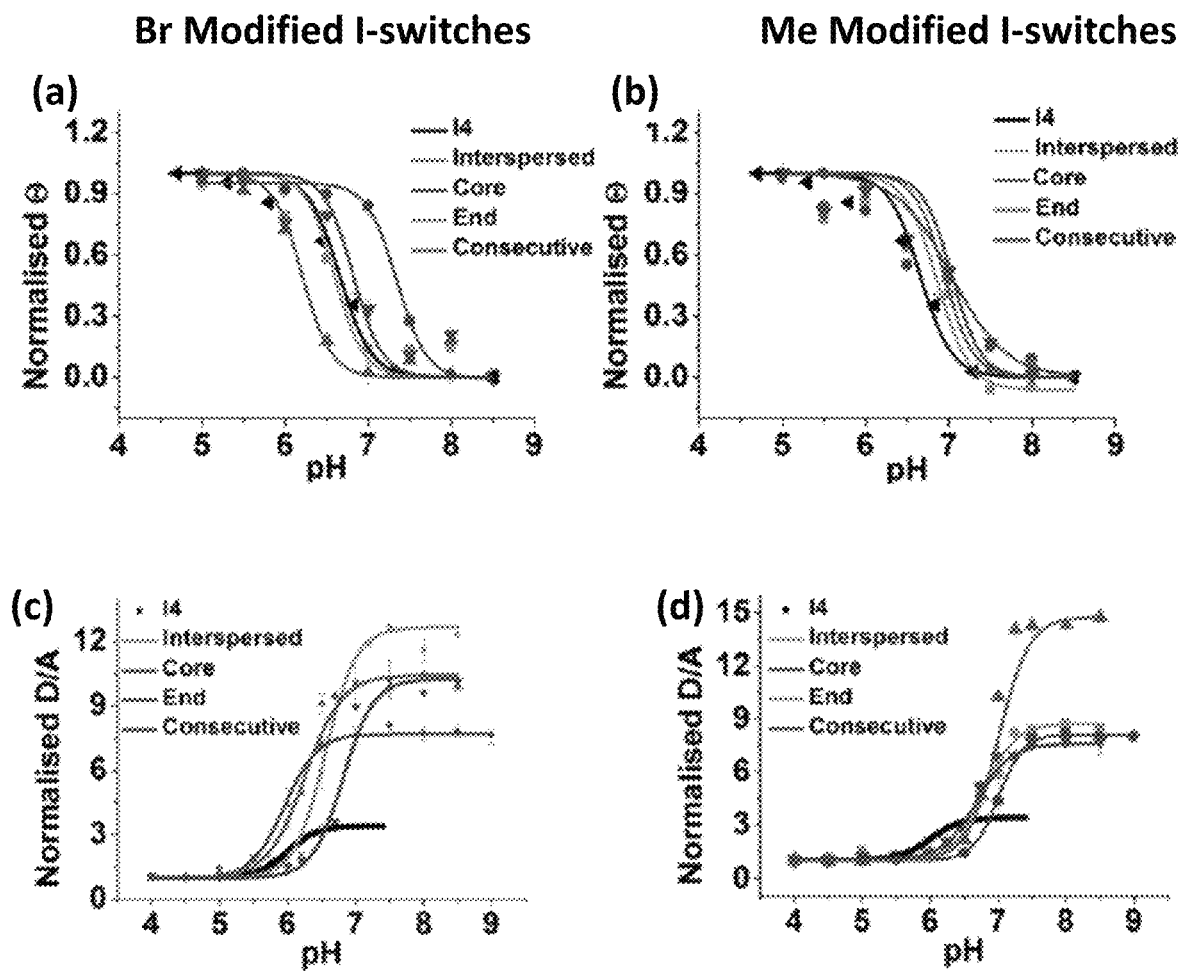
FIG. 2A-D

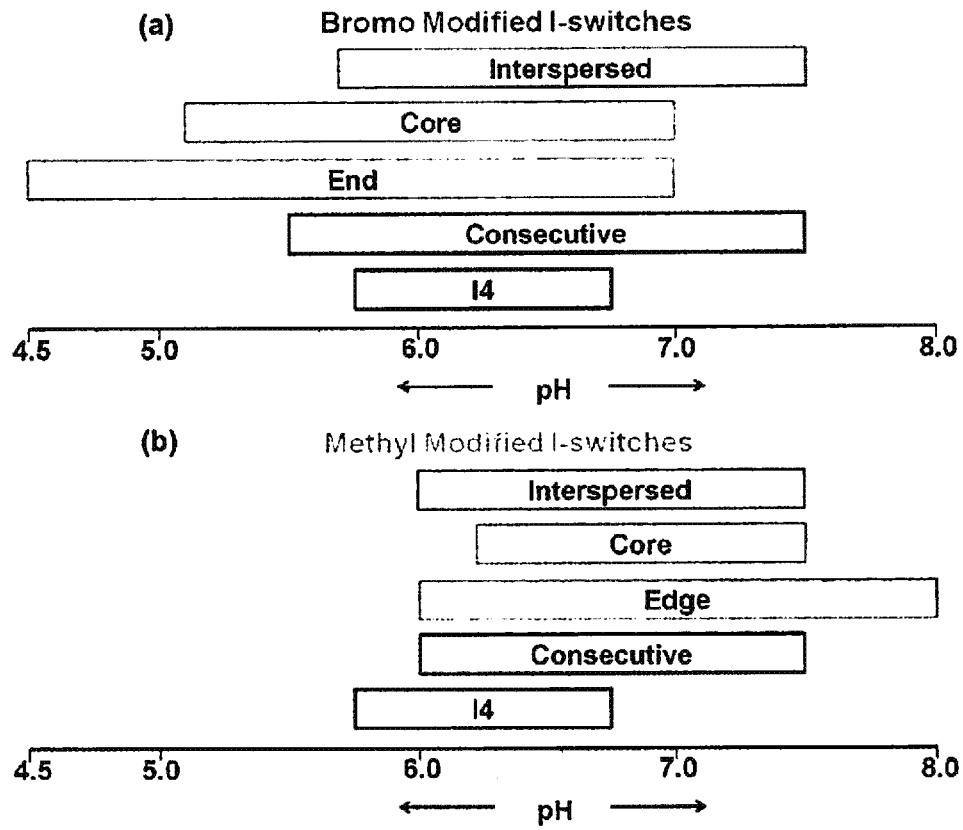
FIG. 3A-B
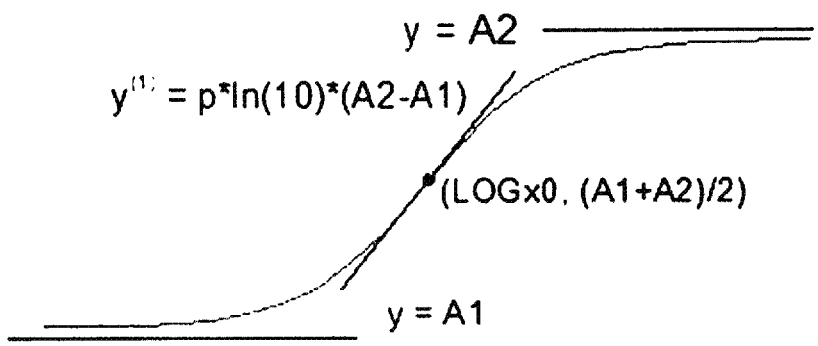
FIG. 4

A1 < A2
p > 0
bottom asymptote:
A1 = 1
top asymptote:
A2 = 2
center: LOGx0 = -1
hill slope: p = 0.2
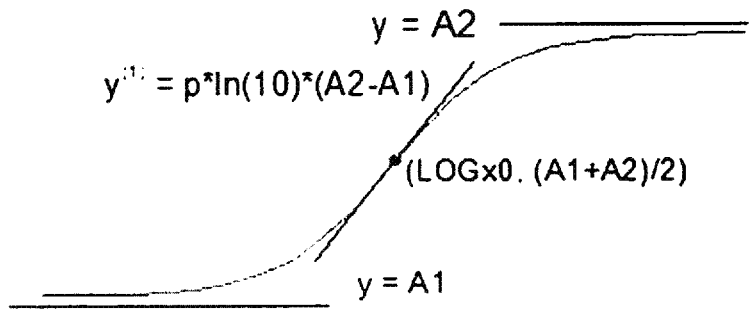
$y = A2$
$y'^{1} = p*\ln(10)*(A2-A1)$
$(LOGx0, (A1+A2)/2)$
$y = A1$
FIG. 5
FIG. 6

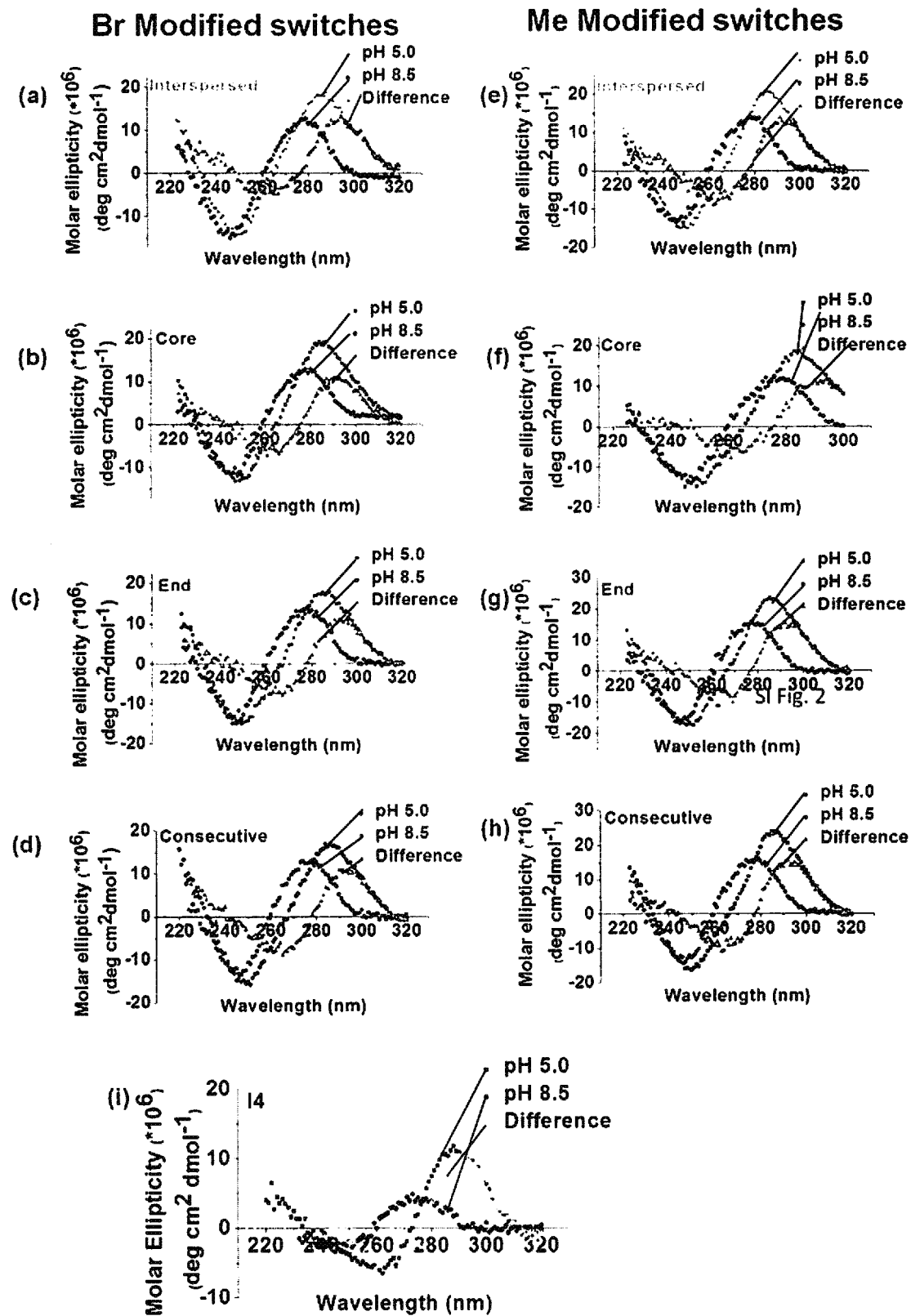
FIG. 7A-I

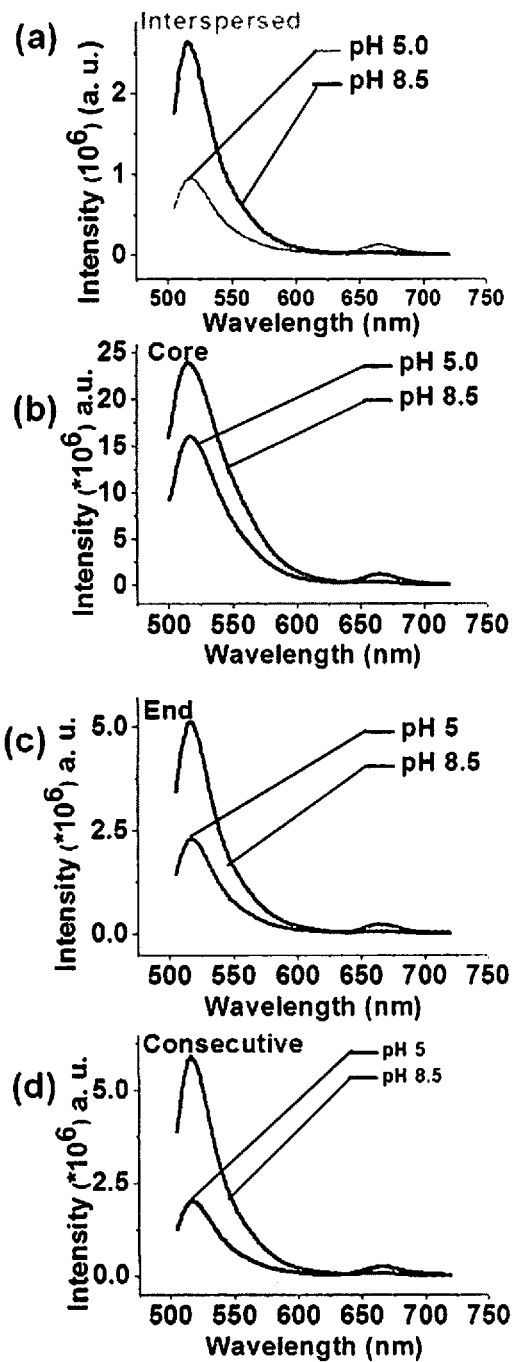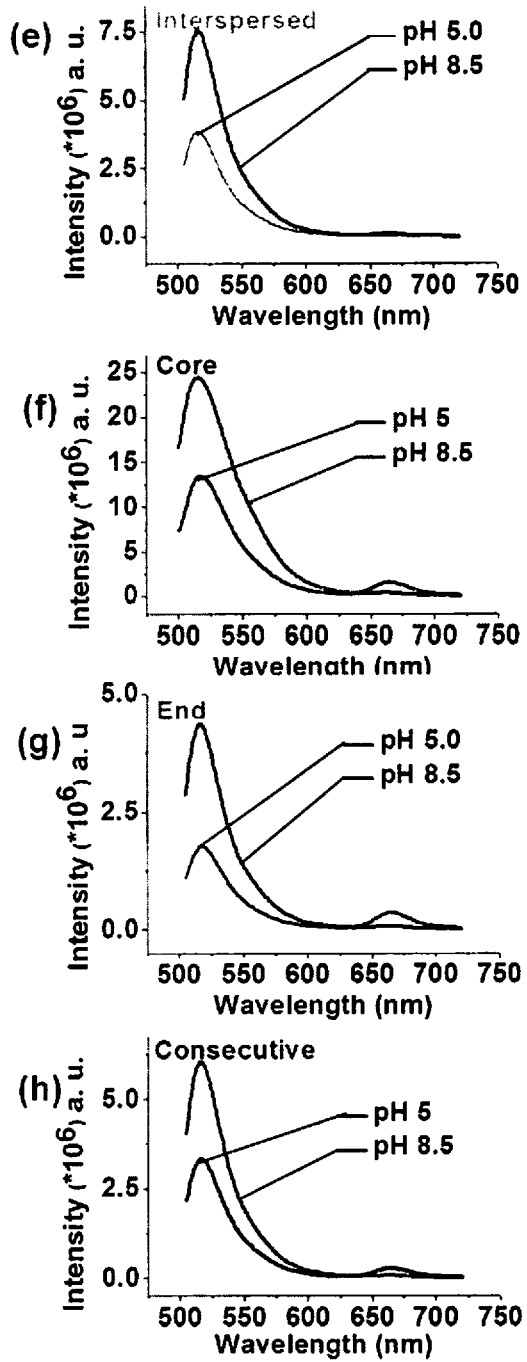
FIG. 8A-H

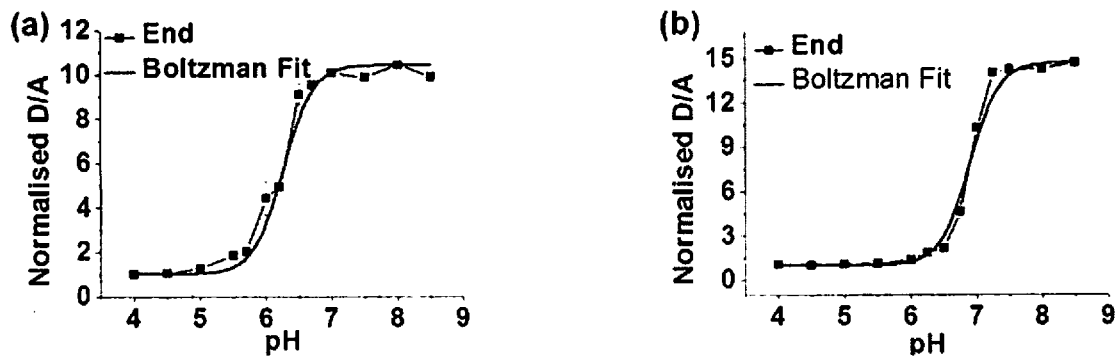
FIG. 9A-B
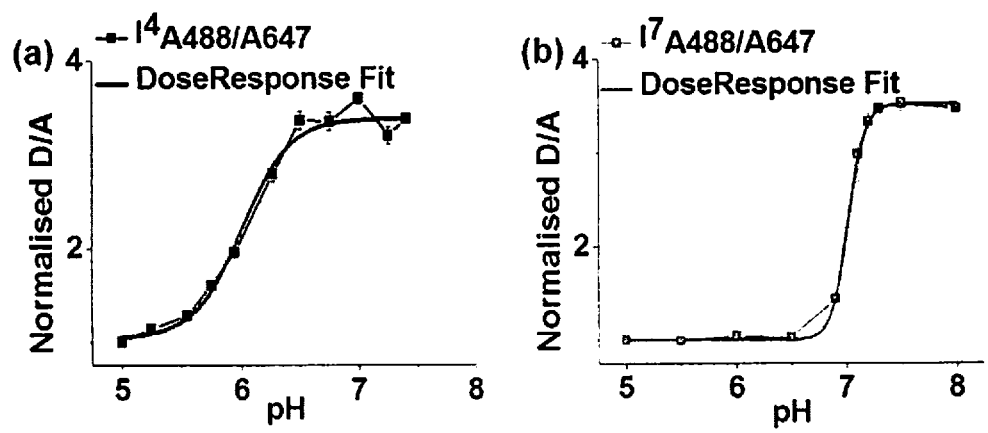
FIG. 10A-B

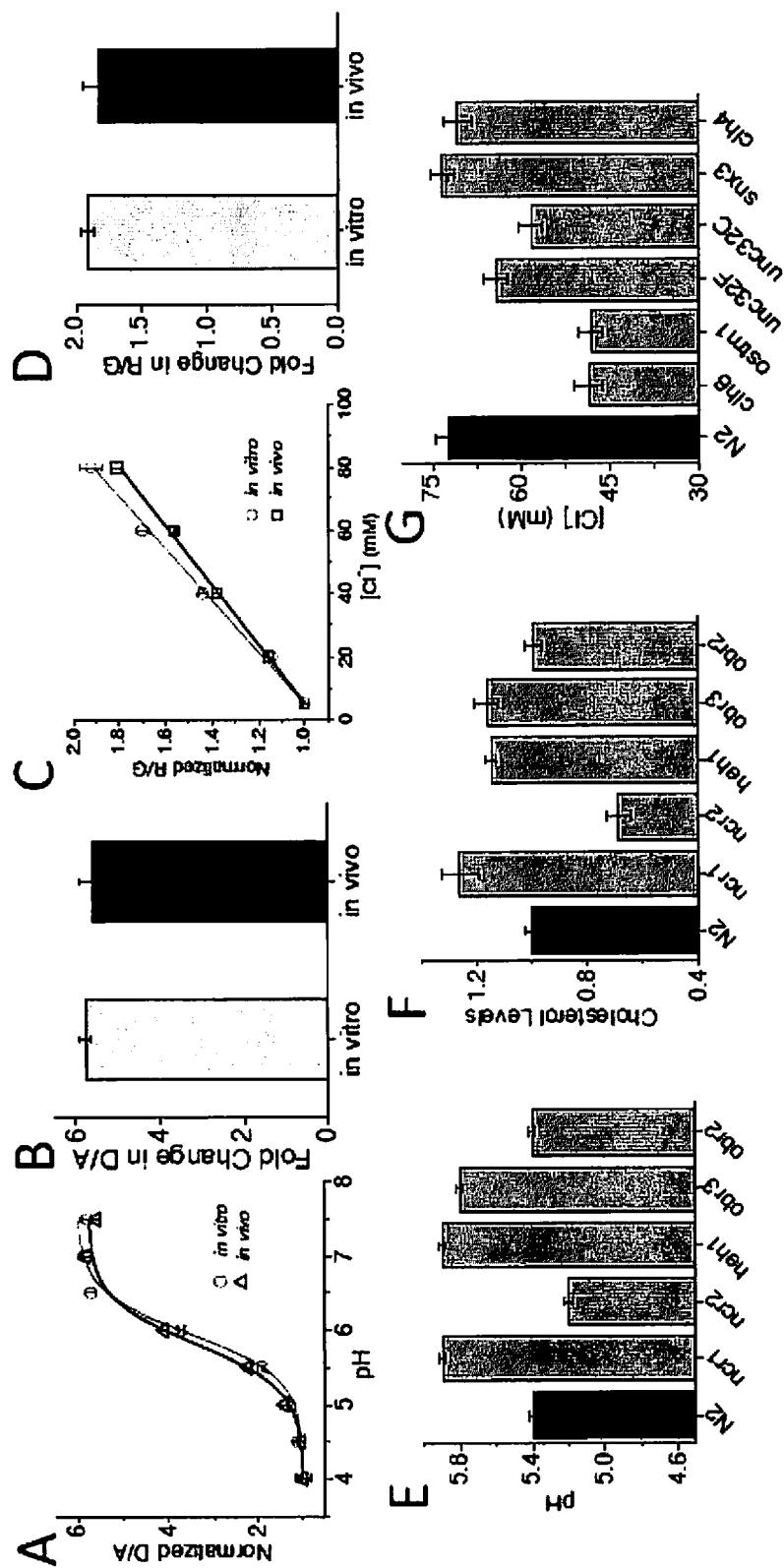
FIG. 11A-G

METHODS AND COMPOSITIONS FOR DETERMINING PH

CROSS-REFERENCE TO RELATED APPLICATIONS

This application is a divisional of U.S. patent application Ser. No. 15/575,014, filed Nov. 17, 2017, now U.S. Pat. No. 11,136,618, which is a 371 U.S. National phase of PCT/US2016/033050, filed May 18, 2016, which claims the benefit of priority of U.S. Provisional Patent Application No. 62/163,718, filed May 19, 2015, all which are hereby incorporated by reference in its entirety.

BACKGROUND OF THE INVENTION

I. Field of the Invention

Embodiments are directed generally to biology, medicine, and biotechnology.

II. Background

The availability of non Watson-Crick basepairing in DNA has led to the discovery of several functional DNA architectures that have been deployed in cellulo to yield insight on intracellular chemical environments. It was previously found that certain DNA sequence d(C5T) can form a special tetraplex structure under slightly acidic conditions where two parallel duplexes paired through C.CH+ pairs intercalated with each other in a head to tail orientation called the i-motif. It has applications as a pH reporter in the context of synthetic DNA-based conformational switches, such as the I-switch, where an i-motif induced conformational change is transduced into a photonic output using FRET. I-switches have been used to study the pH dynamics in endocytic organelles of living cells. There is evidence that the pH responsive regime of i-motif based conformational switches may be tuned by changing the number of cytosines in a stretch, since cooperativity correlates directly with i-motif stability. The issue with such strategies has been that along with the increase in midpoint of the pH-induced structural transition ($pH_{half}$) the increased cooperativity of the transition substantially narrows the overall pH sensitive regime. While a better pH resolution over a narrower pH regime can be useful in certain contexts, it is much more beneficial to alter the $pH_{half}$ without increasing cooperativity.

Cytosine hemiprotonation drives i-motif formation. The $pK_a$ of Cytosine N3 is ~4.5 and thus $DNA_4$ i-motifs are maximally stabilized at approximately pH 5.0. This typically results in I-switches with pH reporting capacity at 5.5<pH<7.0. However, different intracellular organelles maintain a different resting pH that varies from pH 4.5 (lysosomes) to pH 8.0 (mitochondria) and thus, there is a need to engineer I-switches which can respond to the whole physiological range.

SUMMARY OF THE INVENTION

Described herein are nucleic acid molecules and complexes useful as i-switch pH reporters that have increased sensitivities as a pH reporter and have alternate pH reporting capacity ranges. Aspects of the disclosure relate to a method for determining pH in a sample comprising providing a nucleic acid complex comprising: a first single-stranded nucleic acid molecule comprising the sequence $C_nXC_nYC_nZC_n$ (SEQ ID NO. 6) wherein C is cytosine; X, Y and Z are each one or more of adenine, thymine, guanine, or combinations thereof; and n is greater than or equal to 2; and wherein at least 2 cytosine residues of the first single-stranded nucleic acid molecule are modified; and a second single-stranded nucleic acid molecule that is partially or fully complementary to the first single-stranded molecule, wherein a first label is conjugated to the first single-stranded nucleic acid molecule or the second single-stranded nucleic acid molecule; and wherein the first label is capable of producing a signal, wherein the intensity of the signal varies as a function of the conformation of the nucleic acid complex; and measuring the intensity of the signal and determining the pH from the measured signal. In some embodiments, the sample is a biological sample selected from a cell, cell extract, cell lysate, tissue, tissue extract, bodily fluid, serum, blood and blood product. In some embodiments, the sample is a live cell. In some embodiments, the sample is a biological sample from a patient.

In some embodiments, a second label is conjugated to the first single-stranded nucleic acid molecule or the second single-stranded nucleic acid molecule; wherein the intensity of the signal varies as a function of at least one of the distance between the first and second labels and the relative orientation of the first and second labels.

In some embodiments, the signal intensity changes by at least twenty percent as the pH is raised from at least one of pH 4 to pH 5, pH 5 to pH 6, pH 6 to pH 7, and pH 7 to pH 8. In some embodiments, the signal intensity changes by at least 10, 20, 25, 30, 35, 40, 45, 50, 55, 60, 65, 70, 75, 80, 85, or 90% or any derivable range therein when the pH is raised from at least pH 4, 5, 6, or 7 to pH 5, 6, 7, or 8 (or any range derivable therein).

In certain embodiments, when pH ranges or values are discussed herein, the range is inclusive of the recited pH. For example, a pH range from 4.0 to 5.0 or between 4.0 and 5.0 includes the pH of 4.0 and 5.0. In other embodiments, the recited pH is excluded.

In some embodiments, the pH is determined by comparing the measured signal to a reference value. In some embodiments, the pH is determined by comparing the measured signal to a reference value. In some embodiments, the signal value and/or reference value is normalized. In some embodiments, the method further comprises creating a standard curve. A standard curve can be created by measuring the signal intensity at different known pH values. A curve can be plotted as signal intensity vs. pH. The signal intensity of an unknown pH can then be determined by finding the corresponding reference value on the plot.

In some embodiments, the method further comprises determining or quantifying a target selected from $Cl^-$, $Ca^{2+}$, $Mg^{2+}$, $Zn^{2+}$, $Cu^{2+}$, $Fe^{2+}$, $Pb^{2+}$, $Cd^{2+}$, $Hg^{2+}$, $Ni^{2+}$, $Co^{2+}$, $H^+$, $Na^+$, $K^+$, $F^-$, $Br^-$, $I^-$, Cyanide ($CN^-$), Nitrate ($NO_3$), Nitrite ($NO_2^-$), Nitric oxide (NO), Phosphate ($PO_4^{3-}$), Pyrophosphate ($P_2O_7^{4-}$) and Reactive Oxygen species. In some embodiments, the target is quantified or determined using a nucleic acid based sensor comprising: a) sensing module comprising a nucleic acid or Peptide Nucleic Acid (PNA) strand and target sensitive molecule; b) normalizing module comprising nucleic acid sequence complementary to the nucleic acid or PNA strand and target insensitive fluorophore; and c) targeting module comprising nucleic acid sequence complementary to the nucleic acid sequence of the normalizing module, optionally with aptamer. In some embodiments, the method further comprises quantifying the target by determining the fluorescence ratio of target insensitive fluorophore to target sensitive fluorophore. In some embodiments, the target sensitive molecule is selected from a group comprising SPQ (6-methoxy-N-(3-sulphopropyl) quinolinium), MACA (10-methylacridinium-9-carboxamide), MADC (10-methylacridinium-9-N,N-dimethylcarboxamide), MAMC (N-methylacridinium-9-methylcarboxylate), DMAC (2, 10-Dimethylacridinium-9-carboxaldehyde), MAA (N-methyl-9-aminoacridinium), 6-methoxy-N-(4-sulphobutyl) quinolinium, N-dodecyl-6-methoxy-quinolinium iodide, 6-methyl-N-(3-sulphopropyl) quinolinium, 6-methoxy-N-(8-octanoic acid) quinolinium bromide, 6-methoxy-N-(8-octanoic acid) quinoliniumtetraphenyl borate, 6-methyl —N-(methyl) quinolinium bromide, 6-methyl —N-(methyl) quinolinium iodide; N, N'-dimethy 1-9-9'-bisacridinium and 10,10'-Bis[3-carboxypropyl]-9,9'-biacridinium Dinitrate (BAC) or modifications and derivatives thereof, preferably 10,10'-Bis [3-carboxypropyl]-9,9'-biacridinium Dinitrate (BAC); the target insensitive fluorophore is selected from a group comprising ALEXAFLOUR 568, ALEXAFLOUR 594 and ALEXA 647, preferably ALEXA 647; and wherein the ratio of the target sensitive molecule and the target insensitive fluorophore is 1:1. In some embodiments, the sensing module comprises the sequence set forth as SEQ ID NO:1; the normalizing module comprises the sequence set forth as SEQ ID NO:2; and the targeting module comprises the sequence selected from the group comprising SEQ ID NO:3 and SEQ ID NO:4.

Further aspects of the disclosure relate to a nucleic acid complex comprising a first single-stranded nucleic acid molecule comprising the sequence $C_nXC_nYC_nZC_n$ (SEQ ID NO. 6) wherein C is cytosine; X, Y and Z are each one or more adenine, thymine, guanine, or combinations thereof; and n is greater than or equal to 2; and wherein at least 2 cytosine residues of the nucleic acid molecule are modified; and a second single-stranded nucleic acid molecule that is partially or fully complementary to the first single-stranded molecule.

In some embodiments, a first label is conjugated to the first single-stranded nucleic acid molecule or the second single-stranded nucleic acid molecule; wherein the first label is capable of producing a signal, and wherein the intensity of the signal varies as a function of the conformation of the nucleic acid complex. In some embodiments, the method and/or nucleic acid complex further comprises a second label conjugated to the first single-stranded nucleic acid molecule or the second single-stranded nucleic acid molecule; and wherein the intensity of the signal varies as a function of at least one of the distance between the first and second labels and the relative orientation of the first and second labels. In some embodiments, the first and second labels comprise a donor and acceptor pair moiety.

In some embodiments, at least or exactly 2, 3, 4, 5, 6, 7, 8, 9, 10, 12, 14, 16, or 18 (or any derivable range therein) cytosine residues of the first single-stranded nucleic acid molecule are modified.

In some embodiments, each of X, Y, and Z is a TAA. In some embodiments, n is 3, 4, or 7. In further embodiments, n is at least, at most, or exactly 3, 4, 5, 6, 7, 8, or 9 (or any derivable range therein). In some embodiments, n is 4. In some embodiments, the modification is a methyl, fluoro, bromo, hydroxymethyl, formyl, or acetyl group. In some embodiments, the cytosine is modified with a methyl or bromo group. In some embodiments, the modification is at the 5' position of the cytosine. In some embodiments, all the cytosines in the first nucleic acid molecule are modified with the same modification. In some embodiments, all the cytosines in the first nucleic acid molecule are modified with a negatively charged modification. In some embodiments, all the cytosines in the first nucleic acid molecule are modified with a positively charged modification.

In some embodiments, the first and second labels comprise a donor and acceptor pair. In some embodiments, the signal is measured using a FRET technique. In some embodiments, at least one label is selected from the group consisting of an ATTO dye, an ALEXA Flour® dye, a CY® dye, and a BODIPY dye. In some embodiments, the donor and acceptor pair are FITC and TRITC, CY3 and CY5, or ALEXA-488 and ALEXA-647. In some embodiments, the donor and acceptor pair are labels described herein. In some embodiments, the first and second label comprise a donor fluorophore and an acceptor quencher.

In some embodiments, the signal and label is directionally dependent (anisotropy). Examples of such labels include ATTO dyes, BODIPY dyes, ALEXA dyes, TMR/TAMRA dyes or CV dyes.

In some embodiments, the nucleic acid complex further comprises a nucleic acid or PNA based sensor comprising: a) sensing module comprising a nucleic acid or Peptide Nucleic Acid (PNA) strand and target sensitive molecule; wherein the target is not [H$^+$]; b) normalizing module comprising nucleic acid sequence complementary to the nucleic acid or PNA strand and target insensitive fluorophore; and c) targeting module comprising nucleic acid sequence complementary to the nucleic acid sequence of the normalizing module, optionally with aptamer. In some embodiments, either a) or b) are operatively linked to the first and/or second single-stranded nucleic acid molecule. In some embodiments, the linkage is covalent.

In certain embodiments of the methods and nucleic acid molecule and complexes described herein, the second nucleic acid strand is one that is only partially complementary to the first nucleic acid. A nucleic acid strand is fully complementary when all bases are capable of forming conventional Watson-Crick base-pairing (e.g. G-C and A-T base pairing). A nucleic acid strand is partially complementary when at least one of the base pairs is not complementary to the opposing strand. In some embodiments, the second single nucleic acid strand comprises at least 4 non-complementary nucleic acid bases. In some embodiments, the second single nucleic acid strand comprises at least, at most, or exactly 2, 3, 4, 5, 6, 7, 8, 9, 10, 12, 14, 16, 18, or 20 (or any derivable range therein) non-complementary nucleic acid bases. In some embodiments, the second nucleic acid strand comprises 8 non-complementary nucleic acid bases.

In some embodiments, the first single-stranded molecule comprises the sequence $((C_a)_nX(C_b)_nY(C_c)_nZ(C_d)_n$ (SEQ ID NO. 7) wherein $C_a$, $C_b$, $C_c$, and $C_d$ are equal to n number of consecutive cytosine residues; X, Y, and Z are one or more adenine, thymine, guanine, or combinations thereof; and n is greater than or equal to 3. In some embodiments, each of $C_a$, $C_b$, $C_c$, and $C_d$ comprise at least one modified cytosine. In some embodiments, each of $C_a$, $C_b$, $C_c$, and $C_d$ comprise at least, at most, or exactly 1, 2, 3, 4, or 5 modified cytosines (or any derivable range therein). In some embodiments, the modified cytosine is the first or last consecutive cytosine in each of $C_a$, $C_b$, $C_c$, and $C_d$. In some embodiments, n=3 and the modified cytosine is the second consecutive cytosine in each of $C_a$, $C_b$, $C_c$, and $C_d$. In some embodiments, n=4 and the modified cytosine is the second or third consecutive cytosine in each of $C_a$, $C_b$, $C_c$, and $C_d$. In some embodiments, each of $C_b$ and $C_c$ comprise at least two modified cytosines and each of $C_a$ and $C_d$ consist of unmodified cytosine. In some embodiments, $C_a$ or $C_d$ consists of modified cytosine residues. In some embodiments, $C_a$, $C_b$, $C_c$, and/or $C_d$ consist of or comprise of at least, at most, or exactly 1, 2, 3, 4, 5, 6, or 7 modified cytosine residues, or any derivable range therein.

The nucleic acid complexes described herein are useful as pH sensors, and have high sensitivity (as evidenced by fold change of D/A ratio) without a substantial change in cooperativity. In some embodiments, the method further comprises calculating a D/A ratio from the signal intensity values. In some embodiments, the D/A ratio is a normalized value.

In some embodiments, the fold change of the D/A ratio is at least 4.1, 5, 6, 7, or 7.5. In some embodiments, the fold change of the D/A ratio is at least or exactly 4.5, 5, 6, 7, 7.5, 8, 8.5, 9, 9.5, 10, 10.5, 11, 11.5, 12, 12.5, 13, or 14 (or any derivable range therein). In some embodiments, the cooperativity, compared to the unmodified I-switch, is changed less than 2 fold, or less than 1.75, 1.5, 1.25. 1, 0.75. 0.5, 0.25, 0.2, 0.1, fold or any derivable range therein. In some embodiments, the cooperativity is less than 5, 10, 15, 20, 25, 30, 35, 40, 45, or 50% different than the un-modified I-switch. In some embodiments, the fold change of the D/A ratio is at least or exactly 4.5, 5, 6, 7, 7.5, 8, 8.5, 9, 9.5, 10, 10.5, 11, 11.5, 12, 12.5, 13, or 14 (or any derivable range therein) and the cooperativity, compared to the unmodified I-switch, is changed by less than 1.75, 1.5, 1.25. 1, 0.75. 0.5, 0.25, 0.2, or 0.1 fold or any derivable range therein. In some embodiments, the $pH_{half}$ is altered without substantially increasing the cooperativity. In some embodiments, the $pH_{half}$ is at least, at most, or exactly 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, or 9.0 (or any derivable range therein). In some embodiments, the $pH_{half}$, compared to the un-modified I-switch, is at least, at most, or exactly 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 2.9, or 3.0 pH units different (or any range derivable therein). In some embodiments, the $pH_{half}$, compared to the un-modified I-switch, is at least, at most, or exactly 3, 5, 6, 8, 10, 12, 14, 16, 18, 20, 22, 24, 24, 26, 28, or 30% different (or any derivable range therein). In some embodiments, the $pH_{half}$ compared to the un-modified I-switch, is at least, at most, or exactly 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 2.9, or 3.0 pH units different or is at least, at most, or exactly 3, 5, 6, 8, 10, 12, 14, 16, 18, 20, 22, 24, 24, 26, 28, or 30% different (or any derivable range therein) and the cooperativity, compared to the unmodified I-switch, is changed by less than 1.75, 1.5, 1.25. 1, 0.75. 0.5, 0.25, 0.2, or 0.1 fold or any derivable range therein. In some embodiments, the measured value described herein (i.e., signal intensity, $pH_{half}$ fold change, or cooperativity) is a normalized value. The calculations of the values described herein are further detailed in the Examples of the application.

In some embodiments of the methods described herein, the determined pH is less than 5.5 or more than 7.0. In some embodiments, the determined pH is less than or exactly pH 5.8, 5.7, 5.6, 5.5, 5.4, 5.3, 5.2, 5.0, 4.8, 4.6, 4.4, 4.2, or 4.0 (or any derivable range therein). In some embodiments, the determined pH is more than or exactly pH 6.8, 6.9, 7.0, 7.1, 7.2, 7.3, 7.4, 7.5, 7.6, 7.7, 7.8, 8.0, 8.2, 8.4, 8.6, 8.8 or 9.0 (or any derivable range therein). In some embodiments, the nucleic acid complexes have a pH reporting capacity at pH 5.8, 5.7, 5.6, 5.5, 5.4, 5.3, 5.2, 5.0, 4.8, 4.6, 4.4, 4.2, or 4.0 (or any derivable range therein). In some embodiments, the nucleic acid complexes are capable of determining a pH value that is pH 5.8, 5.7, 5.6, 5.5, 5.4, 5.3, 5.2, 5.0, 4.8, 4.6, 4.4, 4.2, or 4.0 (or any derivable range therein). In some embodiments, the nucleic acid complexes have a pH reporting capacity at pH 6.8, 6.9, 7.0, 7.1, 7.2, 7.3, 7.4, 7.5, 7.6, 7.7, 7.8, 8.0, 8.2, 8.4, 8.6, 8.8 or 9.0 (or any derivable range therein). In some embodiments, the nucleic acid complexes are capable of determining a pH value that is pH 5.8, pH 6.8, 6.9, 7.0, 7.1, 7.2, 7.3, 7.4, 7.5, 7.6, 7.7, 7.8, 8.0, 8.2, 8.4, 8.6, 8.8 or 9.0 (or any derivable range therein).

In some embodiments, the first and second single-stranded nucleic acid molecules are capable of forming an i-motif under acidic conditions. In some embodiments, the first nucleic acid strand is capable of forming an intramolecular complex comprising two parallel-stranded C—HC+ base paired duplexes that are intercalated in an anti-parallel orientation at acidic conditions.

In some embodiments, the first and/or second single-stranded nucleic acid molecule is less than 200 nucleotides. In some embodiments, the first and/or second single-stranded nucleic acid molecule is less than, at least, or exactly 20, 30, 40, 60, 80, 100, 125, 150, 175, 200, 225, 250, 275, 300, 350, 400, 450, 500, 550, 600, 650, 700, 750, 800, 900, or 1000 nucleotides in length, or any derivable range therein.

As used herein, "nucleic acid," "nucleotide sequence," or "nucleic acid sequence" refer to a nucleotide, oligonucleotide, polynucleotide, or any fragment thereof and to naturally occurring or synthetic molecules. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

In some embodiments, the nucleic acid complex further comprises a targeting moiety. In some embodiments, the targeting moiety is a nucleic acid sequence. In some embodiments, the targeting moiety has a cognate artificial protein receptor. The artificial receptor may be, for example, a single chain variable fragment (scFv), transcription factor, Zn-fingered protein, leucine zipper, or DNA binding immunoglobulin, In some embodiments, the targeting moiety is encoded on the same nucleic acid strand as the first and/or second single-stranded nucleic acid molecule. In some embodiments, the targeting moiety is selected from an aptamer, a duplex domain targeted to an artificial protein receptor, a nucleic acid sequence that binds an anionic-ligand binding receptor, and an endocytic ligand. In some embodiments, the targeting moiety comprises a peptide directly or indirectly conjugated to the nucleic acid molecule. In some embodiments, the targeting moiety peptide comprises one or more of a fusogenic peptide, a membrane-permeabilizing peptide, a sub-cellular localization sequence, or a cell-receptor ligand. In some embodiments, the sub-cellular localization sequence targets the nucleic acid complex to a region of the cell where spatial localization of a targeted protein is present. In some embodiments, the sub-cellular localization sequence targets the nucleic acid complex to a region of the cell selected from the group consisting of: the cytosol, the endoplasmic reticulum, the mitochondrial matrix, the chloroplast lumen, the medial trans-Golgi cisternae, the lumen of lysosome, the lumen of an endosome, the peroxisome, the nucleus, and a specific spatial location on the plasma membrane. In some embodiments, the sub-cellular organelle is one that exchanges membrane directly or indirectly with the plasma membrane.

Further aspects relate to plasmid vectors, cells and compositions comprising a nucleic acid molecule or complex of the disclosure.

Further aspects relate to a nucleic acid molecule comprising the nucleic acid sequence (SEQ ID NO. 8)
5'-CCCTAACCCCTAAC*CC*CTAACC*CC*ATATATATCCTAGAACGAC

AGACAAACAGTGAGTC-3;

(SEQ ID NO. 9)
5'-CCC*CTAACC*CCTAACCC*CTAACC*CCATATATATCCTAGAACGA

CAGACAAACAGTGAGTC-3';

(SEQ ID NO. 10)
5'-C*CCCTAACCCC*TAAC*CCCTAACCCC*ATATATATCCTAGAACGA

CAGACAAACAGTGAGTC-3';
or (SEQ ID NO. 11)
5'-C*C*C*C*TAACCCCTAACCCCTAACCCCATATATATCCTAGAACGA

CAGACAAACAGTGAGTC-3';

wherein C* is a modified cytosine. The modified cytosine comprises a modification known in the art and/or as described herein. In some embodiments, the nucleic acid is single stranded. In some embodiments, the nucleic acid is in a complex with a partially complementary second single stranded nucleic acid, as described herein.

Further aspects relate to a cell comprising a nucleic acid complex described herein.

As used herein, the term "oligonucleotide" is used interchangeably with "nucleic acid molecule," and is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, which do not have a hydroxyl group at the 2' position, and oligoribonucleotides, which have a hydroxyl group in this position. Oligonucleotides also may include derivatives, in which the hydrogen of the hydroxyl group is replaced with organic groups, e.g., an allyl group. An oligonucleotide is a nucleic acid that includes at least two nucleotides.

One nucleic acid sequence may be "complementary" to a second nucleic acid sequence. As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

Oligonucleotides as described herein may be capable of forming hydrogen bonds with oligonucleotides having a complementary base sequence. These bases may include the natural bases such as A, G, C, T and U, as well as artificial bases. An oligonucleotide may include nucleotide substitutions. For example, an artificial or modified base may be used in place of a natural base such that the artificial base exhibits a specific interaction that is similar to the natural base.

An oligonucleotide that is complementary to another nucleic acid will "hybridize" to the nucleic acid under suitable conditions (described below). As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. "Hybridizing" sequences which bind under conditions of low stringency are those which bind under non-stringent conditions (6×SSC/50% formamide at room temperature) and remain bound when washed under conditions of low stringency (2×SSC, 42° C.). Hybridizing under high stringency refers to the above conditions in which washing is performed at 2×SSC, 65° C. (where SSC is 0.15M NaCl, 0.015M sodium citrate, pH 7.2).

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any other embodiment discussed herein, and vice versa. Furthermore, compositions and kits can be used to achieve recited methods. In some embodiments, the kit further comprises a nucleic acid or PNA-based sensor for quantifying a target selected from $Cl^-$, $Ca^{2+}$, $Mg^{2+}$, $Zn^{2+}$, $Cu^{2+}$, $Fe^{2+}$, $Pb^{2+}$, $Cd^{2+}$, $Hg^{2+}$, $Ni^{2+}$, $Co^{2+}$, $H^+$, $Na^+$, $K^+$, $F^-$, $Br^-$, $I^-$, Cyanide ($CN^-$), Nitrate ($NO_3^-$), Nitrite ($NO_2^-$), Nitric oxide (NO), Phosphate ($PO_4^{3-}$)), Pyrophosphate ($P_2O_7^{4-}$) and Reactive Oxygen species. In some embodiments, the disclosure relates to a kit comprising a nucleic acid complex described herein. In some embodiments, the kit further comprises a plasmid encoding a cognate artificial protein receptor. In some embodiments, the kit further comprises a nucleic acid based sensor comprising: a) sensing module comprising Peptide Nucleic Acid (PNA) strand and target sensitive molecule; b) normalizing module comprising nucleic acid sequence complementary to the PNA strand and target insensitive fluorophore; and c) targeting module comprising nucleic acid sequence complementary to the nucleic acid sequence of the normalizing module.

Further aspects of the disclosure relate to a method for screening a candidate drug in a model cell or organism comprising delivering the nucleic acid complex of the disclosure to the cell or organism; contacting the cell or organism with the candidate drug, measuring the intensity of the signal; and determining the pH from the measured signal. In some embodiments, the sample is a biological sample selected from a cell, cell extract, cell lysate, tissue, tissue extract, bodily fluid, serum, blood and blood product. In some embodiments, the sample is a live cell. In some embodiments, the sample is a biological sample from a patient.

Further aspects relate to a method for detecting the severity of a disease, the progression of the disease, or the presence of a disease, the method comprising transferring the nucleic acid complex of the disclosure to a sample; measuring the intensity of the signal; and determining the pH from the measured signal.

In some embodiments of any of the methods described herein, the method further comprises determining or targeting a target selected from $Cl^-$, $Ca^{2+}$, $Mg^{2+}$, $Zn^{2+}$, $Cu^{2+}$, $Fe^{2+}$, $Pb^{2+}$, $Cd^{2+}$, $Hg^{2+}$, $Ni^{2+}$, $Co^{2+}$, $H^+$, $Na^+$, $K^+$, $F^-$, $Br^-$, $I^-$, Cyanide ($CN^-$), Nitrate ($NO_3^-$), Nitrite ($NO_2^-$), Nitric oxide (NO), Phosphate ($PO_4^{3-}$), Pyrophosphate ($P_2O_7^{4-}$) and Reactive Oxygen species. In some embodiments, the target is quantified or determined using a nucleic acid based sensor comprising: a) sensing module comprising a nucleic acid or Peptide Nucleic Acid (PNA) strand and target sensitive molecule; b) normalizing module comprising nucleic acid sequence complementary to the nucleic acid or PNA strand and target insensitive fluorophore; and c) targeting module comprising nucleic acid sequence complementary to the nucleic acid sequence of the normalizing module, optionally with aptamer. In some embodiments, the method further comprises quantifying the target by determining the fluorescence ratio of target insensitive fluorophore to target sensitive fluorophore. In some embodiments, the target sensitive molecule is selected from a group comprising SPQ (6-methoxy-N-(3-sulphopropyl) quinolinium), MACA (10-methylacridinium-9-carboxamide), MADC (10-methylacridinium-9-N,N-dimethylcarboxamide), MAMC (N-methyl-acridinium-9-methylcarboxylate), DMAC (2, 10-Dimethylacridinium-9-carboxaldehyde), MAA (N-methyl-9-aminoacridinium), 6-methoxy-N-(4-sulphobutyl) quinolinium, N-dodecyl-6-methoxy-quinolinium iodide, 6-methyl-N-(3-sulphopropyl) quinolinium, 6-methoxy-N-(8-octanoic acid) quinolinium bromide, 6-methoxy-N-(8-octanoic acid) quinoliniumtetraphenyl borate, 6-methyl-N-(methyl) quinolinium bromide, 6-methyl —N-(methyl) quinolinium iodide; N, N'-dimethy 1-9-9'-bisacridinium and 10,10'-Bis[3-carboxypropyl]-9,9'-biacridinium Dinitrate (BAC) or modifications and derivatives thereof, preferably 10,10'-Bis[3-carboxypropyl]-9,9'-biacridiniumDinitrate (BAC); the target insensitive fluorophore is selected from a group comprising ALEXAFLOUR 568, ALEXAFLOUR 594 and ALEXA 647, preferably ALEXA 647; and wherein ratio of the target sensitive molecule and the target insensitive fluorophore is 1:1. In some embodiments, the sensing module comprises sequence set forth as SEQ ID NO:1; the normalizing module comprises the sequence set forth as SEQ ID NO:2; and the targeting module comprises a sequence selected from the group comprising SEQ ID NO:3 and SEQ ID NO:4.

In some embodiments, the model cell or organism is a model for a lysosomal storage disease. In some embodiments, the disease is a lysosomal storage disease.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-C. Schematic representation of the working principle of the I-switch and its various modifications. (FIG. 1A) Working principle of the I-switch; donor and acceptor fluorophores are shown as (+). (FIG. 1B) Schematic of i-motif formed in I-switches. Cytosine (grey triangles) modified cytosines (*) positions are indicated. Triangle apices point towards the 3' strand terminus. (FIG. 1C) I-switch variants incorporating modified cytosines used in this study. The asterisk (*) represents a modified cytosine. Each variant had only one type of modification to the modified cytosine, and 5-bromocytosine-modified variants and 5-methylcytosine-modified variants were made.

FIG. 2A-D. In vitro characterisation of all I-switch variants. (FIGS. 2A & 2B) Normalized ellipticity (Θ) at 292 nm of 1 μM native (I4) and (FIG. 2A) 5'-Bromocytosine modified (Br I-switches) I-switches (FIG. 2B) 5'-Methylcytosine modified (Me I-switches) in 1× clamping buffer is shown as a function of pH. (c&d) Donor (D) to FRET acceptor (A) ratio measurements of dually labelled I-switch assemblies as a function of pH. Normalized ratio of fluorescence intensities at 520 nm and 669 nm ($\lambda_{ex}$ 495 nm) of 50 nM (FIG. 2C) Br I-switches and (FIG. 2D) Me I-switches in 1× clamping buffer is shown as a function of pH. All experiments were performed in triplicate at RT and shown as mean±standard error of the mean. The data from FIG. 2A-D represent data from the I4 (▶) (Interspersed (■), Core (●), End (▲), and Consecutive (▼) variants.

FIG. 3A-B. pH tuning of the various I-switches. Dynamic range of —(FIG. 3A) Br modified switches compared with native (I4) switch and (FIG. 3B) Me modified switches compared with native (I4) switch.

FIG. 4. Determination of $pH_{half}$. Plots of normalized D/A v/s pH for each I-switch were fitted using a Boltzmann distribution in OriginPro 8. The sample curve and the formula used for fitting were: $y=[(A_1-A_2)/1+e^{(x-x_0)/dx}]+A_2$; where: $A_1$=initial value; $A_2$=final value; $x_0$=midpoint of the curve ($pH_{half}$); and dx=time constant. The corresponding $pH_{half}$ for each I-switch sample was obtained and reported in Table 1.

FIG. 5. Determination of cooperativity: Cooperativity was determined by fitting plots of normalized D/A values v/s pH for each I-switch using DoseResponse curve in OriginPro 8. The sample curve and the formula used for fitting are as follows: $y=A_1+[(A_2-A_1)/1+10^{(log\ x0-x)p}]$; where: $A_1<A_2$; p>0; bottom asymptote: $A_1=1$; top asymptote: $A_2=2$; centre: log $x_0$; and Hill slope: p=cooperativity. The corresponding cooperativity value was obtained and reported in Table 1.

FIG. 6. Basic design of the I-switch: pH sensing domain of three representative I-switches (randomly chosen) showing paired regions (black lines) and engineered mismatches. The first is a representation of I⁴, second is a representation of Core (5'-Bromocytosine modified switch, represented with an asterisk) while third is a representation of End (5'-Methylcytosine modified switch, represented with an asterisk) (SEQ ID NOs. 39-44).

FIG. 7A-I. In vitro characterization of I-switches using CD spectroscopy. (FIG. 7A-D) Molar ellipticity of each I-switch at pH 8.5, pH 5.0 and difference spectra (pH 5.0–pH 8.5) for Br modified I-switches. (FIG. 7E-H) CD spectra of I-switch at pH 8.5, pH 5.0 and difference spectra (pH 5.0–pH 8.5) for Me modified I-switches. (FIG. 7I) Molar ellipticity of I⁴ at pH 8.5, pH 5.0 and difference spectra (pH 5.0–pH 8.5).

FIG. 8A-H. In vitro characterization of I-switches in vitro using fluorescence spectroscopy. (FIG. 8A-D) Fluorescence spectra (505 nm-725 nm) of various Br modified I-switches at pH 5.0 and pH 8.5. (FIG. 8E-H) Fluorescence spectra (505 nm-725 nm) of various Me modified I-switches at pH 5.0 and pH 8.5.

FIG. 9A-B. Determination of $pH_{half}$. Representation of two randomly chosen D/A v/s pH traces fitted using Boltzmann curve and their corresponding parameters for (FIG. 9A) Br modified switches and (FIG. 9B) Me modified switches.

FIG. 10A-B. Determination of cooperativity. Representation of two randomly chosen D/A v/s pH traces fitted using DoseResponse curve and their corresponding parameters for (FIG. 10A) $I4^{LY}_{A488/A647}$ and (FIG. 10B) $I7_{A488/A647}$ FIG. 11A-G. (A) pH calibration curve of $I4^{LY}_{A488/A647}$ in vivo and in vitro showing normalized D/A ratios versus pH. (n=15 cells, >60 endosomes) (B) in vitro and in vivo fold change in D/A ratios of $I4^{LY}_{A488/A647}$ from pH 4.0 to pH 7.5 (C) Calibration profile of Clensor in vivo and in vitro showing normalized R/G ratio versus [Cl⁻]. (n=15 cells, >50 endosomes) (D) in vitro and in vivo fold change in R/G ratios of Clensor from 5 mM to 80 mM [CF]. (E) Lysosomal pH measured using $I4^{LY}_{A488/A647}$ in the indicated genetic backgrounds corresponding to Niemann-Pick C disease (n=10 worms, >100 lysosomes). (E) Cholesterol levels obtained from TLC analysis of total lipids equivalent to 400 µg of total protein extracted from worms of indicated genetic backgrounds. Error bars in all cases indicate s.e.m. (F) Lysosomal chloride concentrations ([Cl⁻]) as measured using Clensor in indicated genetic backgrounds corresponding to autosomal recessive osteopetrosis (n=10 worms, >100 lysosomes).

DETAILED DESCRIPTION OF THE INVENTION

The nucleic acid complexes described herein are I-switches, which are DNA nanomachines that undergo a conformational change triggered by protons. I-switches can effectively map spatiotemporal pH changes associated with endosomal maturation both in living cells as well as within cells present in a living organism. Different intracellular organelles maintain a different resting pH that varies from pH 4.5 (lysosomes) to pH 8.0 (mitochondria) and thus, there is a need to engineer I-switches which can respond to the whole physiological range. The methods and compositions described herein demonstrate a new class of modified I-switches that not only maintain functionality as pH reporters, but are also incredibly sensitive and have modified pH reporting capacity ranges.

I. NUCLEIC ACID COMPLEXES

A. I-switch

Cytosine rich DNA sequences are found in human genomes such as in telomeres and in promoters of several oncogenes, e.g., c-myc. I-switches can form a special tetraplex structure under slightly acidic condition where two parallel duplexes paired through CnCH+ pairs intercalated with each other in head to tail orientation called the i-motif. The "i-motif" is a nucleic acid (DNA and/or RNA) containing complex characterized by the presence of cytosine-rich stretches or stretches rich in cytosine derivatives, including two parallel-stranded duplexes in which the cytosines or derivatives thereof form base pairs, and the two duplexes are associated anti-parallel to one another. The pairs of cytosine or derivatives thereof of one duplex are intercalated with those of the other duplex.

The structure of an i-motif differs from that of the usual DNA duplex because the base pairing scheme involves hemiprotonated cytosines which result in the formation of C.C+ base pairs. Specifically, one of the cytosines contained in each pair is protonated. The i-motif may also exist as a tetramer formed by the association of two duplexes as described above.

The complex may be synthesized from oligonucleotide sequences including a stretch of at least two, at least three, or at least four consecutive cytosines. By modifying the number of cytosines, as well as the degree of complementarity between both strands, it is possible to modulate the response time of the I-switch and to the pH sensing range. When more cytosines contribute to the i-motif, the stability of the motif is increased. Moreover, this motif may be formed by the interaction of stretches containing different numbers of cytosines. Furthermore, a cytosine-rich stretch may contain one or two non-cytosine base(s) in between the cytosines. However, this may reduce the stability of the i-motif. The cytosine stretches which comprise the i-motif may belong to different strands of nucleic acids; however, any two of them may also be linked together covalently or non-covalently. Also, any two of them may be part of a single nucleic acid strand wherein they are separated by a stretch of specified bases.

Some exemplary I-switches and their corresponding I-motif sequences are shown in the table below:

| I-switch | Sequence of I-motif |
|---|---|
| 14 | CCCCTAACCCCTAACCCCTAACCCC (SEQ ID NO. 12) |
| 17 | CCCCCCCTAACCCCCCCTAACCCCCCCTAACCCCCCC (SEQ ID NO. 13) |
| 13 | CCCTAACCCTAACCCTAACCC (SEQ ID NO. 14) |

B. Labels

The oligonucleotides and nucleic acid molecules in the compositions and methods described herein may include one or more labels. Nucleic acid molecules can be labeled by incorporating moieties detectable by one or more means including, but not limited to, spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

As used herein, "labels" are chemical or biochemical moieties useful for labeling a nucleic acid. "Labels" include, for example, fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide.

In some embodiments, the nucleic acid molecules may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine YELLOW; Acriflavin; Acriflavin Feulgen SITSA; ALEXA Fluor 350™; ALEXA Fluor 430™; ALEXA Fluor 488™; ALEXA Fluor 532™; ALEXA Fluor 546™; ALEXA Fluor 568™; ALEXA Fluor 594™; ALEXA Fluor 633™; ALEXA Fluor 647™; ALEXA Fluor 660™; ALEXA Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-CY7; APTS; ASTRAZON Brilliant Red 4G; ASTRAZON Orange R; ASTRAZON Red 6B; ASTRAZON Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); BLANCOPHOR FFG; BLANCOPHOR SV; BOBO™-1; BOBO™-3; BODIPY 492/515; BODIPY 493/503; BODIPY 500/510; BODIPY 505/515; BODIPY 530/550; BODIPY 542/563; BODIPY 558/568; BODIPY 564/570; BODIPY 576/589; BODIPY 581/591; BODIPY 630/650-X; BODIPY 650/665-X; BODIPY 665/676; BODIPY FL; BODIPY FL ATP; BODIPY Fl-Ceramide; BODIPY R6G SE; BODIPY TMR; BODIPY TMR-X conjugate; BODIPY TMR-X, SE; BODIPY TR; BODIPY TR ATP; BODIPY TR-X SE; BO-PRO™-1; BO-PRO™-3; Brilliant Sulphoflavin FF; Calcein; Calcein Blue; CALCIUM CRIMSON™; CALCIUM GREEN; CALCIUM ORANGE; CALCOFLUOR White; CASCADE BLUE™; CASCADE YELLOW; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; CY2™; CY3.18; CY3.5™; CY3™; CY5.18; CY5.5™; CY5™; CY7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; FURA Red™; FURA Red™/Fluo-3; FURA-2; FURA-2/BCECF; Genacryl Brilliant Red B; Genacryl Brilliant Yellow 10GF; Genacryl Pink 3G; Genacryl Yellow SGF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer YELLOW; LYSO TRACKER Blue; LYSO TRACKER Blue-White; LYSO TRACKER Green; LYSO TRACKER Red; LYSO TRACKER YELLOW; LysoSensor Blue; LysoSensor Green; LysoSensor Yellow/Blue; Mag Green; Magdala Red (Phloxin B); Mag-FURA Red; Mag-FURA-2; Mag-FURA-5; Mag-Indo-1; Magnesium Green; Magnesium Orange; Malachite Green; Marina Blue; MAXILON BRILLIANT FLAVIN 10 GFF; MAXILON BRILLIANT FLAVIN 8 GFF; Merocyanin; Methoxycoumarin; MITOTRACKER Green FM; MITOTRACKER Orange; MITOTRACKER Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear YELLOW; NYLOSAN Brilliant Iavin E8G; OREGON GREEN; OREGON GREEN 488-X; OREGON GREEN™; OREGON GREEN™ 488; OREGON GREEN™ 500; OREGON GREEN™ 514; Pacific Blue; Pararosaniline (Feulgen); PBFI; PE-CY5; PE-CY7; PerCP; PerCP-CY5.5; PE-TexasRed [Red 613]; Phloxin B (Magdala Red); PHORWITE AR; PHORWITE BKL; PHORWITE Rev; PHORWITE RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion YELLOW; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; SEVRON BRILLIANT Red 2B; SEVRON BRILLIANT Red 4G; SEVRON BRILLIANT Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); TEXAS RED™; TEXAS RED-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (CALCOFLUOR White); TMR; TO-PRO-1; TO-PRO-3; TO-PRO-5; TOTO-1; TOTO-3; TriColor (PE-CY5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The nucleic acid molecules of the disclosed compositions and methods may be labeled with a quencher. Quenching may include dynamic quenching (e.g., by FRET), static quenching, or both. Illustrative quenchers may include Dabcyl. Illustrative quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

In some situations, it may be useful to include interactive labels on two or more oligonucleotides with due consideration given for maintaining an appropriate spacing of the labels on the nucleic acid molecules to permit the separation of the labels during a conformational change in the I-switch. One type of interactive label pair is a quencher-dye pair, which may include a fluorophore and a quencher. The ordinarily skilled artisan can select a suitable quencher moiety that will quench the emission of the particular fluorophore. In an illustrative embodiment, the Dabcyl quencher absorbs the emission of fluorescence from the fluorophore moiety.

In some embodiments, the proximity of the two labels can be detected using fluorescence resonance energy transfer (FRET) or fluorescence polarization. FRET is a distance-dependent interaction between the electronic excited states of two dye molecules in which excitation is transferred from a donor molecule to an acceptor molecule without emission of a photon. Examples of donor/acceptor dye pairs for FRET are known in the art and may include fluorophores and quenchers described herein such as Fluorescein/Tetramethylrhodamine, IAEDANS/Fluorescein (Molecular Probes, Eugene, Oreg.), EDANS/Dabcyl, Fluorescein/Fluorescein (Molecular Probes, Eugene, Oreg.), BODIPY FL/BODIPY FL (Molecular Probes, Eugene, Oreg.), BODIPY TMR/ALEXA 647, ALEXA-488/ALEXA-647, and Fluorescein/QSY7™.

The labels can be conjugated to the nucleic acid molecules directly or indirectly by a variety of techniques. Depending upon the precise type of label used, the label can be located at the 5' or 3' end of the oligonucleotide, located internally in the oligonucleotide's nucleotide sequence, or attached to spacer arms extending from the oligonucleotide and having various sizes and compositions to facilitate signal interactions. Using commercially available phosphoramidite reagents, one can produce nucleic acid molecules containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite.

Nucleic acid molecules may also incorporate functionalizing reagents having one or more sulfhydryl, amino or hydroxyl moieties into the nucleic acid sequence. For example, a 5' phosphate group can be incorporated as a radioisotope by using polynucleotide kinase and [γ32P]ATP to provide a reporter group. Biotin can be added to the 5' end by reacting an aminothymidine residue, introduced during synthesis, with an N-hydroxysuccinimide ester of biotin. Labels at the 3' terminus, for example, can employ polynucleotide terminal transferase to add the desired moiety, such as for example, cordycepin, 35S-dATP, and biotinylated dUTP.

Oligonucleotide derivatives are also available as labels. For example, etheno-dA and etheno-A are known fluorescent adenine nucleotides which can be incorporated into a reporter. Similarly, etheno-dC is another analog that can be used in reporter synthesis. The reporters containing such nucleotide derivatives can be hydrolyzed to release much more strongly fluorescent mononucleotides by the polymerase's 5' to 3' nuclease activity as nucleic acid polymerase extends a primer during PCR.

C. Introducing the I-Switch Into Cells

In some embodiments, the sample in which pH is to be measured can be a biological sample, e.g., a biological tissue or a cell or an organism. The method is suitable for measuring pH in a specific region of the cell, e.g., the cytosol, or an organellar space such as, but not limited to, the inner mitochondrial matrix, the lumen of the Golgi, the endoplasmic reticulum, the chloroplast lumen, the lumen of a lysosome, the nucleus, or the lumen of an endosome.

The nucleic acid molecules described herein can be readily introduced into a host cell, e.g., a mammalian (optionally human), bacterial, parasite, yeast or insect cell by any method in the art. For example, nucleic acids can be transferred into a host cell by physical, chemical or biological means. It is readily understood that the introduction of the nucleic acid molecules yields a cell in which the intracellular pH may be monitored. Thus, the method can be used to measure intracellular pH in cells cultured in vitro. The I-switch can also be readily introduced into a whole organism to measure the pH in a cell or tissue in vivo. For example, I-switch can be transferred into an organism by physical, chemical or biological means, e.g., direct injection.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York, 2001), and in Ausubel et al. (Current Protocols in Molecular Biology, John Wiley & Sons, New York, 1997).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. One colloidal system for use as a delivery vehicle in vitro and in vivo is a liposome (i.e., an artificial membrane vesicle). The preparation and use of such systems is well known in the art.

In some embodiments, the use of lipid formulations is contemplated for the introduction of the I-switch into host cells (in vitro, ex vivo or in vivo). In some embodiments, the I-switch may be associated with a lipid. The I-switch associated with a lipid may be encapsulated in the aqueous interior of a liposome, interspersed within the lipid bilayer of a liposome, attached to a liposome via a linking molecule that is associated with both the liposome and the oligonucleotide(s), entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid, lipid/I-switch compositions are not limited to any particular structure in solution. For example, they may be present in a bilayer structure, as micelles, or with a "collapsed" structure. They may also simply be interspersed in a solution, possibly forming aggregates which are not uniform in either size or shape.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In some embodiments, the lipid may be associated with a hemagglutinating virus (HVJ). This has been shown to facilitate fusion with the cell membrane and promote cell entry of liposome-encapsulated DNA. In some embodiments, the lipid may be complexed or employed in conjunction with nuclear non-histone chromosomal proteins (HMG-1). In some embodiments, the lipid may be complexed or employed in conjunction with both HVJ and HMG-1.

In some embodiments, the one or more I-switches are linked to a targeting sequence that directs the I-switch to a desired cellular compartment. Examples of targeting sequences include, but are not limited to, the amino terminal 81 amino acids of human type II membrane-anchored protein galactosyltransferase for directing the fluorescent indicator protein to the Golgi and the amino terminal 12 amino acids of the presequence of subunit IV of cytochrome c oxidase for directing a fluorescent pH indicator protein to the mitochondrial matrix. The 12 amino acids of the presequence of subunit IV of cytochrome c oxidase may be linked to the pH fluorescent indicator protein through a linker sequence.

II. COMBINATION SENSORS

The current methods, nucleic acids, and nucleic acid complexes may be used in combination with additional nucleic acid based sensors, such as those described in WO 2015/159125, which is herein incorporated by reference. Additional nucleic acid based sensors include, for example, embodiments comprising: a) sensing module comprising Peptide Nucleic Acid (PNA) strand and target sensitive molecule; b) normalizing module comprising a nucleic acid sequence complementary to the PNA strand and target insensitive fluorophore; and c) targeting module comprising a nucleic acid sequence complementary to the nucleic acid sequence of the normalizing module, optionally with aptamer.

The disclosure also relates to a method of obtaining a nucleic acid based sensor as above, said method comprising acts of: a) obtaining sensing module by conjugating a target sensitive molecule to Peptide Nucleic Acid (PNA) strand; b) obtaining normalizing module by conjugating a target insensitive fluorophore to nucleic acid sequence complementary to the PNA strand of the sensing module; c) obtaining targeting module comprising nucleic acid sequence complementary to the nucleic acid sequence of the normalizing module, and optionally conjugating with aptamer; and d) combining the sensing, the normalizing and the targeting module to obtain the nucleic acid based sensor.

The disclosure also relates to a method of identifying and optionally quantifying a target in a sample, said method comprising acts of: a) contacting and incubating the sample with nucleic acid based sensor as above; b) identifying the target by determining change in fluorescence level; and c) optionally quantifying the target by determining the fluorescence ratio of target insensitive fluorophore to target sensitive molecule.

In an embodiment of the present disclosure, the targeting module comprises a nucleic acid sequence selected from a group comprising DNA, RNA and PNA or any combinations thereof, preferably a combination of DNA and RNA; and the normalizing module comprises a nucleic acid sequence selected from a group comprising DNA, RNA and PNA or any combinations thereof, preferably DNA.

In another embodiment of the disclosure, the nucleic acid based sensor is for detecting a target selected from a group comprising $Cl^-$, $Ca^{2+}$, $Mg^{2+}$, $Zn^{2+}$, $Cu^{2+}$, $Fe^{2+}$, $Pb^{2+}$, $Cd^{2+}$, $Hg^{2+}$, $Ni^{2+}$, $Co^{2+}$, $H^+$, $Na^+$, $K^+$, $F^-$, $Br^-$, $I^-$, Cyanide ($CN^-$), Nitrate ($NO_3^-$), Nitrite ($NO_2^-$), Nitric oxide (NO), Phosphate ($PO_4^{3-}$), Pyrophosphate ($P_2O_7^{4-}$) and Reactive Oxygen species. In some embodiments, the nucleic acid based sensor is for detecting $Cl^-$ ions.

In yet another embodiment of the present disclosure, the target sensitive molecule is selected from a group comprising SPQ (6-methoxy-N-(3-sulphopropyl) quinolinium), MACA (10-methylacridinium-9-carboxamide), MADC (10-methylacridinium-9-N,N-dimethylcarboxamide), MANIC (N-methylacridinium-9-methylcarboxylate), DMAC (2, 10-Dimethylacridinium-9-carboxaldehyde), MAA (N-methyl-9-aminoacridinium), 6-methoxy-N-(4-sulphobutyl) quinolinium, N-dodecyl-6-methoxy-quinolinium iodide, 6-methyl-N-(3-sulphopropyl) quinolinium, 6-methoxy-N-(8-octanoic acid) quinolinium bromide, 6-methoxy-N-(8-octanoic acid) quinoliniumtetraphenyl borate, 6-methyl —N-(methyl) quinolinium bromide, 6-methyl —N-(methyl) quinolinium iodide; N, N'-dimethyl-9-9'-bisacridinium and 10,10'-Bis[3-carboxypropyl]-9,9'-biacridinium Dinitrate (BAC) or modifications and derivatives thereof, preferably 10,10-Bis[3-carboxypropyl]-9,9'-biacridinium Dinitrate (BAC); the target insensitive fluorophore is selected from a group comprising ALEXA-FLOUR 568, ALEXAFLOUR 594 and ALEXA 647, preferably ALEXA 647; and ratio of the target sensitive molecule and the target insensitive fluorophore is 1:1.

In some embodiments, the sensing module comprises a sequence set forth as SEQ ID NO:1; the normalizing module comprises sequence set forth as SEQ ID NO:2; and the targeting module comprises sequence selected from a group comprising SEQ ID NO:3 and SEQ ID NO:4.

| SEQ ID NO./Module | Name | Sequence |
|---|---|---|
| SEQ ID NO: 1 | PNA stand (P) | NH$_2$-Lys-ATC AAC ACT GCA-Lys-COOH |
| Module | Sensing module | Chloride sensitive molecule (BAC) + SEQ ID NO: 1 |
| SEQ ID NO: 2 | DNA strand (D2) | 5'-TATA$T$ATAGGATCTTGCTGTCTGGTGTGCAGTGTTGAT-3' (internal Alexa 647 modification on the T shown in large font and italics) |
| Module | Normalizing module | Chloride insensitive fluorophore (Alexa 647) + SEQ ID NO: 2 |
| SEQ ID NO: 3 | DNA strand (D1) | 5'-CACCAGACAGCAAGATCCTATATATA-3' |
| Module | Targeting module | SEQ ID NO: 3 |
| SEQ ID NO: 4 | DNA RNA hybrid strand (D1 Tfapt) | 5'-CACCAGACAGCAAGATCCTATATATA*GGGGGAUCAAUCCAAGGGA CCCGGAAACGCUCCCUUACACCCC*-3' This is a 69 mer RNA-DNA hybrid sequence. 26 bases from 5' end are DNA bases (Underlined). Remaining bases (43 bases-Italics) are RNA bases. The RNA C and U may be 2'fluoro modified C and U. |
| Mudule | Targeting module with RNA aptamer against human transferrin receptor | SEQ ID NO: 4 |
| SEQ ID NO: 5 | RNA aptamer | 5'-GGGGGAUCAA UCCAAGGGAC CCGGAAACGC UCCCUUACAC CCC-3' |

In some embodiments, the aptamer targets the sensor to a specific location in a cell and is selected from a group comprising DNA, RNA and PNA or any combinations thereof. In some embodiments, the aptamer is RNA aptamer that specifically binds to Human Transferrin Receptor; and the RNA aptamer comprises sequence set forth as SEQ ID NO:5. In some embodiments, the sample is a biological sample selected from a group comprising cell, cell extract, cell lysate, tissue, tissue extract, bodily fluid, serum, blood and blood product.

In some aspects, the methods of the disclosure may further comprise a method of targeting a nucleic acid based sensor, said method comprising acts of: a) obtaining nucleic acid based sensor by method as above; b) adding the sensor to cell for cellular uptake, to obtain a cell with the sensor; and c) incubating the cell obtained in step b) for the nucleic acid based sensor to follow targeted cellular pathway within the cell. In some embodiments, the cell is selected from a group comprising prokaryotic cell and eukaryotic cell In some embodiments, the targeting module of the nucleic acid based sensor is engineered to target the nucleic acid based sensor to follow cellular pathway within the cell.

The analyte sensors described herein may also be used in combination with the pH sensors in the methods, compositions, and kits described herein. In some aspects, the kit may further comprise components selected from group of sensing module, targeting module, normalizing module, nucleic acid based sensor, cell, sample and instructions manual or any combinations thereof.

Aspects of the disclosure relate to a nucleic acid based sensor comprising sensing module, normalizing module and targeting module. The said sensor is for detecting target ions or molecules. The sensors may be used in combination with the pH sensors in the methods described throughout. Additionally, the sensors may be operatively linked to the pH sensors described herein. Operatively linked refers to a linkage that effectively links the two molecules together but may not necessarily be a covalent linkage, such as linkage through two proteins, which involves van der Waals forces. In some embodiments, the pH sensor and analyte sensor are covalently linked.

In some embodiments, the sensing module comprises Peptide Nucleic Acid (PNA), the targeting module comprises DNA or RNA or PNA or any combinations thereof, and the normalizing module comprises DNA or RNA or PNA or any combinations thereof. In some embodiments, the sensing module of the nucleic acid based ratio-metric sensor is a peptide nucleic acid (PNA). The strand is conjugated to target sensitive molecule, for ex.: a small, fluorescent, chloride ion-sensitive molecule such as BAC (10, 10'-Bis[3-carboxypropyl]-9,9'-biacridinium Dinitrate). In some embodiments, the normalizing module is a target insensitive fluorophore, for ex.: a chloride ion insensitive fluorophore such as ALEXA 647, conjugated to DNA sequence that is complementary to PNA of the sensing module. Further, the targeting module is a second DNA sequence complementary to the DNA of normalizing module. In some embodiments, the sequence of the normalizing module shares partial complementarity with the sequence of the PNA strand of the sensing module. In an embodiment, the sequence of the targeting module shares partial complementarity with the sequence of the normalizing module.

The current disclosure relates to the use of a nucleic acid based fluorescent ratio-metric sensor for detection of target in methods and kits described herein. In some embodiments, the disclosure relates to a nucleic acid based fluorescent ratio-metric sensor for ion. In some embodiments, the present disclosure relates to a nucleic acid based fluorescent ratio-metric sensor for molecule.

In some embodiments, the current disclosure relates to a method to study the function and localization of any ion channel by measuring the concentration of relevant ion in a specific location within the cell, instead of measurement of ionic current. This sensor is also used to measure ion concentration in lifetime measurement mode, which is concentration independent.

In some embodiments, in the presence of target, the fluorescence intensity of the target sensitive fluorophore decreases (collisional quenching). The decrease in the fluorescence intensity is the read out of the target concentration. In some embodiments, the nucleic acid based fluorescent ratio-metric sensor measures chloride ion concentration (Cr), and may be referred to as "Clensor" (chloride sensor) or nucleic acid based sensor.

In an embodiment of the present disclosure, the sensor module of nucleic acid based sensor is made up of PNA set forth as SEQ ID NO:1 along with target sensitive molecule. The normalizing module is made up of DNA set forth as SEQ ID NO:2 along with target insensitive fluorophore. The targeting module is made up of DNA set forth as SEQ ID NO:3 or SEQ ID NO:4.

In the present disclosure, PNA or PNA strand or PNA sequence is used interchangeably and has the same scope or meaning. In the present disclosure, DNA or DNA strand or DNA sequence is used interchangeably and has the same scope or meaning. In the present disclosure, RNA or RNA strand or RNA sequence is used interchangeably and has the same scope or meaning.

In some embodiments, the sensor of the present disclosure self assembles all its three different modules through Watson-Crick base pairing, which is stable under physiological conditions.

In embodiments of the present disclosure, two types of targeting modules are used: A) DNA only and B) a combination of DNA and RNA. The targeting module comprising only DNA hybridizes to normalizing module to form the dsDNA domain required for intracellular targeting via an anionic ligand binding receptor (ALBR). The RNA sequence used in combination with DNA in the targeting module is used to achieve targeting to Transferrin pathway.

In some embodiments, a DNA strand is used as normalizing module. In an embodiment of the present disclosure, the sensor has a dsDNA part (minimum 8 bp sequence) resulting from the hybridization of targeting and normalizing module for the intracellular targeting. In an embodiment, the sensor comprises d(AT)4 sequence and hence is targeted to any given compartment in any cell that expresses scFv tagged protein of choice.

The disclosure provides for measurement of Chloride ion concentration and the sequences, fluorophores etc. used to prepare the Clensor sensor molecule only by way of exemplification. The scope of the present disclosure is not limited to only the combination of particular target ion/molecule, sequences or fluorophores that make up the specific sensor molecule or to the measurement of the specific target ion/molecule. The sequences involved in the targeting, sensing or normalizing modules can be varied and conjugated depending on the requirement to different target sensitive molecules and target insensitive fluorophores to prepare various sensor molecules that measure concentration of different molecules and ions.

III. TARGETING MOTIFS

The nucleic acid molecules and complexes of the disclosure may comprise a targeting motif. A "targeting motif" as used herein is a molecule such as a nucleic acid, small molecule, or polypeptide that has an affinity for a certain target or, by virtue of its chemical makeup, is targeted to a particular location in the cell. The targeting motif can act as a handle to target the nucleic acid complexes of the disclosure to different subcellular locations. The targeting motif may be a nucleic acid that binds to a receptor protein, and the receptor protein may be one that is intracellularly targeted or conjugated to a protein that is intracellularly targeted. The targeting motif or receptor protein may be a targeting nucleic acid or a protein such as a plasma membrane protein that is endocytosable, any proteins that possess a natural receptor, a protein that traffics between intracellular locations via the plasma membrane, toxins, viruses and viral coat proteins, cell penetrating peptides, signal sequences, intracellular targeting sequences, small organic molecules, endocytic ligands and trafficking proteins. In some embodiments, the targeting motif is an aptamer, a duplex domain targeted to an artificial protein receptor, a nucleic acid sequence that binds an anionic-ligand binding receptor, or an endocytic ligand. The targeting motif may also be a G4 core sequence or ribozyme.

IV. IN VIVO/EX VIVO DETECTION OF PH IN CELLS OR TISSUES USING THE I-SWITCH

Disclosed herein are methods for determining pH comprising providing a nucleic acid complex comprising: a first single-stranded nucleic acid molecule comprising the sequence $C_nXC_nYC_nZC_n$ (SEQ ID NO. 6), wherein C is cytosine; X, Y and Z are each one or more of adenine, thymine, guanine, or combinations thereof; and n is greater than or equal to 2; and wherein at least 2 cytosine residues of the first single-stranded nucleic acid molecule are modified; and a second single-stranded nucleic acid molecule that is partially or fully complementary to the first single-stranded molecule, wherein a first label is conjugated to the first single-stranded nucleic acid molecule or the second single-stranded nucleic acid molecule; and wherein the first label is capable of producing a signal, wherein the intensity of the signal varies as a function of the conformation of the nucleic acid complex; and measuring the intensity of the signal and determining the pH from the measured signal. The nucleic acid molecules described herein are useful as pH sensors called I-switches.

The methods described herein may be used to monitor the pH changes in real-time during cellular processes. In some embodiments, the methods are for monitoring endocytosis. While not wishing to be limited by theory, acidification plays a major role in facilitating cargo dissociation from receptors or in mediating cellular entry of toxins and viruses during endocytosis. The I-switch exhibits a pH response inside cells illustrated by the capture of spatiotemporal pH changes associated with endocytosis in living cells.

Fluorescence in the sample can be measured in a variety of ways, such as using a fluorometer or fluorescence microscopy. In general, excitation radiation, from an excitation source having a first wavelength, passes through excitation optics. The excitation optics cause the excitation radiation to excite the sample. In response, labels associated with the one or more I-switches in the sample emit radiation which has a wavelength that is different from the excitation wavelength. Collection optics then collect the emission from the sample. The device can include a temperature controller to maintain the sample at a specific temperature while it is being scanned. If desired, a multi-axis translation stage can be used to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the detecting includes measuring the magnitude of the signal generated, wherein the magnitude indicates the pH of the cell or region thereof. In one embodiment, the emission from the acceptor fluorophore increases as the I-switch forms a closed state, i.e., as the i-motif is formed when the pH decreases. Likewise, the emission from the acceptor fluorophore decreases as the I-switch assumes an open state, i.e., as the i-motif dissociates when the pH increases. For fluorescence quenching, the emission from the fluorophore decreases as the I-switch forms a closed state, i.e., as the i-motif is formed when the pH decreases. Likewise, the emission from the fluorophore increases as the I-switch forms an open state, i.e., as the i-motif dissociates when the pH increases.

As used herein, an "increase" (or "decrease") in a signal from the I-switch refers to the change in a signal in the sample compared to a reference sample. The reference sample may be a control sample (e.g., an untreated population of cells where the effects of a drug or agent are being examined), or it may be the same sample at a different period of time, for instance, where the intracellular pH is being monitored to follow one or more cellular processes.

As used herein, the term "detectable" refers to a property of the I-switch that allows one to determine the pH of a biological sample by detecting activity, e.g., fluorescence activity, possessed by the I-switch under certain pH conditions. In some embodiments, the signal from the I-switch is normalized by plotting the donor/acceptor (D/A) signal ratio as a function of pH in a standard reference sample. pH variation on a doubly-labeled I-switch changes the ratio between its closed and open states thereby resulting in different ratios of the donor and acceptor intensities (D/A) because of FRET in the closed state due to i-motif formation.

In one embodiment, a pH calibration curve may be generated to which test samples may be compared and normalized. An intracellular calibration curve may be generated according to methods described in U.S. Patent Application No.: 20100304370, which is herein incorporated by reference. Briefly, cells are pulsed, washed, incubated with an ionophore in buffers at a given pH and then mildly fixed. Donor and acceptor FRET images are acquired from which D/A ratios are obtained. The mean D/A of individual cells or regions thereof at each pH are plotted as a function of pH for the intracellular pH calibration curve. The D/A ratio of the test sample can be compared to the calibration curve. Related methods are also described in the Examples of the application.

In some embodiments, intracellular pH may be monitored for the purposes of examining cellular phenomena and/or screening the effects of various compounds, wherein the level of the signal from an I-switch (e.g., increased or decreased signal) in a test sample at a first time point is determined and compared with the level found in a test sample obtained at a later time point. The change in signal may reflect a relative change in pH between the two samples. For example, where a FRET pair is used as a label, an increase in signal from one time point to another may indicate an increase in pH between the two time points. Likewise, a decrease in signal from one point to another may indicate a decrease in pH. The absolute level of signal may be compared to a reference sample of known standards or reference samples in order to determine the precise pH of the sample. The sample can be classified or assigned to a particular pH value based on how similar the measured levels were compared to the control levels for a given group.

As one of skill in the art will understand, there will be a certain degree of uncertainty involved in making this determination. Therefore, the standard deviations of the control group levels can be used to make a probabilistic determination and the method of this disclosure are applicable over a wide range of probability-based determinations. Thus, for example, and not by way of limitation, in one embodiment, if the measured level of signal falls within 2.5 standard deviations of the mean of any of the control groups, then that sample may be assigned to that group. In another embodiment if the measured level of signal falls within 2.0 standard deviations of the mean of any of the control groups then that sample may be assigned to that group. In still another embodiment, if the measured level of signal falls within 1.5 standard deviations of the mean of any of the control groups then that sample may be assigned to that group. In yet another embodiment, if the measured level of signal is 1.0 or less standard deviations of the mean of any of the control groups levels then that sample may be assigned to that group. Thus, this process allows determination, with various degrees of probability, in which group a specific sample should be placed.

Statistical methods can also be used to set thresholds for determining when the signal intensity in a test sample can be considered to be different than or similar to the reference level. In addition, statistics can be used to determine the validity of the difference or similarity observed between a test sample's signal intensity and the reference level. Useful statistical analysis methods are described in L. D. Fisher & G. vanBelle, Biostatistics: A Methodology for the Health Sciences (Wiley-Interscience, N Y, 1993). For instance, confidence ("p") values can be calculated using an unpaired 2-tailed t test, with a difference between groups deemed significant if the p value is less than or equal to 0.05.

The nucleic acid complexes described herein are useful as pH sensors and may vary in their respective pKa, and the differences in pKa can be used to select the most suitable I-switch sensor for a particular application. In general, a sensor should be used whose pKa is close to the pH of the sample to be measured. For example, the pKa may be within 1.5 pH unit, within 1.0 pH unit, or within 0.5 pH units of the sample.

To minimize artefactually low fluorescence measurements that occur due to cell movement or focusing, the fluorescence of the I-switch can be compared to the fluorescence of a second sensor, e.g., a second I-switch that is also present in the measured sample. The second I-switch should have an emission spectra distinct from the first I-switch so that the emission spectra of the two sensors can be distinguished. Because experimental conditions such as focusing and cell movement will affect fluorescence of the second sensor as well as the first sensor, comparing the relative fluorescence of the two sensors may allow for the normalization of fluorescence. A convenient method of comparing the samples is to compute the ratio of the fluorescence of the first fluorescent protein pH sensor to that of the second fluorescent protein pH sensor.

In some embodiments, circular dichroism spectroscopy may be used to detect changes in the secondary structure of the I-switch in response to changes in pH. Circular Dichroism (CD) is observed when optically active matter absorbs left and right hand circular polarized light slightly differently. It is measured with a CD spectropolarimeter. In another embodiment, change in intracellular pH may be detected by observing Raman band changes in the I-switch. In this embodiment, the I-switch contains a gold nanoparticle label and a Raman tag. The Raman band changes may be detected when the gold nanoparticle is brought close to a Raman tag.

In some embodiments, FLIM is used to measure the conformational change upon i-motif formation. In some embodiments, anisotropy imaging is used to measure the conformational change. Fluorescence-lifetime imaging microscopy (FLIM) is an imaging technique for producing an image based on the differences in the exponential decay rate of the fluorescence from a fluorescent sample. It can be used as an imaging technique in confocal microscopy, two-photon excitation microscopy, and multiphoton tomography. The lifetime of the fluorophore signal, rather than its intensity, is used to create the image in FLIM. In some embodiments, FLIM is used to gain pH information, as one of the photo physical properties of the dyes that would change when the nucleic acid complex changes conformation due to a change in the pH. In some embodiments, the dye is an ATTO dye, BODIPY dye, ALEXA dye, TMR/TAMRA dye, or CV dye. Anisotropic imaging and FLIM are further described in Ekta Makhija, et al., "Probing Chromatin Structure and Dynamics Using Fluorescence Anisotropy Imaging" CRC Handbook, Imaging Biological Mechanics (2014) and Levitt et al., "Fluorescence lifetime and polarization-resolved imaging in cell biology" Current Opinion in Biotechnology, 2009, Vol. 20, Issue 1, p. 28-36, which are herein incorporated by reference for all purposes.

V. DISEASES DETECTION AND MONITORING

The methods, compositions, nucleic acids, and kits of the disclosure can be used for the detection of diseases, the monitoring of diseases, and as a drug screening platform. In some embodiments, the disease is characterized as a lysosomal dysfunction disease. In some embodiments, the pathology of the disease includes lysosomal dysfunction.

Lysosomal dysfunction diseases include, for example, autosomal recessive osteopetrosis, Farber disease, Krabbe disease (infantile onset and late onset), Fabry disease (Alpha-galactosidase A), Schindler disease (Alpha-galactosidase B), Sandhoff disease (infantile, juvenile, or adult onset), Tay-Sachs, juvenile hexosaminidase A deficiency, chronic hexosaminidase A deficiency, glucocerebroside, Gaucher disease (Type I, II, and III), lysosomal acid lipase deficiency (early onset and late onset), Niemann-Pick disease (Type A and B), sulfatidosis, metachromatic leukodystrophy (MLD), saposin B deficiency, multiple sulfatase deficiency, mucopolysaccharidoses: MPS I Hurler Syndrome, MPS I S Scheie Syndrome, MPS I H-S Hurler-Scheie Syndrome, Type II (Hunter syndrome), Type III (Sanfilippo syndrome), MPS III A (Type A), MPS III B (Type B), MPS III C (Type C), MPS III D (Type D), Type IV (Morquio), MPS IVA (Type A), MPS IVB (Type B), Type VI (Maroteaux-Lamy syndrome), Type VII Sly Syndrome, Type IX (Hyaluronidase Deficiency); Mucolipidosis: Type I (Sialidosis), Type II (I-cell disease), Type III (Pseudo-Hurler Polydystrophy/Phosphotransferase Deficiency), Type IV (Mucolipidin 1 deficiency); Niemann-Pick disease (Type C and D), Neuronal Ceroid Lipofuscinoses: Type 1 Santavuori-Haltia disease/Infantile NCL (CLN1 PPT1), Type 2 Jansky-Bielschowsky disease/Late infantile NCL (CLN2/LINCL TPP1), Type 3 Batten-Spielmeyer-Vogt disease/Juvenile NCL (CLN3), Type 4 Kufs disease/Adult NCL (CLN4), Type 5 Finnish Variant/Late Infantile (CLN5), Type 6 Late Infantile Variant (CLN6), Type 7 CLN7, Type 8 Northern Epilepsy (CLN8), Type 8 Turkish Late Infantile (CLN8), Type 9 German/Serbian Late Infantile (Unknown), Type 10 Congenital Cathepsin D Deficiency (CTSD); Wolman disease, alpha-mannosidosis, beta-mannosidosis, aspartylglucosaminuria, fucosidosis, lysosomal transport diseases, cystinosis, pycnodysostosis, salla disease/sialic acid storage disease, infantile free sialic acid storage disease (ISSD), glycogen storage diseases, Type II Pompe Disease, Type IIIb Danon disease, and cholesteryl ester storage disease. In some embodiments, the disease is autosomal recessive osteopetrosis. In some embodiments, the disease is Niemann-Pick C disease.

VI. KITS

The materials and components described for use in the methods may be suited for the preparation of a kit. Thus, the disclosure provides a detection kit useful for determining the pH and/or the presence, absence, or concentration of an analyte in a sample, cell or region thereof. Specifically, the technology encompasses kits for measuring the pH or analyte of one or more cells in a sample. For example, the kit can comprise a nucleic acid complex as described herein.

In some embodiments, the methods described herein may be performed by utilizing pre-packaged diagnostic kits comprising the necessary reagents to perform any of the methods of the technology. For example, such a kit would include a detection reagent for measuring the pH of a cell or region thereof. In one embodiment of such a kit, the detection reagents are the nucleic acid complexes of the disclosure. Oligonucleotides are easily synthesized and are stable in various formulations for long periods of time, particularly when lyophilized or otherwise dried to a powder form. In this form, they are easily reconstituted for use by those of skill in the art. Other reagents and consumables required for using the kit could be easily identified and procured by those of skill in the art who wish to use the kit. The kits can also include buffers useful in the methods of the technology. The kits may contain instructions for the use of the reagents and interpreting the results.

In some embodiments, the technology provides a kit comprising at least one sample (e.g., a pH standard) packaged in one or more vials for use as a control. Each component of the kit can be enclosed within an individual container and all of the various containers can be within a single package, along with instructions for performing the assay and for interpreting the results of the assays performed using the kit.

In some embodiments, the kit comprises a device for the measurement of pH and/or analytes in a sample. In some embodiments, the device is for measuring pH and/or analyte in cell culture or in whole, transparent organisms (e.g., *C. elegans*).

VII. EXAMPLES

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Rational Design of a Palette of Ultrasensitive DNA-Based Fluorescent pH Sensitive Nanodevices Described herein is a rational design to tune pH sensitivity of a DNA-based conformational switch, called the I-switch, to yield a palette of fluorescent pH sensitive nanodevices spanning pH values from 4.5 to 8.0. This new family of I-switches are the most sensitive pH sensors thus far in the literature showing unprecedented fold change covering the entire known range of physiological pH.

The availability of non Watson-Crick basepairing in DNA has led to the discovery of several functional DNA architectures which have been deployed in cellulo to yield insight on intracellular chemical environments (Y. Krishnan and M. Bathe, *Trends in Cell Biol.*, 2012, 22, 624-633 and Y. Krishnan and F. C. Simmel, *Angew. Chem. Int. Ed.* 2011, 50, 3124-3156). Cytosine rich DNA sequences are found in human genomes such as in telomeres and in promoters of several oncogenes e.g. c-myc(T. A. Brooks, S. Kendrick and L. M. Hurley, *FEBS Journal*, 2010, 277, 3459-3469 and T. Simonsson, M. Pribylova and M. Vorlickova, *Biochem. Biophys. Res. Commun.*, 2000, 278, 158-166). In 1993, Gueron and co-workers found that the DNA sequence d(C5T) can form a special tetraplex structure under slightly acidic condition where two parallel duplexes paired through C.CH+ pairs intercalated with each other in head to tail orientation called the i-motif (K. Gehring, J. L. Leroy and M. Gueron, *Nature* 1993, 363, 561-565 and T. E. Malliavin, J. Gau, K. Snoussi and J. L. Leroy, *Biophy. Journal*, 2003, 84, 3838-3847). It has applications as a pH reporter (Y. Chen, S. H. Lee and C. Mao, *Angew. Chem. Int. Ed.* 2004, 43, 5335-5338; Z. Liu and C. Mao, *Chem. Commun.*, 2014, 50, 8239-8241; and D. Liu, A. Bruckbauer, C. Abell, S. Balasubramanian, D. J. Kang, D. Klenerman and D. Zhou, *J. Am. Chem. Soc.*, 2006, 128, 2067-2071) in the context of synthetic DNA-based conformational switches (D. Liu and S. Balasubramanian, *Angew. Chem. Int. Ed.* 2003, 42, 5734-5736 and A. Idili, A. Vallee-Belisle and F. Ricci, *J. Am. Chem. Soc.* 2014, 136, 5836-5839), such as the I-switch, where an i-motif induced conformational change is transduced into a photonic output (H. Meng, Y. Yang, Y. Chen, Y. Zhou, Y. Liu, X. Chen, H. Ma, Z. Tang, D. Liu and L. Jiang, *Chem. Commun.*, 2009, 2293-2295) using FRET. Modi et al used I-switches to study the pH dynamics in endocytic organelles of living cells (S. Modi, C. Nizak, S. Surana, S. Halder and Y. Krishnan, *Nat. Nanotechol.*, 2013, 8, 459; S. Modi, M. G. Swetha, D. Goswami, G. D. Gupta, S. Mayor and Y. Krishnan, *Nat. Nanotechol.*, 4, 325-330; and S. Surana, J. M. Bhat, S. P. Koushika and Y. Krishnan, *Nat. Commun.*, 2011, 2, 1-7). There is evidence that the pH responsive regime of i-motif based conformational switches may be tuned by changing the number of cytosine in a stretch (J. L. Mergny, L. Lacroix, X. Han, J. L. Leroy and C. Hélène, *J. Am. Chem. Soc.*, 1995, 117, 8887-8898; S. Modi, S. Halder, C. Nizak and Y. Krishnan, *Nanoscale*, 2014, 6, 1144-1152; and I. V. Nesterova and E. E. Nesterova, *J. Am. Chem. Soc.*, 2014, 136, 8843-8846.) since cooperativity correlates directly with i-motif stability (E. M. Moody and P. C. Bevilacqua, *J. Am. Chem. Soc.*, 2003, 125, 16285-16293 and P. Buceka, R. Gargallob and A. Kudrev, *Analytica Chimica Acta*, 2010, 683, 69-77). The issue with such strategies has been that along with the increase in midpoint of the pH-induced structural transition ($pH_{half}$) the increased cooperativity of the transition substantially narrows the overall pH sensitive regime. While a better pH resolution over a narrower pH regime can be useful in certain contexts, it is much more beneficial to alter the $pH_{half}$ without increasing cooperativity. This example describes a strategy to alter the pH sensitive regime of I-switches while maintaining the number of cytosines constant (n=4, 14), without changing the cooperativity of the pH induced transition.

Cytosine hemiprotonation drives i-motif formation. The $pK_a$ of Cytosine N3 is ~4.5 and thus $DNA_4$ i-motifs are maximally stabilized at ~pH 5.0 (J. L. Leroy, M. Gueron, J. L. Mergny and C. Hélène, *Nucleic Acids Res.*, 1994, 22, 1600-1606). This typically results in I-switches with pH reporting capacity at 5.5<pH<7.0. However, different intracellular organelles maintain a different resting pH that varies from pH 4.5 (lysosomes) to pH 8.0 (mitochondria) and thus, there is a need to engineer I-switches which can respond to the whole physiological range. It was hypothesized that introduction of chemically modified cytosines (N. K. Sharma and K. N. Ganesh, *Chem. Commun.*, 2005, 4330-4332; B. Datta, M. E. Bier, S. Roy and B. A. Armitage, j. *Am. Chem. Soc.*, 2005, 127, 4199-4207; A. Pasternak and J. Wengel, *Bioorg. Med. Chem. Lett.*, 2011, 21, 752-755; A. Pasternak and J. Wengel, *Org. Biomol. Chem.*, 2011, 9, 3591-3597; and P. Perlkov, K. K. Karlsen, E. B. Pedersen and J. Wengel, *Chembiochem.*, 2014, 15, 146-156) with lower or higher pKa such as 5'-Bromocytosine (pKa~2.5) or 5'-Methylcytosine (pKa-9.1) (T. Kulikowski and D. Shugar, *Acta Biochem. Polonica*, 1979, 26, 145-160) could accordingly tune I-switch response by altering the $pH_{half}$ of the structural transition without altering the cooperativity. Applicants observed that fully-brominated or fully-methylated cytosines in 14 failed to form i-motifs at room temperature. Thus, 14 was doped with cytosine modifications at specific positions while keeping the total number of modified cytosines per I-switch constant (N=4) to see if this could alter the $pH_{half}$ of the structural transition. The new family of I-switches incorporates a stretch of four, pH sensitive, C-rich segment $(C_4TAA)_3C_4$ (SEQ ID NO. 15) that forms a mismatched duplex at neutral or basic pH with a partially complementary G-rich strand (TTTGTTATGTGT-TATGTGTTAT) (SEQ ID NO. 16), where T indicates mismatches. In this I-switch design, the C-rich segment bears (FIG. 1A) a donor fluorophore (ALEXA 488) and the mismatched duplex positions an acceptor fluorophore (ALEXA 647) far apart. At acidic pH, the mismatched duplex frays as the C-rich strand forms an i-motif, bringing the two fluorophores into a high FRET conformation that may be monitored by fluorescence spectroscopy. The perfect duplex domain (black) harbors a binding site for a recombinant antibody to enable targeting. FIGS. 1B & C shows only the i-motif domain of the I-switch where only the cytosine residues are represented as triangles, the apices of the triangles pointing towards the 3' end of the strand. The grey triangles represent unmodified cytosines while the asterisk (*) represent sites that incorporate either 5'-Bromocytosines (Br I-switches, red triangles) or 5'-Methylcytosines (Me I-switches, blue triangles) respectively in the modified I-switches. FIG. 1C shows four classes of modified I-switches categorized on the basis of their relative positions in the i-motif domain of the I-switch. The first class incorporates either two all-bromo or two all-methyl modified $C_m$—$H^+$—$C_m$ base pairs at positions 3, 9, 17, 23 that lie at the core of the resultant i-motif (Core) with the reasoning that these could possibly affect the nucleation event for i-motif formation. The second class incorporates either two all-bromo or two all-methyl modifications at the peripheral $C_m$—$H^+$—$C_m$ base pairs at positions 1, 11, 15, 25 (End) with the reasoning that these could modulate i-motif fraying and thereby stability to possibly shift the pH responsive regime (N. Kumar, M. Petersen and S. Maiti, *Chem. Commun.*, 2009, 1532-1534). In the Core and End designs, the i-motifs have two modified $C_m$—$H^+$—$C_m$ base-pairs on adjacent stacks. Applicants therefore sought to modulate pH of responsivity differently by interspersing two modified $C_m$—$H^+$—$C_m$ base pairs between unmodified C—$H^+$—C base pairs. Applicants therefore introduced modifications at positions 15, 17, 23, 25 to yield the Interspersed variant shown in FIG. 1C. All these variants have two all-bromo or all-methyl modified $C_m$—$H^+$—$C_m$ base-pairs in different topologies. Applicants then sought to modulate $pH_{1/f}$ by instead incorporating four hemi-modified $C_m$—$H^+$—C base pairs, by modifying only one of the participating cytosines of a C—$H^+$—C base pair. Applicants did this by introducing modifications on four consecutive cytosines at positions 1, 2, 3, 4 at the 5' end (Consecutive).

First, it was confirmed that formation of i-motifs at acidic pH by all the I-switch variants used in this study by monitoring the difference in Circular Dichroism (CD) spectra between pH 5.0 and pH 8.5 from 220 nm-320 nm (FIG. 7). The difference spectra of pH 5.0 and pH 8.5 showed a positive band centered around 292 nm, and a negative band centered around 260 nm (R. Z. Jin, K. J. Breslauer, R. A. Jones and B. L. Gaffney, *Science*, 1990, 250, 543-546). This type of spectrum is attributed to the formation of C—$H^+$—C base pairs (E. L. Edwards, M. H. Patrick, R. L. Ratliff and D. M. Gray, *Biochemistry*, 1990, 29, 828-836), characteristic of the i-motif structure (H. Kanehara, M. Mizuguchi, K. Tajima, K. Kanaori, and K. Makino, *Biochemistry*, 1997, 36, 1790-1797 and M. Kaushik, N. Suehl and L. A. Marky, *Biochemistry*, 2007, 126, 154-164). The pH dependent structural transition of the new I-switches (Br I-switches and Me I-switches) was confirmed using CD spectroscopy at different pH (FIGS. 2A & B). The change in molar ellipticity was normalized from 0 to 1 and was plotted as a function of pH at 292 nm, where the C—$H^+$—C basepairs are known to absorb maximally. As the pH increases, the structural transition from i-motif structure to duplex DNA occurs, hence, positive band at 292 nm decreases sigmoidally due to the decrease in C—$H^+$—C base pairs reflecting the pH induced denaturation. The different Br modified switches namely Interspersed, Core, End and Consecutive showed a $pH_{half}$ of structural transition at pH 6.6, 7.3, 6.2 and 6.8 respectively while the different Me modified switches namely Interspersed, Core, End and Consecutive showed $pH_{half}$ at pH 6.8, 7.0, 6.9 and 7.0 respectively while 14 showed a $pH_{half}$ at pH 6.5. This change in $pH_{half}$ of the modified switches from the native 14 (pH 6.5) suggests the possible pH tuning of the I-switches containing modified cytosines. Note that though the magnitude of changes in $pH_{half}$ is rather muted, as it is known that this is not highly sensitive to capture the overall pH sensitive regime and serves merely as a positive indicator that the i-motif stability is tunable by this method (M. M. Dailey, M. C. Miller, P. J. Bates, A. N. Lane and J. O. Trent, *Nucleic Acids Res.* 2010, 38, 4877-4888). To investigate the actual pH responsivity and performance of these modified I-switches Applicants proceeded to investigate the pH-induced transition by fluorescence resonance energy transfer (FRET) using I-switch variants bearing donor and acceptor fluorophores as shown in FIG. 1.

At basic pH the labels are held far apart by a mismatched duplex showing low FRET and high D/A values, while at acidic pH the i-motif domains shorten the distances between the two fluorophores showing high FRET and consequently low D/A values. The dually labeled I-switch variants (1× clamping buffer of desired pH, 120 mM KCl, 5 mM NaCl, 20 mM HEPES, 1 mM $CaCl_2$ and 1 mM $MgCl_2$) were excited at 495 nm and emission spectra were collected from 505 nm to 725 nm. Emission intensity at 520 nm from ALEXA 488 (D) was divided by emission intensity at 669 nm from ALEXA 647 (A) to obtain D/A ratios at various pH which was then normalized to pH 4.0 and plotted as a function of pH (FIGS. 2C & D). This gives the characteristic pH responsive regime and pH sensitivity of the given I-switch variant. The change in D/A ratios was a result of both decrease in ALEXA 488 intensity and increase in the ALEXA 647 intensity due to FRET (FIG. 8) yielding a characteristic sigmoidal curve. The $pH_{half}$ of $I^4_{488/647}$ and $I^7_{488/647}$ were pH 6.1 and 7.3 respectively while the Br I-switch variants namely Interspersed, Core, End and Consecutive showed their $pH_{half}$ value by FRET to be at pH 6.6, 5.6, 6.3 and 6.8 respectively. The Me I-switch variants Interspersed, Core, End and Consecutive showed $pH_{half}$ values corresponding to 6.8, 7.1, 6.9 and 6.7 respectively (Table 1, FIG. 8). Relative to unmodified 14, with the Br I-switch variants we observed a shift in the $pH_{half}$ towards a more acidic range and with the Me I-switch variants this was towards a more basic range as predicted. Importantly, the cooperativity both Br-modified and Me-modified switches remained conserved compared to $I^4_{A488/A647}$ (Table 1).

| Switch[a] | $pH_{half}^D$ | Fold Change[c] | Cooperativity[a] |
|---|---|---|---|
| Interspersed | 6.6 ± 0.04 | 12.5 | 2.4 |
| Core | 5.6 ± 0.07 | 7.5 | 2.2 |
| End | 6.3 ± 0.03 | 10 | 2.0 |
| Consecutive | 6.8 ± 0.08 | 10.1 | 3.1 |
| Interspersed | 6.8 ± 0.26 | 8.6 | 2.1 |
| Core | 7.1 ± 0.18 | 7.8 | 3.3 |
| End | 6.9 ± 0.06 | 14 | 3.2 |
| Consecutive | 6.7 ± 0.06 | 8.0 | 3.3 |
| I4 | 6.1 ± 0.2 | 4.1 | 2.2 |
| I7 | 7.3 ± 0.04 | 3.5 | 6.3 |

Contrast Me-$I_4$ Core that shows a $pH_{half}$ of 7.1 and a sensitive regime of pH 6.2-7.5 with $I^7_{A488/A647}$ with an $pH_{half}$ of 7.0, that due to its high cooperativity shows a very narrow dynamic range of pH 7.0-pH 7.5, thus indicating the success of this design strategy. As a result, the new family of I-switches can probe the same breadth of pH as seen in 14, while covering a different regime of pH as seen in 17 (FIG. 3). It was further observed that End variants have the maximum intended effect in shifting the dynamic range of an I-switch. Cumulatively, this study demonstrates that I-switches may be tuned by base modification to achieve a wider and varied dynamic range without compromising the cooperativity and hence stability.

In summary, this example describes the characterization of a family of I-switches whose pH responsive regimes have been successfully tuned using 5'-Bromocytosines (pKa ~2.5) towards more acidic range and 5'-Methylcytosines (pKa ~9.1) towards more basic range without compromising dynamic range due to altered cooperativity. Importantly both Br I-switches and Me I-switches showed tremendously high fold change in D/A ratio. Fold change in D/A ratio is an indicator of the sensitivity of the pH reporter, where the higher the fold change, the greater the sensitivity and greater the resolution of the pH reported. Interestingly, such dramatic fold change as shown by the current family of I-switches is unprecedented in any known ratiometric pH sensor based on any molecular scaffold. The enhancement in fold change in D/A ratio of the modified switches over the unmodified I-switches i.e., $I^4_{A488/A647}$ and $I^7_{A488/A647}$ switch (Table 1) enables the measurement of pH over a wide range of pH with a resolution that is better than even the high-cooperativity I-switches that are restricted to a narrow pH regime (such as $I^7_{A488/A647}$). Also, this example describes for the first time, the formation of I-motifs at basic pH (pH>7.1) at room temperature.

The following describes materials and methods used in this example.

All unlabeled oligonucleotides were obtained from Sigma-Aldrich (India), while labeled oligonucleotides were obtained from IBA-GmbH (Germany) as high performance liquid chromatography (HPLC) purified and lyophilized. Oligonucleotides were dissolved in Milli-Q water to make 200 μM stock, which was aliquoted and kept at −20° C. Fluorescently labelled oligonucleotides, depending on their purity of fluorescently labeled oligonucleotides, were subjected to ethanol precipitation prior to use to remove any contaminating fluorophores.

I-switch sample preparation: I-switch samples were prepared by mixing 5 μM of $I^n$ and $I^n$ comp in equimolar ratios in 20 mM potassium phosphate buffer of pH 5.5 containing 100 mM KCl. The sample was heated to 90° C. for 5 minutes, cooled to room temperature (RT) at 5° C./15 min and equilibrated at 4° C. overnight. Prior to experiments, the stock solution was diluted in appropriate 1× clamping buffer (120 mM KCl, 5 mM NaCl, 20 mM HEPES, 1 mM CaCl$_2$ and 1 mM MgCl$_2$) of desired pH.

Circular dichroism spectroscopy studies: All circular dichroism (CD) experiments were performed on a JASCO J-815 spectrophotometer (JASCO, USA) equipped with a temperature controller. Prior to the experiment, I-switch samples were diluted to 1 μM in 1× clamping buffer of desired pH (120 mM KCl, 5 mM NaCl, 20 mM HEPES, 1 mM CaCl$_2$ and 1 mM MgCl$_2$) and equilibrated for 60 minutes at room temperature. The spectra were acquired in 1 cm quartz cuvette containing 400 μL of 1 μM of sample. CD spectra were recorded from 320 nm to 220 nm with 1 nm bandwidth with a scanning speed of 100 nm/second and a response time of 0.25 second. An average of 3 successive scans was acquired and subtracted from a baseline corresponding to buffer alone. CD signal at 292 nm at different pH values was recorded and normalized to 0-1 by taking CD signal at closed state as $Y_{max}$ and CD at open state as $Y_{min}$ and using formula [Y−Ymin]/[Ymax−Ymin] in OriginPro 8 (OriginLabs, USA). Mean of CD signal at 292 nm from two independent experiments and their standard error of mean were plotted for each pH value to obtain a normalized ellipticity (Θ) v/s pH plot for each I-switch sample. The CD spectra at pH 5.0 showing a peak between 286-288 nm and a negative peak around 248-251 nm confirmed the formation of i-motif for different I-switches. The difference CD spectra of pH 5.0 and pH 8.5 showed a positive peak around 292 nm, which is characteristic of an i-motif.

Fluorescence spectroscopic studies: For fluorescence measurements, fluorescently labeled I-switch samples were diluted to 50 nM using 1× clamping buffer of the required pH (120 mM KCl, 5 mM NaCl, 20 mM HEPES, 1 mM CaCl$_2$ and 1 mM MgCl$_2$). All samples were vortexed and equilibrated for 60 minutes at RT. Experiments were performed in a fluorescence cuvette with 1 cm path length containing 400 μL of each sample at different pH. Samples were excited at 495 nm in a FluoroMax-4 (Horiba Jobin Yvon, USA) and emission spectra were collected from 505 nm to 725 nm. Emission at 520 nm (donor, D) was then divided by emission at 669 nm (acceptor FRET, A) to obtain D/A ratios at various pH values. The D/A ratios at different pH points were then normalized to D/A at pH 4.0 An in vitro pH calibration curve was obtained by plotting the normalized ratio of donor intensity (D) at 520 nm by acceptor intensity (A) at 669 nm as a function of pH. Mean of D/A from three independent experiments and their standard error of mean were plotted for each pH value.

Determination of pH$_{half}$: Plots of normalized D/A v/s pH for each I-switch were fitted using a Boltzmann distribution in OriginPro 8. The sample curve and the formula used for fitting were: $y=[(A_1-A_2)/1+e^{(x-x_0)/dx}]+A_2$; where: $A_1$=initial value; $A_2$=final value; $x_0$=midpoint of the curve (pH$_{half}$); and dx=time constant (FIG. 4). The corresponding pH$_{half}$ for each I-switch sample was obtained and reported in Table 1.

Determination of cooperativity: Cooperativity was determined by fitting plots of normalized D/A values v/s pH for each I-switch using DoseResponse curve in OriginPro 8. The sample curve and the formula used for fitting are as follows: $y=A_1+[(A_2-A_1)/1+10^{(\log\ x0-x)p}]$ where: $A_1<A_2$; p>0; bottom asymptote: $A_1$=1; top asymptote: $A_2$=2; centre: log $x_0$; Hill slope: p=cooperativity (FIG. 5). The corresponding cooperativity value was obtained and reported in Table 1.

Oligonucleotides, and their corresponding nomenclature used in this study. I-switch samples incorporating a pH responsive segment Cn-Cn-Cn-Cn is referred to as $I^n$ (n=4 or 7) when they carry no base modification and fluorescent labels. Thus, $I^4$ was formed by mixing a 1:1 mmolar ratio of $I^4$ and $I^4$ comp, $I^7$::$I^7$ and $I^4$ comp, Interspersed:: Interspersed and $I^4$ comp, Core:: Core and $I^4$ comp, End:: End and $I^4$ comp, Consecutive:: Consecutive and $I^4$ comp. Fluorescently labeled I-switch assemblies for fluorescent studies indicate the respective fluorophore in the subscript, by mixing 1:1 molar ratio of the two strand, where, e.g., $I^4_{A488/A647}$ was formed from mixing 1:1 molar ratio of $I^4_{A488}$ and $I^4_{A647}$ comp, $I^7_{A488/A647}$:: $I^7_{A488}$ and $I^4_{A647}$ comp. Modified 1-switches for fluorescence studies were made by mixing 1:1 molar ratio of the two labelled strands, using respective 5'ALEXA 488 labeled sequence and $I^4_{A647}$ comp e.g., dually labelled Interspersed was formed by 5'ALEXA 488 labeled Interspersed strand and $I^4_{A647}$ comp, Core:: 5'ALEXA 488 labeled Core strand and $I^4_{A647}$ comp, End:: 5'ALEXA 488 labeled End strand and $I^4_{A647}$ comp, Consecutive:: 5'ALEXA 488 labeled Consecutive strand and $I^4_{A647}$ comp.

| Name | Sequence | Modification |
|---|---|---|
| $I^4$ | 5'-CCCCTAACCCCTAACCCCTAACCCCATATATATCCTAGAACGACAGA CAAACAGTGAGTC-3' (SEQ ID NO. 17) | — |
| $I^7$ | 5'-CCCCCCCTAACCCCCCCTAACCCCCCCTAACCCCCCCATATATATCC TAGAACGACAGACAAACAGTGAGTC-3' (SEQ ID NO. 18) | — |

| Name | Sequence | Modification |
|---|---|---|
| I⁴ comp | 5'-GACTCACTGTTTGTCTGTCGTTCTAGGATATATATTTTGTTATGTGT TATGTGTTAT-3' (SEQ ID NO. 19) | — |
| I⁴_A488 | 5'-CCCCTAACCCCTAACCCCTAACCCCATATATATCCTAGAACGACAGA CAAACAGTGAGTC-3' (SEQ ID NO. 20) | 5' ALEXA 488 labeled |
| I⁷_A488 | 5'-CCCCCCCTAACCCCCCCTAACCCCCCCTAACCCCCCCATATATATCC TAGAACGACAGACAAACAGTGAGTC-3' (SEQ ID NO. 21) | 5' ALEXA 488 labeled |
| I⁴_A647 comp | 5'-GACTCACTGTTTGTCTGTCGTTCTAGGATA<u>T</u>ATATTTTGTTATGTGT TATGTGTTAT-3' (SEQ ID NO. 22) | <u>T</u> labeled with ALEXA 647 |

Br modified switches for CD spectroscopy

| Name | Sequence | Modification |
|---|---|---|
| Interspersed | 5'-CCCCTAACCCCTAAC*CC*CTAACC*CC*ATATATATCCTAGAACGA CAGACAAACAGTGAGTC-3' (SEQ ID NO. 23) | C* are 5'-Bromocytosines |
| Core | 5'-CCC*CTAACC*CCTAACCC*CTAACC*CCATATATATCCTAGAACGA CAGACAAACAGTGAGTC-3' (SEQ ID NO. 24) | C* are 5'-Bromocytosines |
| End | 5'-C*CCCTAACCCC*TAAC*CCCTAACCCC*ATATATATCCTAGAACGA CAGACAAACAGTGAGTC-3' (SEQ ID NO. 25) | C* are 5'-Bromocytosines |
| Consecutive | 5'-C*C*C*C*TAACCCCTAACCCCTAACCCCATATATATCCTAGAACGA CAGACAAACAGTGAGTGC-3' (SEQ ID NO. 26) | C* are 5'-Bromocytosines |

Br modified switches for fluorescence spectroscopy

| Name | Sequence | Modification |
|---|---|---|
| Interspersed | 5'-CCCCTAACCCCTAAC*CC*CTAACC*CC*ATATATATCCTAGAACGA CAGACAAACAGTGAGTC-3' (SEQ ID NO. 27) | 5' ALEXA 488 labeled and C* are 5'-Bromosytosines |
| Core | 5'-CCC*CTAACC*CCTAACCC*CTAACC*CCATATATATCCTAGAACGA CAGACAAACAGTGAGTC-3' (SEQ ID NO. 28) | 5' ALEXA 488 labeled and C* are 5'-Bromosytosines |
| End | 5'-C*CCCTAACCCC*TAAC*CCCTAACCCC*ATATATATCCTAGAACGA CAGACAAACAGTGAGTC-3' (SEQ ID NO. 29) | 5' ALEXA 488 labeled and C* are 5'-Bromosytosines |
| Consecutive | 5'-C*C*C*C*TAACCCCTAACCCCTAACCCCATATATATCCTAGAACGA CAGACAAACAGTGAGTC-3' (SEQ ID NO. 30) | 5' ALEXA 488 labeled and C* are 5'-Bromosytosines |

Methyl modified switches for CD spectroscopy

| Name | Sequence | Modification |
|---|---|---|
| Interspersed | 5'-CCCCTAACCCCTAAC*CC*CTAACC*CC*ATATATATCCTAGAACGA CAGACAAACAGTGAGTC-3' (SEQ ID NO. 31) | C* are 5'-Methylcytosines |
| Core | 5'-CCC*CTAACC*CCTAACCC*CTAACC*CCATATATATCCTAGAACGA CAGACAAACAGTGAGTC-3' (SEQ ID NO. 32) | C* are 5'-Methylcytosines |
| End | 5'-C*CCCTAACCCC*TAAC*CCCTAACCCC*ATATATATCCTAGAACGA CAGACAAACAGTGAGTC-3' (SEQ ID NO. 33) | C* are 5'-Methylcytosines |
| Consecutive | 5'-C*C*C*C*TAACCCCTAACCCCTAACCCCATATATATCCTAGAACGA CAGACAAACAGTGAGTC-3' (SEQ ID NO. 34) | C* are 5'-Methylcytosines |

Methyl modified switches for fluorescence spectroscopy

| Name | Sequence | Modification |
|---|---|---|
| Interspersed | 5'-CCCCTAACCCCTAAC*CC*CTAACC*CC*ATATATATCCTAGAACGA CAGACAAACAGTGAGTC-3' (SEQ ID NO. 35) | 5' ALEXA 488 labeled and C* are 5'-Methylcytosines |
| Core | 5'-CCC*CTAACC*CCTAACCC*CTAACC*CCATATATATCCTAGAACGA CAGACAAACAGTGAGTC-3' (SEQ ID NO. 36) | 5' ALEXA 488 labeled and C* are 5'-Methylcytosines |
| End | 5'-C*CCCTAACCCC*TAAC*CCCTAACCCC*ATATATATCCTAGAACGA CAGACAAACAGTGAGTC-3' (SEQ ID NO. 37) | 5' ALEXA 488 labeled and C* are 5'-Methylcytosines |
| Consecutive | 5'-C*C*C*C*TAACCCCTAACCCCTAACCCCATATATATCCTAGAACGA CAGACAAACAGTGAGTC-3' (SEQ ID NO. 38) | 5' ALEXA 488 labeled and C* are 5'-Methylcytosines |

In vitro characterization of various modified I-switches using CD spectroscopy: In vitro folding of the I-switch was characterized using CD spectroscopy. CD spectra taken at pH 5.0 showed a positive band centered at 285-288 nm and a negative band centered at 248-251 nm characteristic of an i-motif. However, at pH 8.5, the same assembly showed a CD spectrum where the positive and negative bands shifted to 275-277 nm and 242-246 nm, respectively. The difference spectrum of the DNA assembly at pH 5.0 and pH 8.5 gave a trace that showed a positive band centered at 292 nm and a negative band centered at 260 nm (FIG. 7A-H) which is consistent with the CD signature characteristic of DNA₄ i-motifs.[1] This type of spectrum is attributed to the formation of C—CH⁺ base pairs, characteristic of i-motif structure.[2]

The pH dependent structural transition of the DNA I-switches (Br modified switches and Me modified Switches) was confirmed using CD spectroscopy at different pH values.

The DNA i-motif forms due to hemiprotonation of cytosine residues. N3 of Cytosine has a pKa of ~4.5, which makes it possible to form i-motif at acidic pH (~5.5). To tune the pH sensing properties of i-motif based I-switches, specific cytosine residues were replaced with 5'-bromocytosines (pKa ~2.5) or 5'-methylcytosines (pKa ~9.1). The pH profile of the assemblies were investigated by measuring the change in CD signal as a function of pH. As the pH increases, the structural transition from closed i-motif structure to duplex structure occurs, hence, the number of C—CH$^+$ bases decreases resulting in a corresponding decrease in CD signal. Different Br modified switches namely interspersed, core, end and consecutive showed a pH$_{half}$ of structural transition at pH 6.6, 7.3, 6.2 and 6.8, respectively. Different Me modified switches, on the other hand, showed pH$_{half}$ at pH 6.8, 7.0, 6.9 and 7.0, respectively, while I$^4$ showed a pH$_{half}$ at pH 6.5. This change in pH$_{half}$ of the modified switches from the native I$^4$ clearly suggests tuning the pH regime of i-motif formation due to modified cytosines. A plot of the CD signal at 292 nm as a function of pH yielded an inverse sigmoidal curve indicating a pH dependent structural transition. This clearly demonstrates tunability of pH sensitivity of I-switches.

In vitro characterization of I-switches using fluorescence spectroscopy: All the I-switches contain four C-rich segments, each of which, in turn, contains four cytosine residues, $(C_4TAA)_3C_4$ that is base paired to form a mismatched duplex with a complementary G-rich strand. In the design of the I-switch, at neutral and basic pH, both C-rich and G-rich strands form a mismatched duplex keeping the donor fluorophore (ALEXA 488) and acceptor fluorophore (ALEXA 647) at distances which are non-optimal for FRET. At acidic pH, the mismatched duplex dissociates, allowing the C-rich strand to fold into an i-motif, bringing the two fluorophores into close proximity, thus enabling FRET. This structural transition was monitored using pH-dependent fluorescence measurements. Dually labeled I-switches were assembled as described previously and then diluted to 50 nM in 1× clamping buffer of desired pH. The sample was then excited at 495 nm and emission spectra acquired from 505 nm to 725 nm. The emission at 520 nm (donor) is then divided by emission at 669 nm (FRET acceptor) to obtain D/A. The D/A ratios were then normalized to D/A at pH 4.0 and a plot of normalized D/A v/s pH was obtained. The emission spectra at pH 5.0 and pH 8.5 clearly show a decrease in the donor emission intensity and a corresponding increase in FRET acceptor intensity with the increase in acidity of the solution (FIG. 8A-H).

Determination of pH$_{half}$ for the I-switches: The normalized D/A v/s pH plot for individual I-switches was fitted using a Boltzmann curve. The fit is obtained using the following formula: $y=[(A1-A2)/1+e(x-x0))/dx]+A2$; where: A1=initial value; A2=final value; x0=midpoint of the curve (pHhalf) and dx=time constant. The value given by the factor x0 gives the value of the pHhalf for all the switches. Two representative examples are noted in FIG. 9A-B.

Determination of cooperativity for the modified I-switches: The normalized D/A v/s pH plot obtained for individual I-switches was fitted using a DoseResponse curve. The fit is obtained using the following formula: $y=A_1+[(A_2-A_1)/1+10^{(\log x0-x)p}]$; where: $A_1<A_2$; $p>0$; bottom asymptote: $A_1=1$; top asymptote: $A_2=2$; centre: log $x_0$; where Hill slope: p=cooperativity (FIG. 10).

Example 2: Combination pH and Chloride Sensor

A. The Instant pH Sensors I4$^{LY}$ (Br Modified Switch—End) Accurately Measure pH in Lysosomes of Whole Transparent Organisms Such as C elegans.

The lysosomes of coelomocytes of C elegans were labeled using a protocol described in the literature (Surana, S., et al., 2011. An autonomous DNA nanomachine maps spatiotemporal pH changes in a multicellular living organism. Nature Communications 2, p. 340) as well as in Materials and Methods below. Older versions of I-switches could capture only large changes in pH—such as going from early endosome to late endosome to lysosome. These had insufficient accuracy to capture minor pH changes occurring around a given pH range as seen between a normal organelle and dysfunctional organelle, especially in the more acidic regime. Now, with the newly described bromo-I-switches, such as I4$^{LY}$, the pH regimes covered are in the more acidic regime and the heightened fold change in D/A allows accurate measurement of minor changes in pH in the lysosome.

B. Use of this Protocol to Make Measures of Other Ions as Well, Such as Chloride, Using a DNA-Based Chloride Sensor, Clensor, in the Lysosomes of C elegans.

The inventors used a previously described DNA-chloride sensor, Clensor, that has been used to make the first measure of chloride in the lysosome of cultured cells, to measure chloride in the lysosome of C elegans. It is not a straightforward extrapolation of the imaging procedure in cells, as the imaging conditions were modified (see, for example Materials and Methods below) so that the imaging could be done in whole, live, organisms such as C. elegans. This is consequently the first measurement of chloride in a living organism. FIGS. 11C and 11D show that the performance of Clensor under these imaging conditions is quantitatively preserved from in vitro solutions in buffers of various chloride concentrations, to in vivo (in coelomocyte lysosomes in C elegans).

C. Demonstration that In Vivo Lysosomal pH Levels Show a One-to-One Correlation with Lysosomal Disorder Severity.

FIG. 11E shows the pH values obtained in lysosomes of wild type C elegans and mutants for a lysosomal storage disorder characterized by defective pH (Niemann Pick C disease). Niemann Pick C disease is characterized by cholesterol accumulation that leads to premature death, with affected individuals frequently dying in adolescence or earlier. In humans, the most commonly mutated genes are NPC1 and NPC2. Lysosomes are responsible for concentrating up cholesterol from the extracellular mileu and distributing it to the cytosol and ER membranes. In the lysosomal mileu NPC2 binds cholesterol and transfers it to the membrane bound NPC1. OSBPL5 that functions as an oxysterol protein reversibly associates with the lysosomal membrane from the cytoplasmic side. NPC1 transfers its bound cholesterol to OSBPL5 for distribution. C elegans has two homologs for NPC1 (ncr1 and ncr2) one homolog for NPC2 (heh1) and one homolog for OSBPL5 (obr3). Knocking down ncr1, heh1 and obr3 resulted in dramatic alkalinization of the lysosome (FIG. 11E). However, knocking down ncr2 showed no such alkalinization indicating that ncr1 is the only homolog that is functionally linked to a Niemann Pick C phenotype. Further, heh1, ncr1 and obr3 mutants showed cholesterol accumulation (FIG. 11F) and premature lethality (not shown), phenocopying the disease. An unrelated oxysterol binding protein such as obr2 when knocked out showed no pH change and no cholesterol accumulation. This indicates that pH levels indicated by the I4$^{LY}$ quantitatively measure lysosome dysfunction in vivo.

D. Demonstration that In Vivo Lysosomal Chloride Levels Show a One-to-One Correlation with Lysosomal Disorder Severity.

FIG. 11E shows the chloride values obtained in lysosomes of wild type *C elegans* and mutants for a lysosomal disorder characterized by defective chloride (autosomal recessive osteopetrosis, ARO). ARO is characterized by excessively dense bones that are due to dysfunctional lysosomes in bone-degrading cells called osteoclasts. In humans, the most commonly mutated genes are TCIRG-1 (~53%), CLCN7 (~15%), OSTM1 (~6%), and SNX10 (~4%). TCIRG-1 is a proton pump that acidifies the lysosome. These protons are exchanged for chloride by the chloride channel CLCN7 along with its accessory factor OSTM1. SNX10 is a SNARE protein responsible for transporting the lysosome to the cell membrane where it serves to create the "ruffled border" that characterizes osteoclasts. The *C elegans* has a homolog for TCIRG-1 (unc32), CLCN7 (clh6), SNX10 (snx3) and OSTM1 (ostm1). Knocking down clh6 and ostm1 resulted in dramatic decrease of lysosomal chloride (FIG. 1F). Next, chloride levels in two different mutants of unc32, i.e., unc32f that showed mild impairment of unc32 (a hypomorph) or unc32c, a non-functional mutation of unc32. Interestingly, chloride levels were more drastically affected in unc32c and moderately affected in the hypomorph unc32f. Importantly in the mutant snx3, no change in chloride was seen. Here it is important to note that snx3 is involved in lysosomal transport to create a functional osteoclast, not to create a specific lysosomal lumenal environment. Thus in these mutants, while the lysosome can be functional, the osteoclast is non-functional due to the lack of a ruffled border. Chloride values in the snx3 mutant are thus normal. As another control, knocking down clh4, which is a plasma membrane chloride channel showed no such chloride decrease indicating that clh6 is the channel that is functionally linked to genes that cause ARO. This indicates that chloride levels indicated by the I4$^{LY}$ quantitatively measure lysosome dysfunction in vivo.

E. Materials and Methods.

Materials. All fluorescently labeled oligonucleotides were HPLC-purified and obtained from IBA-GmBh (Germany) and IDT (Coralville, Iowa, USA). Unlabeled oligonucleotides were purchased from IDT (Coralville, Iowa, USA). The peptide nucleic acids (PNA) oligomer, P was synthesized using standard solid phase Fmoc chemistry on Nova Syn® TGA resin (Novabiochem, Germany) using analytical grade reagents (Applied Biosystems®, USA), purified by reverse phase HPLC (Shimadzu, Japan) and stored at −20° C. until further use.

Bovine serum albumin (66 kDalton), nigericin, valinomycin, monensin, chloride ionophore I, IPTG and cholesterol were obtained from Sigma (USA). All other reagents were purchased from Sigma-Aldrich (USA) unless otherwise specified. BSA was maleylated according to a previously published protocol.(Ref) Trizol was purchased from Invitrogen (U.S.A.).

Sample preparation. All oligonucleotides were ethanol precipitated and quantified by their UV absorbance. For I-switch (I4$^{ax}$ (also referred to as TLC)$_{A4488/A4647}$—Br modified "end" I4-switch) sample preparation, 5 µM of 14 and 14' were mixed in equimolar ratios in 20 mM potassium phosphate buffer, pH 5.5 containing 100 mM KCl. The resulting solution was heated to 90° C. for 5 minutes, cooled to the room temperature at 5° C./15 min and equilibrated at 4° C. overnight. Samples were diluted and used within 7 days of annealing. A sample of Clensor was similarly prepared using HPLC purified oligonucleotides and PNA oligomer at a final concentration of 10 µM by mixing D1, D2 and P in equimolar ratio in 10 mM sodium phosphate buffer, pH 7.2 and annealed as described above. Prior to use, all buffer stock solutions were filtered using 0.22 µm disk filters (Millipore, Germany).

*C. elegans* methods and strains. Standard methods were followed for the maintenance of *C. elegans*. Wild type strain used was the *C. elegans* isolate from Bristol (strain N2). Strains used in the study, provided by the *Caenorhabditis* Genetics Center (CGC), are heh-1(ok603), clh-6(ok791), unc-32(f131), unc-32(e189), ppk-3(n2835), gba-3(gk3287), ppt-1(gk139), and cln-3.2(gk41) I; cln-3.3(gkl18) cln-3.1 (pk479). Transgenics used in this study, also provided by the CGC, are arIs37 [pmyo-3::ssGFP], a transgenic strain that expresses ssGFP in the body wall muscles, which is secreted in the pseudocoelom and endocytosed by coelomocytes and pwIs50 [lmp-1::GFP+Cb-unc-119(+)], a transgenic strain expressing GFP-tagged lysosomal marker LMP-1. Genes for which mutants were unavailable were knocked down using Ahringer library based RNAi methods described in the following section.

RNAi experiments. Bacteria, from the Ahringer RNAi library, expressing dsRNA against the relevant gene was fed to worms, and measurements were carried out in one-day old adults of the F1 progeny (ref). RNA knockdown was confirmed by probing mRNA levels of the candidate gene, assayed by RT-PCR. Briefly, total RNA was isolated using the Trizol-chloroform method; 2.5 µg of total RNA was converted to cDNA using oligo-dT primers. 5 µL of the RT reaction was used to set up a PCR using gene-specific primers. Actin mRNA was used as a control. PCR products were separated on a 1.5% agarose-TAE gel. The RNAi clones used were: L4440 empty vector control, ncr-1 (clone F02E8.6, Ahringer Library), ncr-2 (clone F09G8.4, Ahringer Library), obr-3 (clone ZK1086.1, Ahringer Library), obr-2 (clone F14H8.1, Ahringer Library), (ostm1_name) (clone F42A8.3, Ahringer Library), snx-3 (clone W06D4.5, Ahringer Library), manba (clone C33G3.4, Ahringer Library), aman (clone F55D10.1, Ahringer Library), sul-3 (clone C54D2.4, Ahringer Library), gba-3 (clone F11E6.1, Ahringer Library) and asml (clone B0252.2, Ahringer Library).

Coelomocyte labeling experiments. Coelomocyte labeling and competition experiments were carried out with I4$^{cLY}_{A647}$, and Clensor$_{A647}$. For microinjections, the samples were diluted to 100 nM using 1× Medium 1 (150 mM NaCl, 5 mM KCl, 1 mM CaCl$_2$, 1 mM MgCl$_2$, 20 mM HEPES, pH 7.2). Injections were performed, in the dorsal side in the pseudocoelom, just opposite the vulva, of one-day old wild type hermaphrodites using a Olympus IX53 Simple Inverted Microscope (Olympus Corporation of the Americas, Center Valley, Pa.) equipped with 40×, 0.6 NA objective, and microinjection setup (Narishige, Japan). Injected worms were mounted on 2.0% agarose pad and anesthetized using 40 mM sodium azide in M9 buffer. In all cases labeling was checked after 1 h incubation at 22° C.

Colocalization experiments. I4$^{cLY}_{A647}$ or Clensor$_{A647}$ sample was diluted to 500 nM using 1× Medium 1 and injected in 10 arIs37 [pmyo-3::ssGFP] hermaphrodites. Imaging and quantification of the number of coelomocytes labeled, after 1 hr of incubation, was carried out on the Leica TCS SP5 II STED laser scanning confocal microscope (Leica Microsystems, Inc., Buffalo Grove, Ill.) using an Argon ion laser for 488 nm excitation and He—Ne laser for 633 excitation with a set of dichroics, excitation, and emission filters suitable for each fluorophore. Cross talk and bleed-through were measured and found to be negligible between the GFP/ALEXA 488/BAC channel and ALEXA 647 channel.

In vitro fluorescence measurements. Fluorescence spectra were measured on a FluoroMax-4 Scanning Spectrofluorometer (Horiba Scientific, Edison, N.J., USA). For pH measurements, $I4^{cLY}{}_{A488/A647}$ was diluted to 50 nM in 1× pH clamping buffer of desired pH for all in vitro fluorescence experiments. All samples were vortexed and equilibrated for 30 min at room temperature. The samples were excited at 488 nm and emission collected between 505 nm-750 nm. A calibration curve was obtained by plotting the ratio of donor emission intensity (D) at 520 nm and acceptor intensity (A) at 669 nm (for A488/A647) as a function of pH. Mean of D/A from three independent experiments and their SEM were plotted for each pH value.

For chloride measurements, 10 μM stock of Clensor was diluted to a final concentration of 200 nM using 10 mM sodium phosphate buffer, pH 7.2 and incubated for 30 min at room temperature prior to experiments. The emission spectra of BAC and ALEXA 647 were acquired by exciting the samples at 435 nm for BAC and 650 nm for ALEXA 647 respectively. Emission spectra of BAC and ALEXA 647 were collected between 495-550 nm and 650-700 nm respectively. In order to study the chloride sensitivity of Clensor, final chloride concentrations ranging between 5 mM to 100 mM were achieved by addition of microliter aliquots of 1 M stock of NaCl to 400 μL of sample. Emission intensity of BAC at 505 nm (G) was normalized to emission intensity of ALEXA 647 at 670 nm (R). Fold change in R/G ratio was calculated from the ratio of R/G values at two specific values of [CF].

In vivo measurements. pH clamping and measurement experiments were carried out with $I4^{cLY}{}_{A488/A647}$. For microinjections, the I-switch sample was diluted to 500 nM using 1× Medium 1. Worms were incubated at 22° C. for 1 hr and then immersed in clamping buffers (120 mM KCl, 5 mM NaCl, 1 mM $MgCl_2$, 1 mM $CaCl_2$, 20 mM HEPES) of varying pH, containing 100 μM nigericin and 100 μM monensin. In order to facilitate entry of the buffer into the body, the cuticle was perforated at three regions of the body using a microinjection needle. After 75 mins incubation in the clamping buffer, coelomocytes were imaged using wide field microscopy. Three independent measurements, each with 10 worms, were made for each pH value. Chloride clamping and measurements were carried out using Clensor. Worms were injected with 2 μM of Clensor and incubated at 22° C. for 2 hrs. To obtain the chloride calibration profile, the worms were then immersed in the appropriate chloride clamping buffer containing a specific concentration of chloride, 100 μM nigericin, 100 μM valinomycin, 100 μM monensin and 10 μM chloride ionophore I for 45 mins at room temperature. Chloride calibration buffers containing different chloride concentrations were prepared by mixing the 1×+ve chloride buffer (120 mM KCl, 20 mM NaCl, 1 mM CaCl2, 1 mM MgCl2, 20 mM HEPES, pH, 7.2) and 1×-ve chloride buffer (120 mM $KNO_3$, 20 mM $NaNO_3$, 1 mM $Ca(NO_3)_2$, 1 mM $Mg(NO_3)_2$, 20 mM HEPES, pH 7.2) in different ratios.

For real-time pH or chloride measurements, 10 hermaphrodites were injected with $I4^{cLY}{}_{A488/A647}$ or Clensor respectively and incubated at 22° C. for one hour. Worms were then anaesthetized and imaged on a wide field inverted microscope for pH measurements and confocal microscope for chloride measurements.

Microscopy. Wide field microscopy was carried out on IX83 research inverted microscope (Olympus Corporation of the Americas, Center Valley, Pa., USA) using a 60×, 1.42 NA, phase contrast oil immersion objective (PLAPON, Olympus Corporation of the Americas, Center Valley, Pa., USA) and Evolve® Delta 512 EMCCD camera (Photometrics, USA). Filter wheel, shutter and CCD camera were controlled using Metamorph Premier Ver 7.8.12.0 (Molecular Devices, LLC, USA), suitable for the fluorophores used. Images on the same day were acquired under the same acquisition settings. All the images were background subtracted taking mean intensity over an adjacent cell free area. Mean intensity in each endosome was measured in donor (D) and acceptor (A) channels. ALEXA 488 channel images (D) were obtained using 480/20 band pass excitation filter, 520/40 band pass emission filter and a 89016-ET-FITC/CY3/CY5 dichroic filter. ALEXA 647 channel images (A) were obtained using 640/30 band pass excitation filter, 705/72 band pass emission filter and 89016-ET-FITC/CY3/CY5 dichroic filter. For FRET channel images were obtained using the 480/20 band pass excitation filter, 705/72 band pass emission filter and 89016-ET-FITC/CY3/CY5 dichroic filter. Mean intensity in each endosome was measured in donor and acceptor channels. A ratio of donor to acceptor intensities (D/A) was obtained from these readings. Pseudocolor images were generated by calculating the D/A ratio per pixel. Confocal images were captured with a Leica TCS SP5 II STED laser scanning confocal microscope (Leica Microsystems, Inc., Buffalo Grove, Ill., USA) equipped with 63×, 1.4 NA, oil immersion objective. ALEXA 488 was excited using an Argon ion laser for 488 nm excitation, ALEXA 647 using He—Ne laser for 633 excitation and BAC using Argon ion laser for 458 nm excitation with a set of dichroics, excitation, and emission filters suitable for each fluorophore.

Image analysis. Images were analyzed with ImageJ ver 1.49 (NIH, USA). For pH measurements ALEXA 488 and ALEXA 647 images were overlapped using ImageJ and endosomes showing colocalization were selected for further analysis. Intensity in each endosome was measured in donor (D) and FRET (A) channels and recorded in an OriginPro Sr2 b9.2.272 (OriginLab Corporation, Northampton, Mass., USA) file from which D/A ratio of each endosome was obtained. The mean D/A of each distribution were converted in to pH according to the intracellular calibration curve. Data was represented as mean pH value±standard error of the mean. Data for pH clamping experiments was analysed similarly.

For chloride measurements, regions of cells containing lysosomes in each ALEXA 647 (R) image were identified and marked in the ROI plugin in ImageJ. The same regions were identified in the BAC (G) image recalling the ROIs and appropriate correction factor for chromatic aberration if necessary. After background subtraction, intensity for each endosome was measured and recorded in an Origin file. A ratio of R to G intensities (R/G) was obtained from these values by dividing the intensity of a given endosome in the R image with the corresponding intensity in the G image. For a given experiment, mean [Cl⁻] of an organelle population was determined by converting the mean R/G value of the distribution to [CF] values according to the intracellular calibration profile. Data was presented as mean of this mean [CF] value±standard error of the mean. Data for chloride clamping experiments was analyzed similarly.

Colocalization of GFP/YFP and ALEXA 647 was determined by counting the numbers of ALEXA 647 positive puncta that colocalize with GFP/YFP and representing it as a Pearson's correlation coefficient.

Lysosomal labelling in coelomocytes. Temporal mapping of I-switch and Clensor was done in 10 worms of pwIs50 [lmp-1::GFP+Cb-unc-119(+)]. Briefly, worms were injected with 500 nM of I4$^{cLY}_{A647}$ or Clensor$^{A647}$, incubated at 22° C. for one hour, and then imaged using Leica TCS SP5 II STED laser scanning confocal microscope (Leica Microsystems, Inc., Buffalo Grove, Ill., USA). Colocalization of GFP and I4$^{cLY}_{A647}$ or Clensor$^{A647}$ was determined by counting the numbers of ALEXA647 positive puncta that colocalize with GFP positive puncta and expressing them as a percentage of the total number of ALEXA 647 positive puncta. In order to confirm lysosomal labeling in a given genetic background, the same procedure was performed on the relevant mutant or RNAi knockdown in pwIs50 [lmp-1::GFP+Cb-unc-119(+)].

Cholesterol extraction and thin layer chromatography. L4 worms were placed on plates containing OP50 or bacteria expressing specific dsRNA against genes of choice. Gravid worms were allowed to lay eggs on the new plates and were removed 24 hours later. The F1 progeny were allowed to grow to adult stage. Young adults from three such plates were then washed off, spun down at 1,000×g for 30 s in centrifuge tubes, and washed four times with worm wash buffer (1×PBS). The worm pellet was resuspended in 400 µL wash buffer. A 100-µL worm suspension was taken out to extract total soluble protein. The quantity of total soluble protein of each 100 µL sample was measured using Bradford Assay. A specific volume of worm suspension was removed from the 300 µL sample that corresponded to 400 µg total soluble protein as estimated by the Bradford assay for a given genetic background. Worms in this volume then were spun down and subjected to lipid extraction essentially following published protocols. In brief, the worm pellet was homogenized on ice by sonication (Sonic Dismembrator, Fisher Scientific, USA), and 1 mL cold solution I (10:10: 1::CHCl$_3$:CH$_3$OH:HCOOH) was added. The tube was vortexed vigorously. Then 1.5 mL cold solution II (10:10:2:: CHCl$_3$:CH$_3$OH:H$_2$O) was added. The tube was vortexed vigorously again and stored at −20° C. overnight to allow sufficient extraction. Total lipids were extracted from the CHCl$_3$ layer and the solution was evaporated completely in a Rotavapor® (Buchi, New Castle, Del., USA). Dried total lipids then were redissolved in dichloromethane and 1 µL was loaded onto a silica gel TLC plate (Fluka). TLC reference cholesterol was loaded alongside and was run in a solvent system of 25% ethyl acetate/hexane. After the TLC plate dried, the TLC was dipped in 10% w/v phosphomolybdic acid in absolute ethanol solution and heated to 110° C. TLC were imaged on a gel doc system (GelDoc-Ite Imaging Systems, UVP, USA) and quantified on ImageJ ver 1.49 (NIH, USA).

The foregoing description is considered as illustrative only of the principles of the invention. Further, since numerous modifications and changes will readily occur to those skilled in the art, it is not desired to limit the invention to the exact construction and process as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

REFERENCES

The following references, to the extent that they provide exemplary procedural or other details supplementary to those set forth herein, are specifically incorporated herein by reference.

Y. Krishnan and M. Bathe, Trends in Cell Biol., 2012, 22, 624-633.
Y. Krishnan and F. C. Simmel, Angew. Chem. Int. Ed. 2011, 50, 3124-3156.
T. A. Brooks, S. Kendrick and L. M. Hurley, FEBS Journal, 2010, 277, 3459-3469.
T. Simonsson, M. Pribylova and M. Vorlickova, Biochem. Biophys. Res. Commun., 2000, 278, 158-166.
K. Gehring, J. L. Leroy and M. Gueron, Nature 1993, 363, 561-565.
T. E. Malliavin, J. Gau, K. Snoussi and J. L. Leroy, Biophy. Journal, 2003, 84, 3838-3847.
Y. Chen, S. H. Lee and C. Mao, Angew. Chem. Int. Ed. 2004, 43, 5335-5338.
Z. Liu and C. Mao, Chem. Commun., 2014, 50, 8239-8241.
D. Liu, A. Bruckbauer, C. Abell, S. Balasubramanian, D. J. Kang, D. Klenerman and D. Zhou, J. Am. Chem. Soc., 2006, 128, 2067-2071.
D. Liu and S. Balasubramanian, Angew. Chem. Int. Ed. 2003, 42, 5734-5736.
A. Idili, A. Vallee-Belisle and F. Ricci, J. Am. Chem. Soc. 2014, 136, 5836-5839.
H. Meng, Y. Yang, Y. Chen, Y. Zhou, Y. Liu, X. Chen, H. Ma, Z. Tang, D. Liu and L. Jiang, Chem. Commun., 2009, 2293-2295.
S. Modi, C. Nizak, S. Surana, S. Halder and Y. Krishnan, Nat. Nanotechol., 2013, 8, 459.
S. Modi, M. G. Swetha, D. Goswami, G. D. Gupta, S. Mayor and Y. Krishnan, Nat. Nanotechol., 4, 325-330.
S. Surana, J. M. Bhat, S. P. Koushika and Y. Krishnan, Nat. Commun., 2011, 2, 1-7.
J. L. Mergny, L. Lacroix, X. Han, J. L. Leroy and C. Hélène, J. Am. Chem. Soc., 1995, 117, 8887-8898.
S. Modi, S. Halder, C. Nizak and Y. Krishnan, Nanoscale, 2014, 6, 1144-1152.
I. V. Nesterova and E. E. Nesterova, J. Am. Chem. Soc., 2014, 136, 8843-8846.
E. M. Moody and P. C. Bevilacqua, J. Am. Chem. Soc., 2003, 125, 16285-16293.
P. Buceka, R. Gargallob and A. Kudrev, Analytica Chimica Acta, 2010, 683, 69-77.
J. L. Leroy, M. Gueron, J. L. Mergny and C. Hélène, Nucleic Acids Res., 1994, 22, 1600-1606.
N. K. Sharma and K. N. Ganesh, Chem. Commun., 2005, 4330-4332.
B. Datta, M. E. Bier, S. Roy and B. A. Armitage, j. Am. Chem. Soc., 2005, 127, 4199-4207.
A. Pasternak and J. Wengel, Bioorg. Med. Chem. Lett., 2011, 21, 752-755.
A. Pasternak and J. Wengel, Org. Biomol. Chem., 2011, 9, 3591-3597.
P. Perlkov, K. K. Karlsen, E. B. Pedersen and J. Wengel, Chembiochem., 2014, 15, 146-156.
T. Kulikowski and D. Shugar, Acta Biochem. Polonica, 1979, 26, 145-160.
N. Kumar, M. Petersen and S. Maiti, Chem. Commun., 2009, 1532-1534
R. Z. Jin, K. J. Breslauer, R. A. Jones and B. L. Gaffney, Science, 1990, 250, 543-546.
E. L. Edwards, M. H. Patrick, R. L. Ratliff and D. M. Gray, Biochemistry, 1990, 29, 828-836.

H. Kanehara, M. Mizuguchi, K. Tajima, K. Kanaori, and K. Makino, Biochemistry, 1997, 36, 1790-1797.

M. Kaushik, N. Suehl and L. A. Marky, Biochemistry, 2007, 126, 154-164.

M. M. Dailey, M. C. Miller, P. J. Bates, A. N. Lane and J. O. Trent, Nucleic Acids Res. 2010, 38, 4877-4888.

A. T. Phan and J. L. Mergny, Nucleic Acids Res., 2002, 30, 4618-4625.

A. L. Lieblein, B. Furtig and H. Schwalbe, Chembiochem., 2013, 14, 1226-1230. J. Zhou, C.

Wei, G. Jia, X. Wang, Z. Fenga and C. Li, *Mol. BioSyst.*, 2010, 6, 580-586.

P. V. Scaria, S. J. Shire, and R. H. Shafer, *Proc. Natl. Acad. Sci., USA,* 1992, 89, 10336-10340.

J. Choi, S. Kim, T. Tachikawa, M. Fujitsuka, and T. Majima, *JACS,* 2011, 133, 16146-16153.

S. Modi, M. G. Swetha, D. Goswami, G. D. Gupta, S. Mayor and Y. Krishnan, *Nat. Nanotechnol.,* 2009, 4, 325-330; S. Surana, J. M. Bhat, S. P. Koushika and Y. Krishnan, *Nat. Commun.,* 2011, 2, 340-346.

U.S. Pat. No. 8,153,437

U.S. Pat. No. 8,216,850

U.S. patent application Ser. No. 12/474,550

US patent application U.S. Ser. No. 14/351,400

International Patent application PCT/M2014/059236

Indian Patent application 1471/CHE/2011

Indian Patent application 3252/CHE/2011

The invention claimed is:

1. A nucleic acid complex comprising:

i) a first single-stranded nucleic acid molecule comprising the nucleic acid sequence:

```
                                                  (SEQ ID NO. 8)
5'-CCCTAACCCCTAAC*CC*CTAACC*CC*ATATATATCCTAGAACGAC

AGACAAACAGTGAGTC-3;

(SEQ ID NO. 9)
5'-CCC*CTAACC*CCTAACCC*CTAACC*CCATATATATCCTAGAACGA

CAGACAAACAGTGAGTC-3';

(SEQ ID NO. 10)
5'-C*CCCTAACCCC*TAAC*CCCTAACCCC*ATATATATCCTAGAACGA

CAGACAAACAGTGAGTC-3';
or (SEQ ID NO. 11)
5'-C*C*C*C*TAACCCCTAACCCCTAACCCCATATATATCCTAGAACGA

CAGACAAACAGTGAGTC-3';
``` wherein C* is a 5'-bromocytosine or 5'-methylcytosine and wherein the first single-stranded nucleic acid molecule is conjugated to a first fluorophore which comprises a donor fluorophore as a first label; and ii) a second single-stranded nucleic acid molecule that is partially or fully complementary to the first single-stranded molecule, wherein the second single-stranded nucleic acid molecule comprises the nucleic acid sequence:

5'-GACTCACTGTTTGTCTGTCGTTCTAGGATAT*ATATTTGTTATGTGTTATGTGTTA T-3' (SEQ ID NO:19)(P comp) and wherein T* is conjugated to a second fluorophore which comprises an acceptor fluorophore as a second label, wherein the first and the second labels are a donor-acceptor pair.

2. The nucleic acid complex of claim 1, wherein C* is 5'-bromocysteine.

3. The nucleic acid complex of claim 1, wherein C* is 5'-methylcytosine.

* * * * *

SEQUENCE LISTING

```
<160> NUMBER OF SEQ ID NOS: 44

<210> SEQ ID NO 1
<211> LENGTH: 12
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: Lysine tagged
<220> FEATURE:
<221> NAME/KEY: misc_feature
<222> LOCATION: (12)..(12)
<223> OTHER INFORMATION: Lysine tagged

<400> SEQUENCE: 1
atcaacactg ca                                                          12

<210> SEQ ID NO 2
<211> LENGTH: 38
<212> TYPE: DNA
<213> ORGANISM: Artificial Sequence
<220> FEATURE:
<223> OTHER INFORMATION: Synthetic Primer

<400> SEQUENCE: 2
tatatatagg atcttgctgt ctggtgtgca gtgttgat                              38

<210> SEQ ID NO 3
<211> LENGTH: 26
<212> TYPE: DNA
<213> ORGANISM: Artificial Sequence
<220> FEATURE:
<223> OTHER INFORMATION: Synthetic Primer

<400> SEQUENCE: 3
caccagacag caagatccta tatata                                           26

<210> SEQ ID NO 4
<211> LENGTH: 69
<212> TYPE: DNA
<213> ORGANISM: Artificial Sequence
<220> FEATURE:
<223> OTHER INFORMATION: Synthetic Primer

<400> SEQUENCE: 4
caccagacag caagatccta tatagggg gaucaaucca agggacccgg aaacgcuccc        60
uuacacccc                                                              69
```

```
<210> SEQ ID NO 5
<211> LENGTH: 43
<212> TYPE: RNA
<213> ORGANISM: Artificial Sequence
<220> FEATURE:
<223> OTHER INFORMATION: Synthetic Primer

<400> SEQUENCE: 5
gggggaucaa uccaagggac ccggaaacgc ucccuuacac ccc        43

<210> SEQ ID NO 6
<211> LENGTH: 17
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (2)..(2)
<223> OTHER INFORMATION: C or absent
<220> FEATURE:
<221> NAME/KEY: misc_feature
<222> LOCATION: (3)..(3)
<223> OTHER INFORMATION: A, T, G or absent
<220> FEATURE:
<221> NAME/KEY: misc_feature
<222> LOCATION: (4)..(4)
<223> OTHER INFORMATION: A, T, G or absent
<220> FEATURE:
<221> NAME/KEY: misc_feature
<222> LOCATION: (5)..(5)
<223> OTHER INFORMATION: A, T, G or absent
<220> FEATURE:
<221> NAME/KEY: misc_feature
<222> LOCATION: (7)..(7)
<223> OTHER INFORMATION: C or absent
<220> FEATURE:
<221> NAME/KEY: misc_feature
<222> LOCATION: (8)..(8)
<223> OTHER INFORMATION: A, T, G or absent
<220> FEATURE:
<221> NAME/KEY: misc_feature
<222> LOCATION: (9)..(9)
<223> OTHER INFORMATION: A, T, G or absent
<220> FEATURE:
<221> NAME/KEY: misc_feature
<222> LOCATION: (10)..(10)
<223> OTHER INFORMATION: A, T, G or absent
<220> FEATURE:
<221> NAME/KEY: misc_feature
<222> LOCATION: (12)..(12)
<223> OTHER INFORMATION: C or absent
<220> FEATURE:
<221> NAME/KEY: misc_feature
<222> LOCATION: (13)..(13)
<223> OTHER INFORMATION: A, T, G or absent
<220> FEATURE:
<221> NAME/KEY: misc_feature
<222> LOCATION: (14)..(14)
<223> OTHER INFORMATION: A, T, G or absent
<220> FEATURE:
<221> NAME/KEY: misc_feature
<222> LOCATION: (15)..(15)
<223> OTHER INFORMATION: A, T, G or absent
<220> FEATURE:
<221> NAME/KEY: misc_feature
<222> LOCATION: (17)..(17)
<223> OTHER INFORMATION: C or absent

<400> SEQUENCE: 6
ccnnnccnnn ccnnncc        17

<210> SEQ ID NO 7
<211> LENGTH: 15
<212> TYPE: DNA
```

```
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: C or absent
<220> FEATURE:
<221> NAME/KEY: misc_feature
<222> LOCATION: (2)..(2)
<223> OTHER INFORMATION: C or absent
<220> FEATURE:
<221> NAME/KEY: misc_feature
<222> LOCATION: (3)..(3)
<223> OTHER INFORMATION: C or absent
<220> FEATURE:
<221> NAME/KEY: misc_feature
<222> LOCATION: (4)..(4)
<223> OTHER INFORMATION: A, T, G or absent
<220> FEATURE:
<221> NAME/KEY: misc_feature
<222> LOCATION: (5)..(5)
<223> OTHER INFORMATION: C or absent
<220> FEATURE:
<221> NAME/KEY: misc_feature
<222> LOCATION: (6)..(6)
<223> OTHER INFORMATION: C or absent
<220> FEATURE:
<221> NAME/KEY: misc_feature
<222> LOCATION: (7)..(7)
<223> OTHER INFORMATION: C or absent
<220> FEATURE:
<221> NAME/KEY: misc_feature
<222> LOCATION: (8)..(8)
<223> OTHER INFORMATION: A, T, G or absent
<220> FEATURE:
<221> NAME/KEY: misc_feature
<222> LOCATION: (9)..(9)
<223> OTHER INFORMATION: C or absent
<220> FEATURE:
<221> NAME/KEY: misc_feature
<222> LOCATION: (10)..(10)
<223> OTHER INFORMATION: C or absent
<220> FEATURE:
<221> NAME/KEY: misc_feature
<222> LOCATION: (11)..(11)
<223> OTHER INFORMATION: C or absent
<220> FEATURE:
<221> NAME/KEY: misc_feature
<222> LOCATION: (12)..(12)
<223> OTHER INFORMATION: A, T, G or absent
<220> FEATURE:
<221> NAME/KEY: misc_feature
<222> LOCATION: (13)..(13)
<223> OTHER INFORMATION: C or absent
<220> FEATURE:
<221> NAME/KEY: misc_feature
<222> LOCATION: (14)..(14)
<223> OTHER INFORMATION: C or absent
<220> FEATURE:
<221> NAME/KEY: misc_feature
<222> LOCATION: (15)..(15)
<223> OTHER INFORMATION: C or absent

<400> SEQUENCE: 7 cccnccncc cnccc                                              15

<210> SEQ ID NO 8
<211> LENGTH: 59
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (14)..(14)
<223> OTHER INFORMATION: Modified C
```

```
<220> FEATURE:
<221> NAME/KEY: misc_feature
<222> LOCATION: (16)..(16)
<223> OTHER INFORMATION: Modified C
<220> FEATURE:
<221> NAME/KEY: misc_feature
<222> LOCATION: (22)..(22)
<223> OTHER INFORMATION: Modified C
<220> FEATURE:
<221> NAME/KEY: misc_feature
<222> LOCATION: (24)..(24)
<223> OTHER INFORMATION: Modified C

<400> SEQUENCE: 8
ccctaacccc taaccccctaa ccccatatat atcctagaac gacagacaaa cagtgagtc      59

<210> SEQ ID NO 9
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: Modified C
<220> FEATURE:
<221> NAME/KEY: misc_feature
<222> LOCATION: (9)..(9)
<223> OTHER INFORMATION: Modified C
<220> FEATURE:
<221> NAME/KEY: misc_feature
<222> LOCATION: (17)..(17)
<223> OTHER INFORMATION: Modified C
<220> FEATURE:
<221> NAME/KEY: misc_feature
<222> LOCATION: (23)..(23)
<223> OTHER INFORMATION: Modified C

<400> SEQUENCE: 9
cccctaaccc ctaaccccta accccatata tatcctagaa cgacagacaa acagtgagtc      60

<210> SEQ ID NO 10
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: Modified C
<220> FEATURE:
<221> NAME/KEY: misc_feature
<222> LOCATION: (11)..(11)
<223> OTHER INFORMATION: Modified C
<220> FEATURE:
<221> NAME/KEY: misc_feature
<222> LOCATION: (15)..(15)
<223> OTHER INFORMATION: Modified C
<220> FEATURE:
<221> NAME/KEY: misc_feature
<222> LOCATION: (25)..(25)
<223> OTHER INFORMATION: Modified C

<400> SEQUENCE: 10
cccctaaccc ctaaccccta accccatata tatcctagaa cgacagacaa acagtgagtc      60

<210> SEQ ID NO 11
<211> LENGTH: 60
<212> TYPE: DNA
<213> ORGANISM: Artificial Sequence
<220> FEATURE:
```

```
<223> OTHER INFORMATION: Synthetic Primer
<220> FEATURE:
<221> NAME/KEY: misc_feature
<222> LOCATION: (1)..(1)
<223> OTHER INFORMATION: Modified C
<220> FEATURE:
<221> NAME/KEY: misc_feature
<222> LOCATION: (2)..(2)
<223> OTHER INFORMATION: Modified C
<220> FEATURE:
<221> NAME/KEY: misc_feature
<222> LOCATION: (3)..(3)
<223> OTHER INFORMATION: Modified C
<220> FEATURE:
<221> NAME/KEY: misc_feature
<222> LOCATION: (4)..(4)
<223> OTHER INFORMATION: Modified C

<400> SEQUENCE: 11
cccctaaccc ctaaccccta acccatata tatcctagaa cgacagacaa acagtgagtc     60

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
cccctaaccc ctaaccccta acccc                                         25

<210> SEQ ID NO 13
<211> LENGTH: 37
<212> TYPE: DNA
<213> ORGANISM: Artificial Sequence
<220> FEATURE:
<223> OTHER INFORMATION: Synthetic Primer

<400> SEQUENCE: 13
ccccccctaa cccccctaa ccccccctaa ccccccc                             37

<210> SEQ ID NO 14
<211> LENGTH: 21
<212> TYPE: DNA
<213> ORGANISM: Artificial Sequence
<220> FEATURE:
<223> OTHER INFORMATION: Synthetic Primer

<400> SEQUENCE: 14
ccctaaccct aaccctaacc c                                             21

<210> SEQ ID NO 15
<211> LENGTH: 25
<212> TYPE: DNA
<213> ORGANISM: Artificial Sequence
<220> FEATURE:
<223> OTHER INFORMATION: Synthetic Primer

<400> SEQUENCE: 15
cccctaaccc ctaaccccta acccc                                         25

<210> SEQ ID NO 16
<211> LENGTH: 22
<212> TYPE: DNA
<213> ORGANISM: Artificial Sequence
<220> FEATURE:
<223> OTHER INFORMATION: Synthetic Primer

<400> SEQUENCE: 16
```

```
tttgttatgt gttatgtgtt at                                              22
```

<210> SEQ ID NO 17
<211> LENGTH: 60
<212> TYPE: DNA
<213> ORGANISM: Artificial Sequence
<220> FEATURE:
<223> OTHER INFORMATION: Synthetic Primer

<400> SEQUENCE: 17

```
cccctaaccc ctaaccccta acccatata tatcctagaa cgacagacaa acagtgagtc     60
```

<210> SEQ ID NO 18
<211> LENGTH: 72
<212> TYPE: DNA
<213> ORGANISM: Artificial Sequence
<220> FEATURE:
<223> OTHER INFORMATION: Synthetic Primer

<400> SEQUENCE: 18

```
ccccccctaa ccccccctaa ccccccctaa cccccccata tatatcctag aacgacagac    60
aaacagtgag tc                                                        72
```

<210> SEQ ID NO 19
<211> LENGTH: 57
<212> TYPE: DNA
<213> ORGANISM: Artificial Sequence
<220> FEATURE:
<223> OTHER INFORMATION: Synthetic Primer

<400> SEQUENCE: 19

```
gactcactgt ttgtctgtcg ttctaggata tatattttgt tatgtgttat gtgttat       57
```

<210> SEQ ID NO 20
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled

<400> SEQUENCE: 20

```
cccctaaccc ctaaccccta acccatata tatcctagaa cgacagacaa acagtgagtc     60
```

<210> SEQ ID NO 21
<211> LENGTH: 72
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled

<400> SEQUENCE: 21

```
ccccccctaa ccccccctaa ccccccctaa cccccccata tatatcctag aacgacagac    60
aaacagtgag tc                                                        72
```

<210> SEQ ID NO 22
<211> LENGTH: 57
<212> TYPE: DNA

<213> ORGANISM: Artificial Sequence
<220> FEATURE:
<223> OTHER INFORMATION: Synthetic Primer
<220> FEATURE:
<221> NAME/KEY: misc_feature
<222> LOCATION: (34)..(34)
<223> OTHER INFORMATION: T labeled with Alexa 647

<400> SEQUENCE: 22
gactcactgt tgtctgtcg ttctaggata tatattttgt tatgtgttat gtgttat        57

<210> SEQ ID NO 23
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (15)..(15)
<223> OTHER INFORMATION: 5'-bromocytosine
<220> FEATURE:
<221> NAME/KEY: misc_feature
<222> LOCATION: (17)..(17)
<223> OTHER INFORMATION: 5'-bromocytosine
<220> FEATURE:
<221> NAME/KEY: misc_feature
<222> LOCATION: (23)..(23)
<223> OTHER INFORMATION: 5'-bromocytosine
<220> FEATURE:
<221> NAME/KEY: misc_feature
<222> LOCATION: (25)..(25)
<223> OTHER INFORMATION: 5'-bromocytosine

<400> SEQUENCE: 23
cccctaaccc ctaaccccta acccatata tatcctagaa cgacagacaa acagtgagtc        60

<210> SEQ ID NO 24
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: 5'-Bromocytosine
<220> FEATURE:
<221> NAME/KEY: misc_feature
<222> LOCATION: (9)..(9)
<223> OTHER INFORMATION: 5'-Bromocytosine
<220> FEATURE:
<221> NAME/KEY: misc_feature
<222> LOCATION: (17)..(17)
<223> OTHER INFORMATION: 5'-Bromocytosine
<220> FEATURE:
<221> NAME/KEY: misc_feature
<222> LOCATION: (23)..(23)
<223> OTHER INFORMATION: 5'-Bromocytosine

<400> SEQUENCE: 24
cccctaaccc ctaaccccta acccatata tatcctagaa cgacagacaa acagtgagtc        60

<210> SEQ ID NO 25
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5-Bromocytosine

```
<220> FEATURE:
<221> NAME/KEY: misc_feature
<222> LOCATION: (11)..(11)
<223> OTHER INFORMATION: 5-Bromocytosine
<220> FEATURE:
<221> NAME/KEY: misc_feature
<222> LOCATION: (15)..(15)
<223> OTHER INFORMATION: 5-Bromocytosine
<220> FEATURE:
<221> NAME/KEY: misc_feature
<222> LOCATION: (25)..(25)
<223> OTHER INFORMATION: 5-Bromocytosine

<400> SEQUENCE: 25
cccctaaccc ctaaccccta accccatata tatcctagaa cgacagacaa acagtgagtc    60

<210> SEQ ID NO 26
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5-Bromocytosine
<220> FEATURE:
<221> NAME/KEY: misc_feature
<222> LOCATION: (2)..(2)
<223> OTHER INFORMATION: 5-Bromocytosine
<220> FEATURE:
<221> NAME/KEY: misc_feature
<222> LOCATION: (3)..(3)
<223> OTHER INFORMATION: 5-Bromocytosine
<220> FEATURE:
<221> NAME/KEY: misc_feature
<222> LOCATION: (4)..(4)
<223> OTHER INFORMATION: 5-Bromocytosine

<400> SEQUENCE: 26
cccctaaccc ctaaccccta accccatata tatcctagaa cgacagacaa acagtgagtc    60

<210> SEQ ID NO 27
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled
<220> FEATURE:
<221> NAME/KEY: misc_feature
<222> LOCATION: (15)..(15)
<223> OTHER INFORMATION: 5'-Bromocytosine
<220> FEATURE:
<221> NAME/KEY: misc_feature
<222> LOCATION: (17)..(17)
<223> OTHER INFORMATION: 5'-Bromocytosine
<220> FEATURE:
<221> NAME/KEY: misc_feature
<222> LOCATION: (23)..(23)
<223> OTHER INFORMATION: 5'-Bromocytosine
<220> FEATURE:
<221> NAME/KEY: misc_feature
<222> LOCATION: (25)..(25)
<223> OTHER INFORMATION: 5'-Bromocytosine

<400> SEQUENCE: 27
cccctaaccc ctaaccccta accccatata tatcctagaa cgacagacaa acagtgagtc    60

<210> SEQ ID NO 28
```

```
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled
<220> FEATURE:
<221> NAME/KEY: misc_feature
<222> LOCATION: (3)..(3)
<223> OTHER INFORMATION: 5'-Bromocytosine
<220> FEATURE:
<221> NAME/KEY: misc_feature
<222> LOCATION: (9)..(9)
<223> OTHER INFORMATION: 5'-Bromocytosine
<220> FEATURE:
<221> NAME/KEY: misc_feature
<222> LOCATION: (17)..(17)
<223> OTHER INFORMATION: 5'-Bromocytosine
<220> FEATURE:
<221> NAME/KEY: misc_feature
<222> LOCATION: (23)..(23)
<223> OTHER INFORMATION: 5'-Bromocytosine

<400> SEQUENCE: 28
cccctaaccc ctaaccccta accccatata tatcctagaa cgacagacaa acagtgagtc      60

<210> SEQ ID NO 29
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled
<220> FEATURE:
<221> NAME/KEY: misc_feature
<222> LOCATION: (1)..(1)
<223> OTHER INFORMATION: 5'-Bromocytosine
<220> FEATURE:
<221> NAME/KEY: misc_feature
<222> LOCATION: (11)..(11)
<223> OTHER INFORMATION: 5'-Bromocytosine
<220> FEATURE:
<221> NAME/KEY: misc_feature
<222> LOCATION: (15)..(15)
<223> OTHER INFORMATION: 5'-Bromocytosine
<220> FEATURE:
<221> NAME/KEY: misc_feature
<222> LOCATION: (25)..(25)
<223> OTHER INFORMATION: 5'-Bromocytosine

<400> SEQUENCE: 29
cccctaaccc ctaaccccta accccatata tatcctagaa cgacagacaa acagtgagtc      60

<210> SEQ ID NO 30
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled
<220> FEATURE:
<221> NAME/KEY: misc_feature
<222> LOCATION: (1)..(1)
<223> OTHER INFORMATION: 5'-Bromocytosine
<220> FEATURE:
<221> NAME/KEY: misc_feature
```

```
<222> LOCATION: (2)..(2)
<223> OTHER INFORMATION: 5'-Bromocytosine
<220> FEATURE:
<221> NAME/KEY: misc_feature
<222> LOCATION: (3)..(3)
<223> OTHER INFORMATION: 5'-Bromocytosine
<220> FEATURE:
<221> NAME/KEY: misc_feature
<222> LOCATION: (4)..(4)
<223> OTHER INFORMATION: 5'-Bromocytosine

<400> SEQUENCE: 30
cccctaaccc ctaacccta accccatata tatcctagaa cgacagacaa acagtgagtc      60

<210> SEQ ID NO 31
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (15)..(15)
<223> OTHER INFORMATION: 5'-methylcytosine
<220> FEATURE:
<221> NAME/KEY: misc_feature
<222> LOCATION: (17)..(17)
<223> OTHER INFORMATION: 5'-methylcytosine
<220> FEATURE:
<221> NAME/KEY: misc_feature
<222> LOCATION: (23)..(23)
<223> OTHER INFORMATION: 5'-methylcytosine
<220> FEATURE:
<221> NAME/KEY: misc_feature
<222> LOCATION: (25)..(25)
<223> OTHER INFORMATION: 5'-methylcytosine

<400> SEQUENCE: 31
cccctaaccc ctaacccta accccatata tatcctagaa cgacagacaa acagtgagtc      60

<210> SEQ ID NO 32
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: 5'-methylcytosine
<220> FEATURE:
<221> NAME/KEY: misc_feature
<222> LOCATION: (9)..(9)
<223> OTHER INFORMATION: 5'-methylcytosine
<220> FEATURE:
<221> NAME/KEY: misc_feature
<222> LOCATION: (17)..(17)
<223> OTHER INFORMATION: 5'-methylcytosine
<220> FEATURE:
<221> NAME/KEY: misc_feature
<222> LOCATION: (23)..(23)
<223> OTHER INFORMATION: 5'-methylcytosine

<400> SEQUENCE: 32
cccctaaccc ctaacccta accccatata tatcctagaa cgacagacaa acagtgagtc      60

<210> SEQ ID NO 33
<211> LENGTH: 60
<212> TYPE: DNA
<213> ORGANISM: Artificial Sequence
<220> FEATURE:
<223> OTHER INFORMATION: Synthetic Primer
<220> FEATURE:
```

<221> NAME/KEY: misc_feature
<222> LOCATION: (1)..(1)
<223> OTHER INFORMATION: 5'-Methylcytosine
<220> FEATURE:
<221> NAME/KEY: misc_feature
<222> LOCATION: (11)..(11)
<223> OTHER INFORMATION: 5'-Methylcytosine
<220> FEATURE:
<221> NAME/KEY: misc_feature
<222> LOCATION: (15)..(15)
<223> OTHER INFORMATION: 5'-Methylcytosine
<220> FEATURE:
<221> NAME/KEY: misc_feature
<222> LOCATION: (25)..(25)
<223> OTHER INFORMATION: 5'-Methylcytosine

<400> SEQUENCE: 33
cccctaaccc ctaaccccta acccatata tatcctagaa cgacagacaa acagtgagtc    60

<210> SEQ ID NO 34
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5'-methylcytosine
<220> FEATURE:
<221> NAME/KEY: misc_feature
<222> LOCATION: (2)..(2)
<223> OTHER INFORMATION: 5'-methylcytosine
<220> FEATURE:
<221> NAME/KEY: misc_feature
<222> LOCATION: (3)..(3)
<223> OTHER INFORMATION: 5'-methylcytosine
<220> FEATURE:
<221> NAME/KEY: misc_feature
<222> LOCATION: (4)..(4)
<223> OTHER INFORMATION: 5'-methylcytosine

<400> SEQUENCE: 34
cccctaaccc ctaaccccta acccatata tatcctagaa cgacagacaa acagtgagtc    60

<210> SEQ ID NO 35
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled
<220> FEATURE:
<221> NAME/KEY: misc_feature
<222> LOCATION: (15)..(15)
<223> OTHER INFORMATION: 5'-Methylcytosine
<220> FEATURE:
<221> NAME/KEY: misc_feature
<222> LOCATION: (17)..(17)
<223> OTHER INFORMATION: 5'-Methylcytosine
<220> FEATURE:
<221> NAME/KEY: misc_feature
<222> LOCATION: (23)..(23)
<223> OTHER INFORMATION: 5'-Methylcytosine
<220> FEATURE:
<221> NAME/KEY: misc_feature
<222> LOCATION: (25)..(25)
<223> OTHER INFORMATION: 5'-Methylcytosine

<400> SEQUENCE: 35
cccctaaccc ctaaccccta acccatata tatcctagaa cgacagacaa acagtgagtc    60

<210> SEQ ID NO 36
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Akexa 488 labeled
<220> FEATURE:
<221> NAME/KEY: misc_feature
<222> LOCATION: (3)..(3)
<223> OTHER INFORMATION: 5'-methylcytosine
<220> FEATURE:
<221> NAME/KEY: misc_feature
<222> LOCATION: (9)..(9)
<223> OTHER INFORMATION: 5'-methylcytosine
<220> FEATURE:
<221> NAME/KEY: misc_feature
<222> LOCATION: (17)..(17)
<223> OTHER INFORMATION: 5'-methylcytosine
<220> FEATURE:
<221> NAME/KEY: misc_feature
<222> LOCATION: (23)..(23)
<223> OTHER INFORMATION: 5'-methylcytosine

<400> SEQUENCE: 36
cccctaaccc ctaacccta accccatata tatcctagaa cgacagacaa acagtgagtc     60

<210> SEQ ID NO 37
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled
<220> FEATURE:
<221> NAME/KEY: misc_feature
<222> LOCATION: (1)..(1)
<223> OTHER INFORMATION: 5'-methylcytosine
<220> FEATURE:
<221> NAME/KEY: misc_feature
<222> LOCATION: (11)..(11)
<223> OTHER INFORMATION: 5'-methylcytosine
<220> FEATURE:
<221> NAME/KEY: misc_feature
<222> LOCATION: (15)..(15)
<223> OTHER INFORMATION: 5'-methylcytosine
<220> FEATURE:
<221> NAME/KEY: misc_feature
<222> LOCATION: (25)..(25)
<223> OTHER INFORMATION: 5'-methylcytosine

<400> SEQUENCE: 37
cccctaaccc ctaacccta accccatata tatcctagaa cgacagacaa acagtgagtc     60

<210> SEQ ID NO 38
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Alexa 488 labeled
<220> FEATURE:
<221> NAME/KEY: misc_feature
<222> LOCATION: (1)..(1)

```
<223> OTHER INFORMATION: 5'-methylcytosine
<220> FEATURE:
<221> NAME/KEY: misc_feature
<222> LOCATION: (2)..(2)
<223> OTHER INFORMATION: 5'-methylcytosine
<220> FEATURE:
<221> NAME/KEY: misc_feature
<222> LOCATION: (3)..(3)
<223> OTHER INFORMATION: 5'-methylcytosine
<220> FEATURE:
<221> NAME/KEY: misc_feature
<222> LOCATION: (4)..(4)
<223> OTHER INFORMATION: 5'-methylcytosine

<400> SEQUENCE: 38
cccctaaccc ctaaccccta acccatata tatcctagaa cgacagacaa acagtgagtc      60

<210> SEQ ID NO 39
<211> LENGTH: 29
<212> TYPE: DNA
<213> ORGANISM: Artificial Sequence
<220> FEATURE:
<223> OTHER INFORMATION: Synthetic Primer

<400> SEQUENCE: 39
cccctaaccc ctaaccccta acccatat                                       29

<210> SEQ ID NO 40
<211> LENGTH: 24
<212> TYPE: DNA
<213> ORGANISM: Artificial Sequence
<220> FEATURE:
<223> OTHER INFORMATION: Synthetic Primer

<400> SEQUENCE: 40
tattttgtta tgtgttagtg ttat                                           24

<210> SEQ ID NO 41
<211> LENGTH: 29
<212> TYPE: DNA
<213> ORGANISM: Artificial Sequence
<220> FEATURE:
<223> OTHER INFORMATION: Synthetic Primer

<400> SEQUENCE: 41
cccctaaccc ctaaccccta acccatat                                       29

<210> SEQ ID NO 42
<211> LENGTH: 24
<212> TYPE: DNA
<213> ORGANISM: Artificial Sequence
<220> FEATURE:
<223> OTHER INFORMATION: Synthetic Primer

<400> SEQUENCE: 42
tattttgtta tgtgttagtg ttat                                           24

<210> SEQ ID NO 43
<211> LENGTH: 29
<212> TYPE: DNA
<213> ORGANISM: Artificial Sequence
<220> FEATURE:
<223> OTHER INFORMATION: Synthetic Primer

<400> SEQUENCE: 43
cccctaaccc ctaaccccta acccatat                                       29
```

```
<210> SEQ ID NO 44
<211> LENGTH: 24
<212> TYPE: DNA
<213> ORGANISM: Artificial Sequence
<220> FEATURE:
<223> OTHER INFORMATION: Synthetic Primer

<400> SEQUENCE: 44
tattttgtta tgtgttagtg ttat                                            24
```